United States Patent
Uchitel et al.

(10) Patent No.: US 8,662,891 B2
(45) Date of Patent: Mar. 4, 2014

(54) IMPLANTS, TOOLS, AND METHODS FOR SINUS LIFT AND LATERAL RIDGE AUGMENTATION

(75) Inventors: Ilan Uchitel, Kefar Saba (IL); Gideon Fostick, Givat Shmuel (KR); Hadar Better, Tel Aviv (IL); Yossi Gross, Moshav Mazor (IL)

(73) Assignee: Maxillent Ltd., Herzliya (JP)

( * ) Notice: Subject to any disclaimer, the term of this patent is extended or adjusted under 35 U.S.C. 154(b) by 17 days.

(21) Appl. No.: 13/314,818

(22) Filed: Dec. 8, 2011

(65) Prior Publication Data
US 2012/0094254 A1 Apr. 19, 2012

Related U.S. Application Data

(63) Continuation-in-part of application No. PCT/IL2010/000252, filed on Mar. 24, 2010, which is a continuation-in-part of application No. 12/485,199, filed on Jun. 16, 2009, now Pat. No. 8,029,284, and a continuation-in-part of application No. PCT/IL2009/000931, filed on Sep. 29, 2009, application No. 13/314,818, which is a continuation-in-part of application No. 13/040,440, filed on Mar. 4, 2011, now Pat. No. 8,356,994, which is a continuation of application No. 12/240,353, filed on Sep. 29, 2008, now Pat. No. 7,934,929.

(51) Int. Cl.
*A61C 8/00* (2006.01)

(52) U.S. Cl.
USPC ............................................. 433/174

(58) Field of Classification Search
USPC ..................... 433/172, 173, 174, 229
See application file for complete search history.

(56) References Cited

U.S. PATENT DOCUMENTS 2,347,567 A 4/1944 Kresse
2,436,623 A * 2/1948 Van Zile .................... 433/81
(Continued)

FOREIGN PATENT DOCUMENTS

EP 1174094 A1 1/2002
WO WO2007007331 A1 1/2007
(Continued)

OTHER PUBLICATIONS

Brånemark System® product description, Nobel BiocareTM AB (Zurich, Switzerland) (downloaded from http://www1.nobelbiocare.com/en/implants-and-abutments/products/parallelled-walled-implants/Branemark-system.aspx on Mar. 12, 2010).
(Continued)

*Primary Examiner* — Ralph Lewis
(74) *Attorney, Agent, or Firm* — Fish & Richardson P.C.

(57) ABSTRACT

Apparatus is provided that includes a dental implant having a lateral external surface. The implant is shaped so as to define a lumen therethrough having a lateral opening through the lateral external surface. The apparatus further includes a retaining element, and a delivery tube having a distal tube end. The retaining element is configured to assume (a) a first position in which the retaining element removably couples the distal tube end to the implant such that the delivery tube is in fluid communication with the lumen via the lateral opening, and (b) a second position in which the retaining element does not couple the distal tube end to the implant. Other embodiments are also described.

28 Claims, 38 Drawing Sheets

(56) References Cited

U.S. PATENT DOCUMENTS

| | | | |
|---|---|---|---|
| 3,659,881 A * | 5/1972 | Tinsley et al. | 285/249 |
| 4,021,921 A * | 5/1977 | Detaille | 433/81 |
| 4,112,944 A | 9/1978 | Williams | |
| 4,412,825 A | 11/1983 | Tokarz | |
| 4,416,629 A | 11/1983 | Mozsary et al. | |
| 4,431,416 A | 2/1984 | Niznick | |
| 4,473,353 A | 9/1984 | Greggs | |
| 4,523,910 A | 6/1985 | Makovich | |
| 4,673,353 A | 6/1987 | Nevin | |
| 4,854,872 A | 8/1989 | Detsch | |
| 4,960,381 A | 10/1990 | Niznick | |
| 5,022,857 A | 6/1991 | Matsutani et al. | |
| 5,047,030 A | 9/1991 | Draenert | |
| 5,049,125 A | 9/1991 | Accaries et al. | |
| 5,078,605 A | 1/1992 | Sutter et al. | |
| 5,188,488 A | 2/1993 | Nakayama et al. | |
| 5,261,818 A | 11/1993 | Shaw | |
| 5,284,688 A | 2/1994 | Hiatt | |
| 5,291,914 A | 3/1994 | Bares et al. | |
| 5,312,255 A | 5/1994 | Bauer | |
| 5,366,374 A | 11/1994 | Vlassis | |
| 5,456,601 A | 10/1995 | Sendax | |
| 5,481,260 A | 1/1996 | Buckler et al. | |
| 5,575,650 A | 11/1996 | Niznick et al. | |
| 5,685,716 A | 11/1997 | Linkow | |
| 5,711,315 A | 1/1998 | Jerusalmy | |
| 5,759,036 A | 6/1998 | Hinds | |
| 5,782,918 A | 7/1998 | Klardie et al. | |
| 5,795,160 A | 8/1998 | Hahn et al. | |
| 5,829,977 A | 11/1998 | Rogers et al. | |
| 5,839,899 A | 11/1998 | Robinson | |
| 5,868,572 A | 2/1999 | Lazzara et al. | |
| 5,879,161 A | 3/1999 | Lazzara | |
| 5,915,967 A | 6/1999 | Clokie | |
| 5,967,777 A | 10/1999 | Klein et al. | |
| 5,989,025 A | 11/1999 | Conley | |
| 6,068,479 A | 5/2000 | Kwan | |
| 6,159,161 A | 12/2000 | Hodosh | |
| 6,200,289 B1 | 3/2001 | Hochman et al. | |
| 6,220,860 B1 | 4/2001 | Hansson | |
| 6,270,346 B1 | 8/2001 | Grabenhofer et al. | |
| 6,273,720 B1 | 8/2001 | Spalten | |
| 6,758,673 B2 | 7/2004 | Fromovich et al. | |
| 6,827,575 B1 | 12/2004 | Jörneus | |
| 6,939,135 B2 | 9/2005 | Sapian | |
| 7,100,476 B1 | 9/2006 | Feit | |
| 7,217,130 B2 | 5/2007 | Giorno | |
| 7,297,102 B2 | 11/2007 | Smith et al. | |
| 7,300,282 B2 | 11/2007 | Sapian | |
| 7,364,430 B2 | 4/2008 | Kitamura et al. | |
| 7,396,232 B2 | 7/2008 | Fromovich et al. | |
| 7,510,397 B2 | 3/2009 | Hochman | |
| 7,934,929 B2 | 5/2011 | Better et al. | |
| 8,029,284 B2 | 10/2011 | Better et al. | |
| 8,388,343 B2 | 3/2013 | Better et al. | |
| 2003/0105469 A1 | 6/2003 | Karmon | |
| 2003/0175656 A1 | 9/2003 | Livne et al. | |
| 2003/0228556 A1 | 12/2003 | Giorno | |
| 2003/0232308 A1 | 12/2003 | Simmons | |
| 2004/0018471 A1 | 1/2004 | Giorno | |
| 2006/0020326 A9 | 1/2006 | Bolduc et al. | |
| 2006/0084034 A1 | 4/2006 | Hochman | |
| 2006/0172255 A1 | 8/2006 | Hochman et al. | |
| 2007/0055257 A1 | 3/2007 | Vaccaro et al. | |
| 2007/0162024 A1 | 7/2007 | Siemonsmeier | |
| 2007/0238068 A1 | 10/2007 | Comfortes | |
| 2008/0108011 A1 | 5/2008 | Nahlieli | |
| 2008/0182225 A1 | 7/2008 | Gordils | |
| 2008/0213729 A1 | 9/2008 | Hochman | |
| 2008/0215010 A1 | 9/2008 | Silver et al. | |
| 2008/0293010 A1 | 11/2008 | Song | |
| 2008/0319466 A1 | 12/2008 | Eder | |
| 2009/0136898 A1 | 5/2009 | Kim | |
| 2009/0186317 A1 | 7/2009 | Allon | |
| 2009/0326537 A1 | 12/2009 | Anderson | |
| 2010/0047733 A1 | 2/2010 | Nahlieli | |
| 2010/0081111 A1 | 4/2010 | Better et al. | |
| 2010/0081112 A1 | 4/2010 | Better et al. | |
| 2010/0196841 A1 | 8/2010 | Nahlieli et al. | |
| 2010/0255446 A1 | 10/2010 | Better et al. | |
| 2010/0324561 A1 | 12/2010 | Watzek et al. | |
| 2011/0165536 A1 | 7/2011 | Better et al. | |
| 2011/0212415 A1 | 9/2011 | Better et al. | |
| 2012/0094254 A1 | 4/2012 | Uchitel et al. | |

FOREIGN PATENT DOCUMENTS

| | | |
|---|---|---|
| WO | WO2007114553 A1 | 10/2007 |
| WO | WO2007080595 A3 | 4/2009 |
| WO | WO2010035270 A3 | 5/2010 |
| WO | WO2010146573 A1 | 12/2010 |

OTHER PUBLICATIONS

Chen L et al., "An 8-year retrospective study: 1,100 patients receiving 1,557 implants using the minimally invasive hydraulic sinus condensing technique," J Periodontol 76:482-491 (2005).

Flanagan D, "Important arterial supply of the mandible, control of an arterial hemorrhage, and report of a hemorrhagic incident," J Oral Implantol 29(4):165-73 (2003).

Zimmer ERA™ Mini Dental Implant System Usage Guide, Zimmer Dental (Carlsbad, CA) (Dec. 2009).

Muronoi M et al., "Simplified procedure for augmentation of the sinus floor using a haemostatic nasal balloon," British Journal of Oral & Maxillofacial Surgery 41(2):120-121 (2003).

Lee S et al., "Crestal Sinus Lift: A Minimally Invasive and Systematic Approach to Sinus Grafting," The Journal of Implant & Advanced Clinical Dentistry 1(1) (Mar. 2009).

NobelActive™ External Connection product catalog, Nobel Biocare™ AB (Zurich, Switzerland) (2007).

Pjetursson et al., "Maxillary sinus floor elevation using the (transalveolar) osteotome technique with or without grafting material. Part I: implant survival and patients' perception," Clin Oral Impl Res 20:667-676 (2009).

Riley ET et al., "The Episure syringe: a novel loss of resistance syringe for locating the epidural space," Anesth Analg. 105(4):1164-6 (Oct. 2007).

SinCrest brochure, Meta Advanced Medical Technology C.G.M. S.p.A. (Reggio Emilia, Italy) (downloaded Sep. 1, 2008).

Sinus Lift Kit brochure, Cowellmedi USA Inc. (Buena Park, CA, USA) received on Mar. 15, 2011.

Sotirakis E, "A different method for elevation of the floor of the maxillary sinus: Experimental study and reference to some cases," Mediterranean Dental Implant Congress (Athens, Greece), Scientific Programme MDIC (2004). Abstract only.

Vercellotti T, "Piezoelectric surgery in implantology: a case report—a new piezoelectric ridge expansion technique," Int J Periodontics Restorative Dent 20(4):358-65 (2000).

Vercellotti T et al., "The Piezoelectric Bony Window Osteotomy and Sinus Membrane Elevation: Introduction of a New Technique for Simplification of the Sinus Augmentation Procedure," Int J Periodontics Restorative Dent 21(6):561-7 (2001).

Zimmer Tapered Screw-Vent® Implant System product catalog, Zimmer Dental Inc. (Carlsbad, CA, USA) (2008).

Zimmer Tapered Screw-Vent® Implant System Product Catalog, Zimmer Dental Inc. (Carlsbad, CA, USA) (Mar. 2009).

Zimmer Spline® Implant System Product Catalog, Zimmer Dental Inc. (Carlsbad, CA, USA) (Feb. 2007).

Zimmer SwissPlus® Implant System Product Catalog, Zimmer Dental Inc. (Carlsbad, CA, USA) (Jan. 2007).

Zimmer ERA™ Mini Dental Implant System Product Catalog, Zimmer Dental Inc. (Carlsbad, CA, USA) (Feb. 2010).

Fritz ME et al. The use of Guided Bone Regeneration to fill Large Mandibular Defects in Monkeys, A Pilot Study, JOMI, pp. 644-652, Jun. 1994.

Bui DX, Guided Bone Regeneration downloaded from http://www.drbui.com/artgbr.html Dec. 19, 2011.

(56) References Cited

OTHER PUBLICATIONS

Kawana (Kawana) et al. Acquisition of Bone Structure in Drilling process using Cutting force Estimation, pp. 393-398, Nov. 2010, Yokohama, Japan.
An Office Action dated Jun. 1, 2011, which issued during the prosecution of U.S. Appl. No. 12/240,353.
An Office Action dated Oct. 1, 2010, which issued during the prosecution of U.S. Appl. No. 12/240,353.
An Office Action dated Apr. 11, 2011, which issued during the prosecution of U.S. Appl. No. 12/485,199.
An Office Action dated Jun. 27, 2011, which issued during the prosecution of U.S. Appl. No. 12/485,199.
An Office Action dated Dec. 27, 2011, which issued during the prosecution of U.S. Appl. No. 12/661,795.
U.S. Appl. No. 60/619,542, filed Oct. 15, 2004.
An International Search Report dated Mar. 23, 2010, which issued during the prosecution of Applicant's PCT/IL2009/000931.
An International Preliminary Report on Patentability dated Mar. 29, 2011, which issued during the prosecution of Applicant's PCT/IL2009/000931.
An International Search Report dated Jul. 15, 2010, which issued during the prosecution of Applicant's PCT/IL2010/000252.
An International Preliminary Report on Patentability dated Dec. 16, 2011, which issued during the prosecution of Applicant's PCT/IL2010/000252.
An Office Action dated Mar. 15, 2013, which issued during the prosecution of U.S. Appl. No. 13/196,632.
An Office Action dated Mar. 19, 2013, which issued during the prosecution of U.S. Appl. No. 13/409,631.
An Office Action dated Mar. 29, 2013, which issued during the prosecution of U.S. Appl. No. 13/228,564.
An Office Action dated Oct. 16, 2012, which issued during the prosecution of U.S. Appl. No. 12/661,795.
English translation of Chinese Office Action mailed Jul. 30, 2013, which issued in Chinese Application No. 200980147751.3.
An Office Action dated Jun. 20, 2013, which issued during the prosecution of U.S. Appl. No. 13/196,632.
An Office Action dated Jun. 26, 2013, which issued during the prosecution of U.S. Appl. No. 13/409,631.
An Office Action dated Jun. 26, 2013, which issued during the prosecution of U.S. Appl. No. 13/760,206.
European Search Report issued Nov. 13, 2013 in EP Application No. 10 78 9099.

* cited by examiner

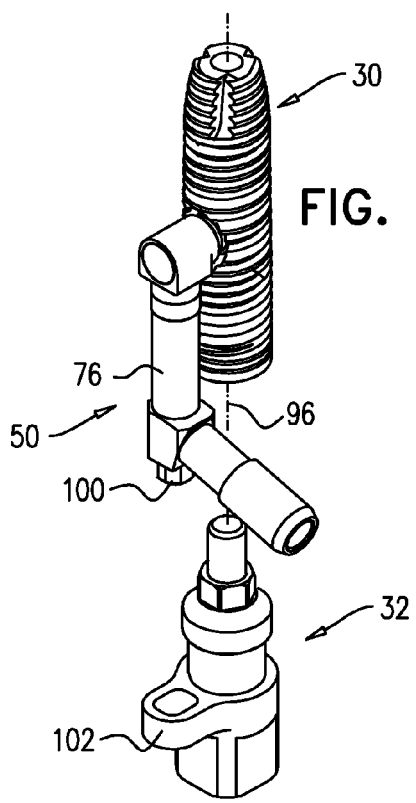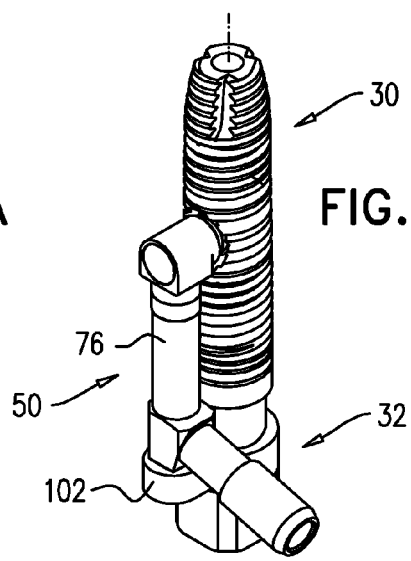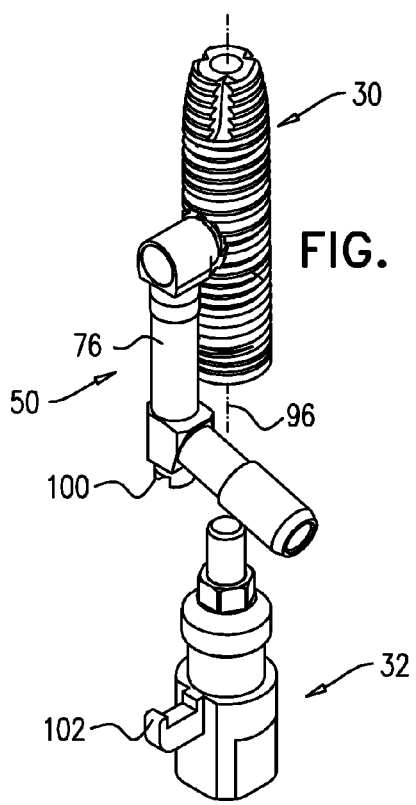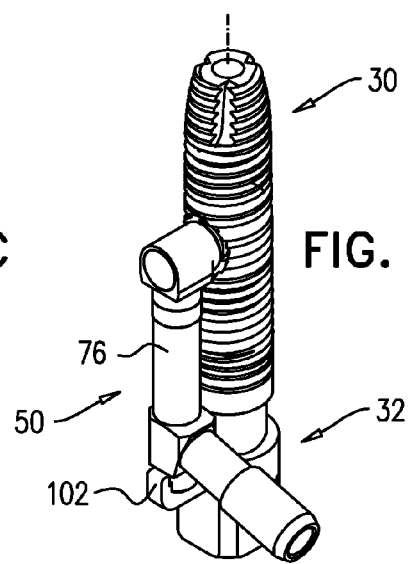

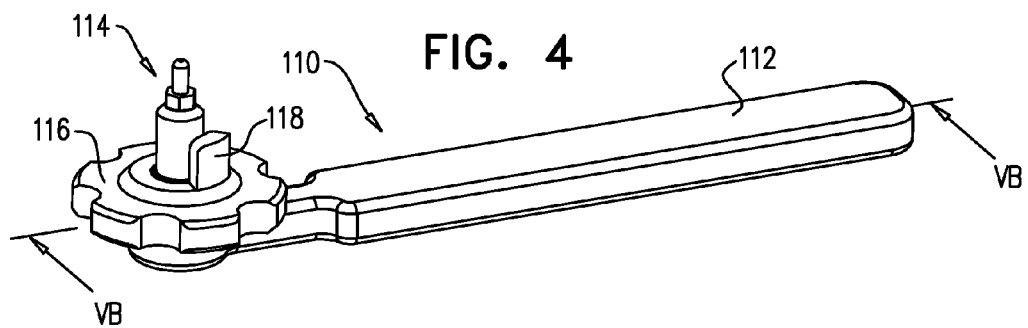
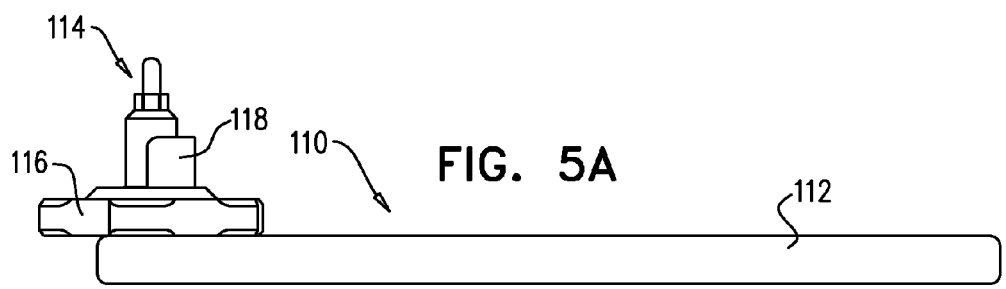
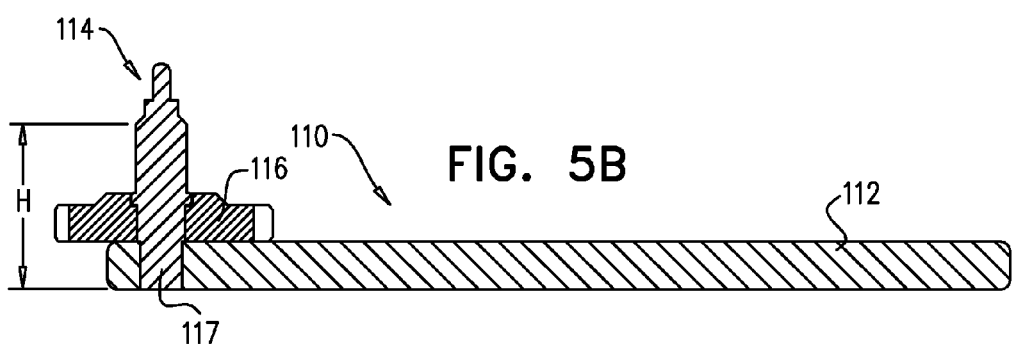

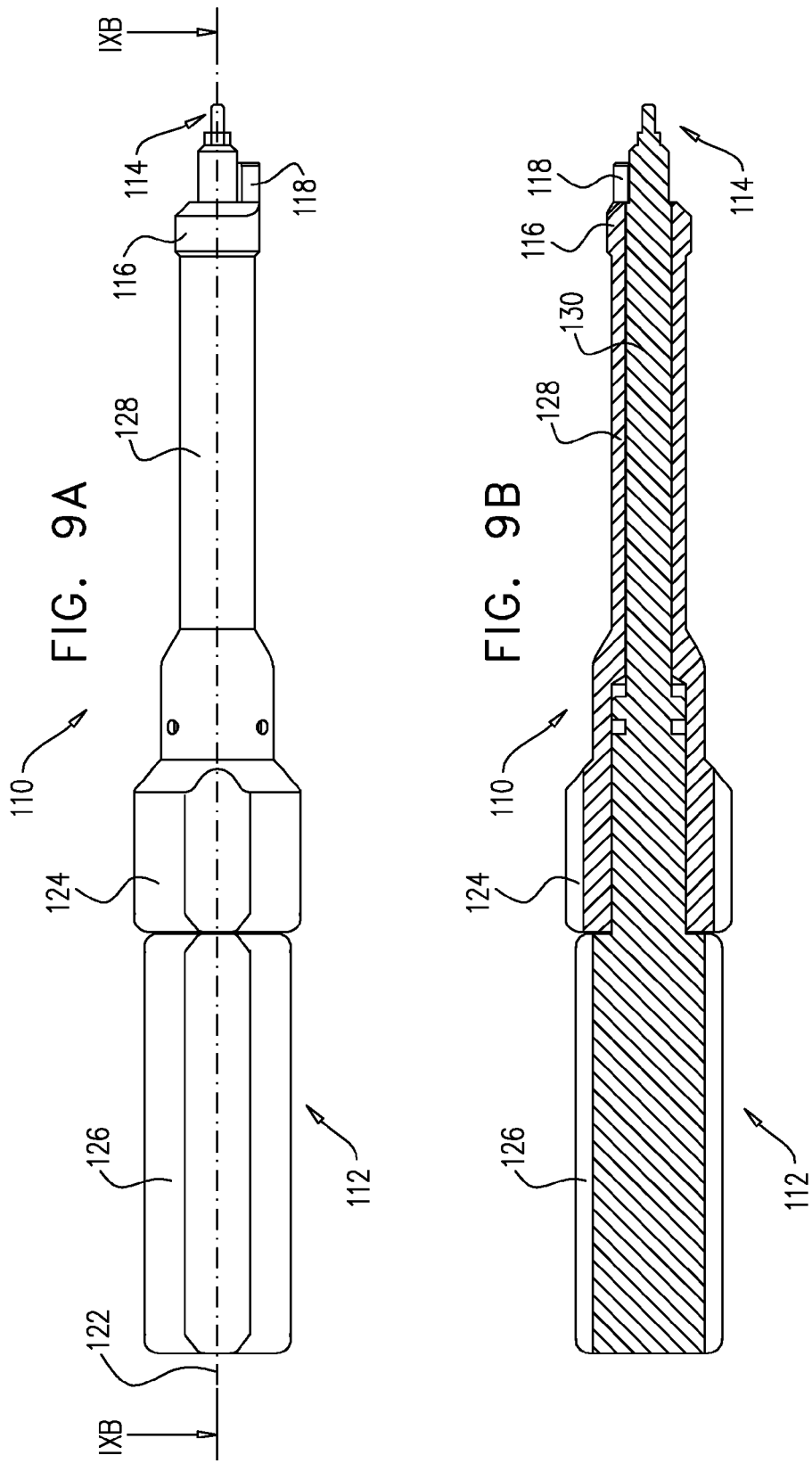

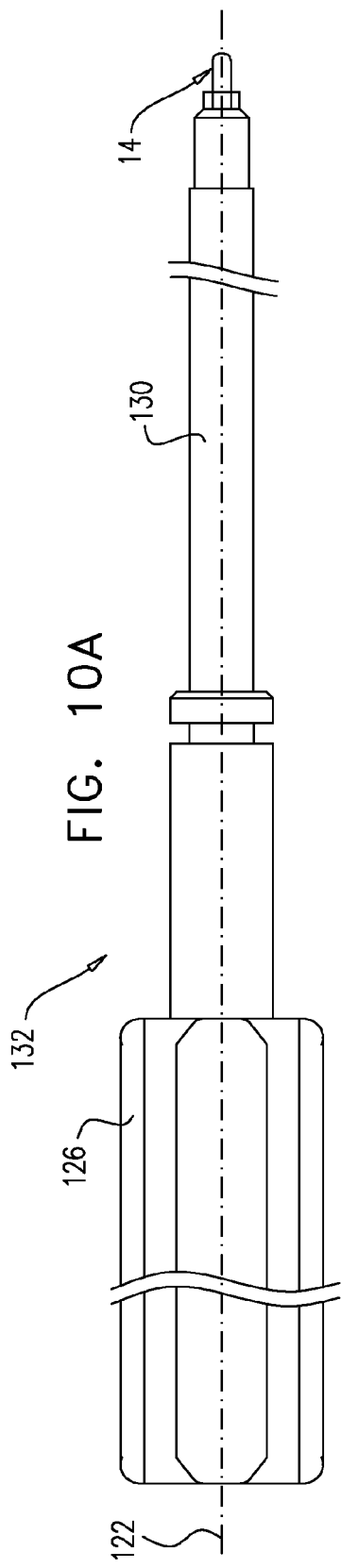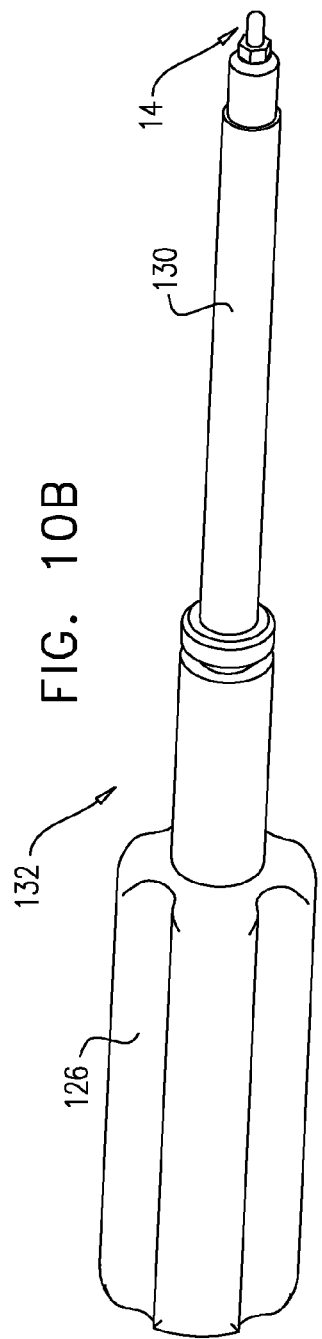

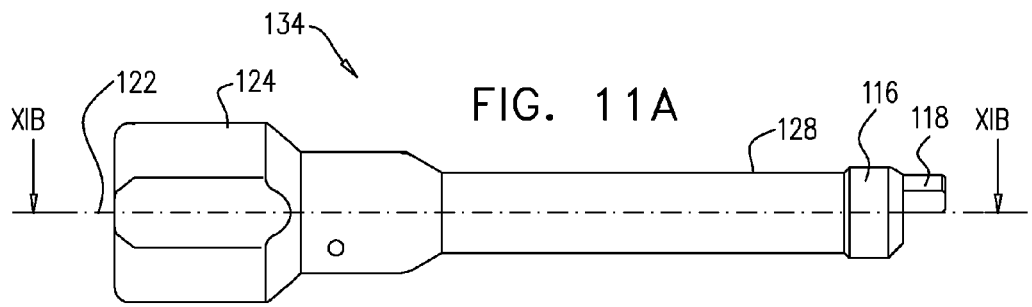
FIG. 11A
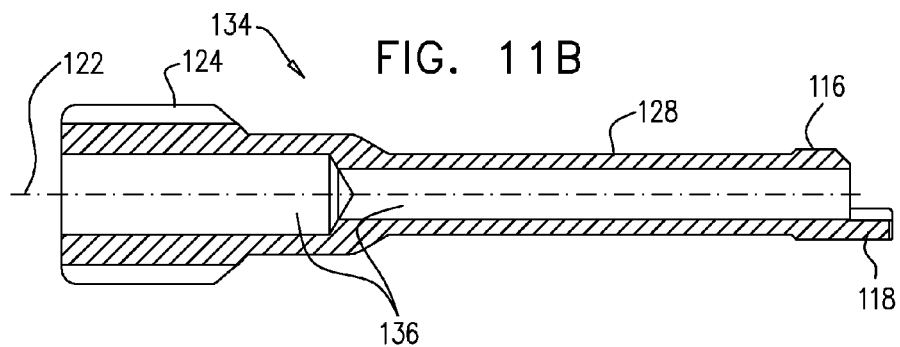
FIG. 11B
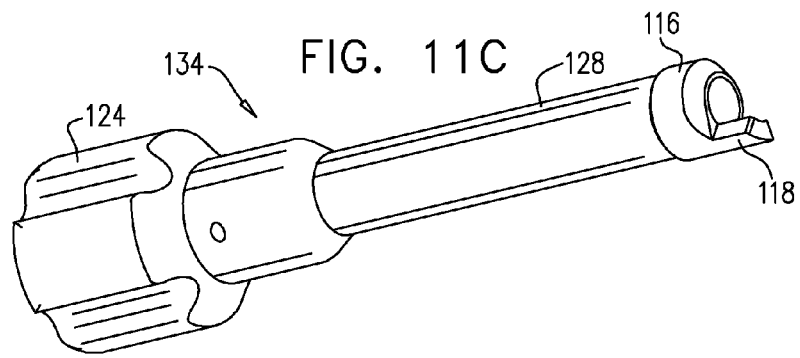
FIG. 11C
FIG. 11D
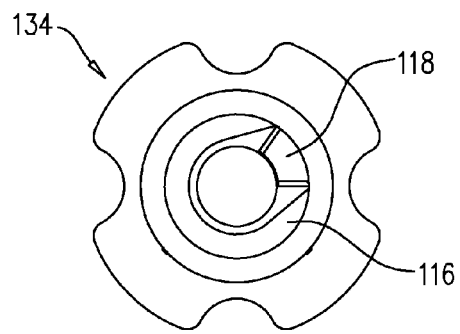

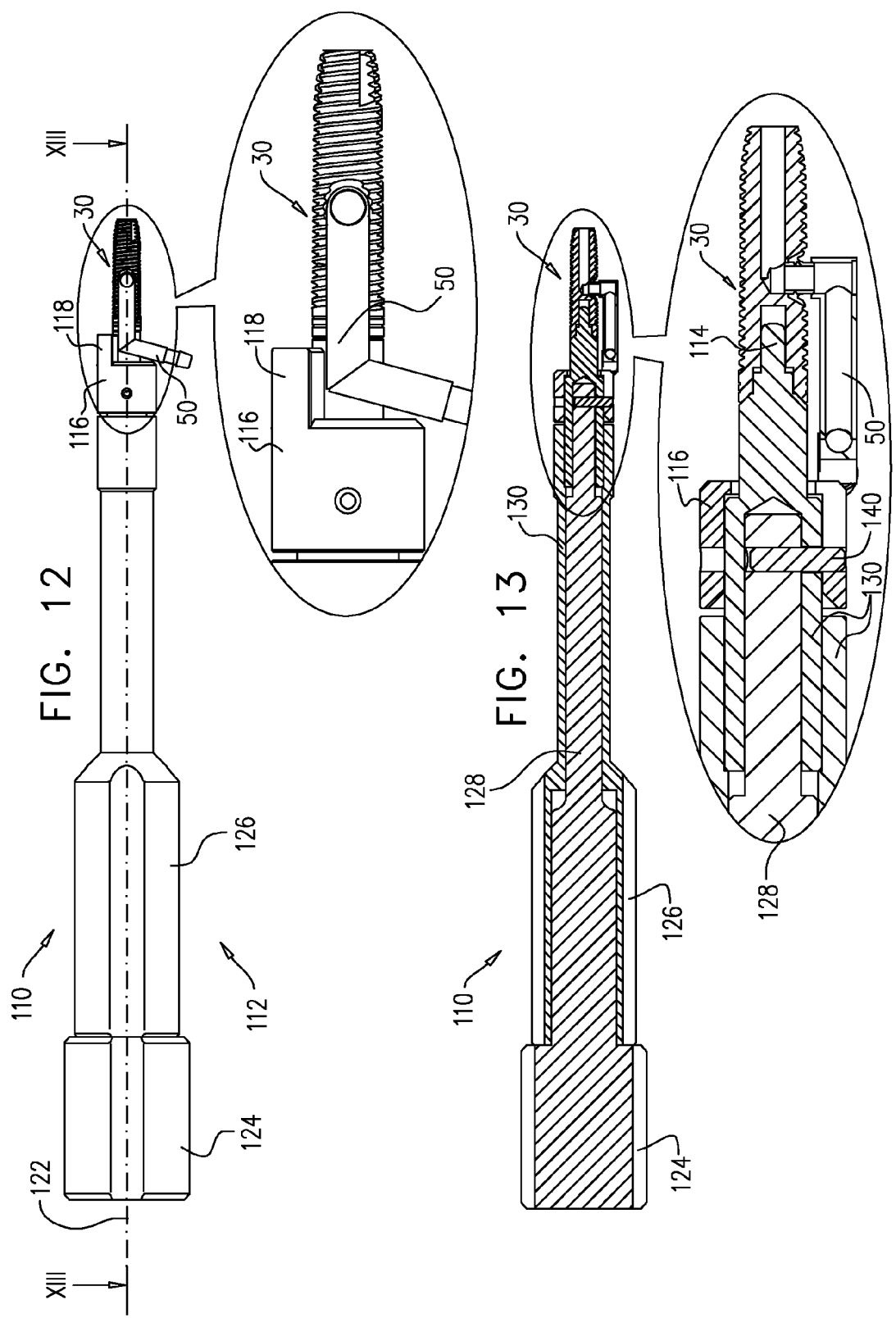

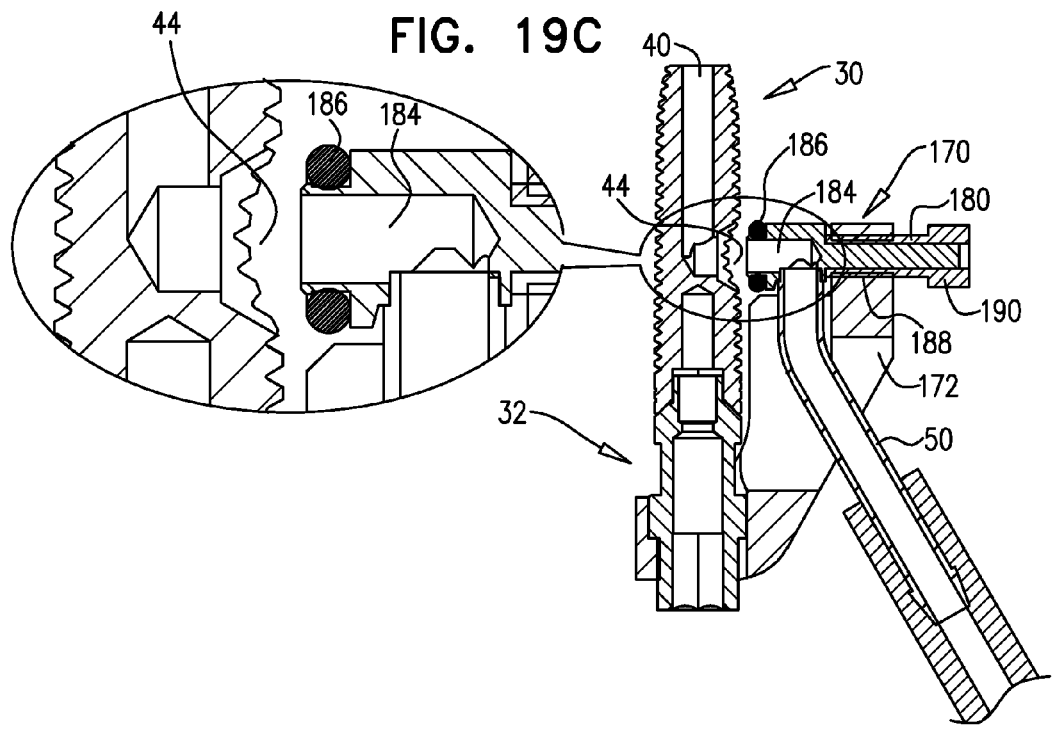
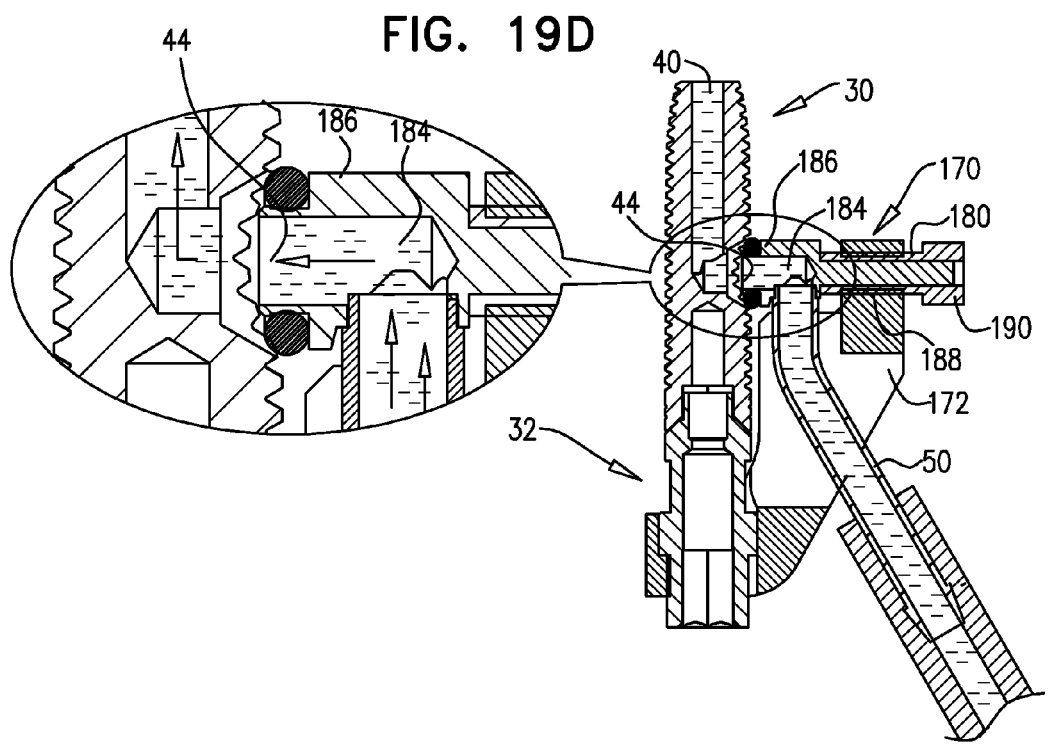

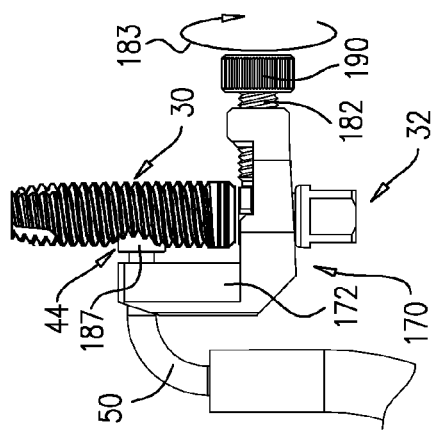
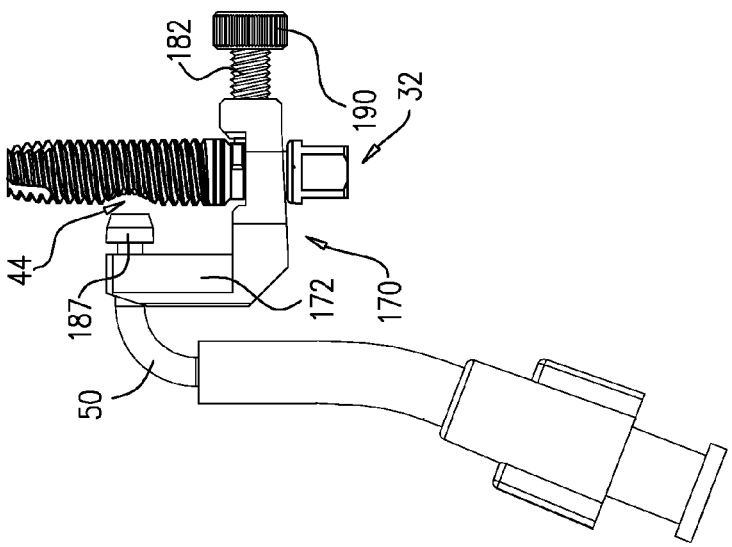
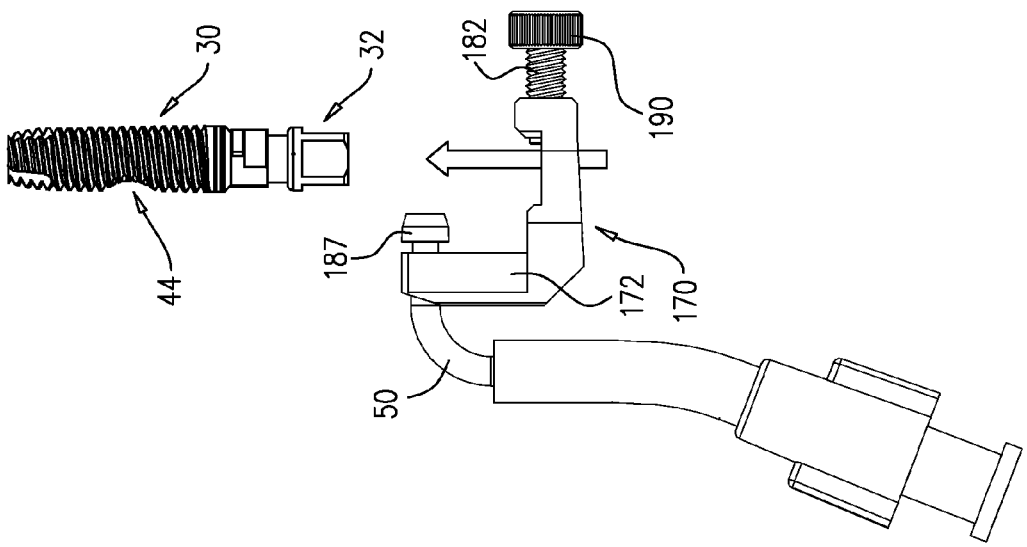

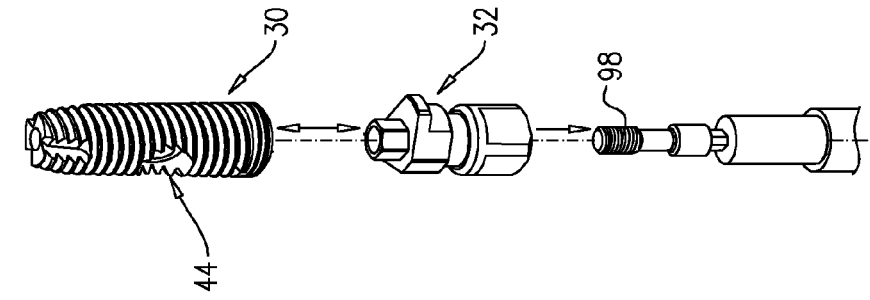
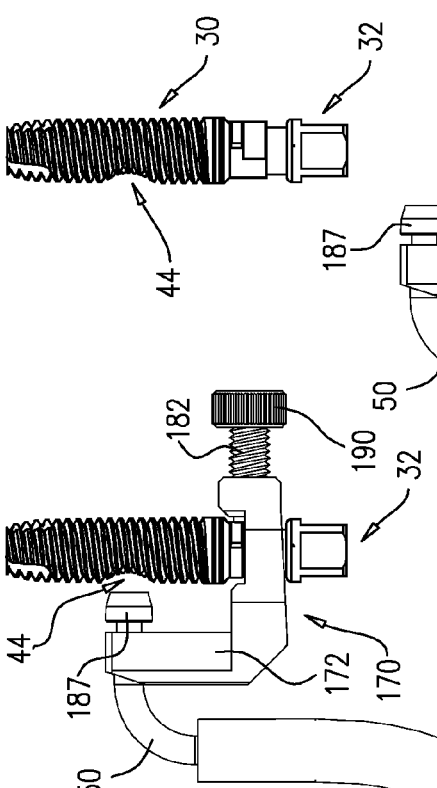
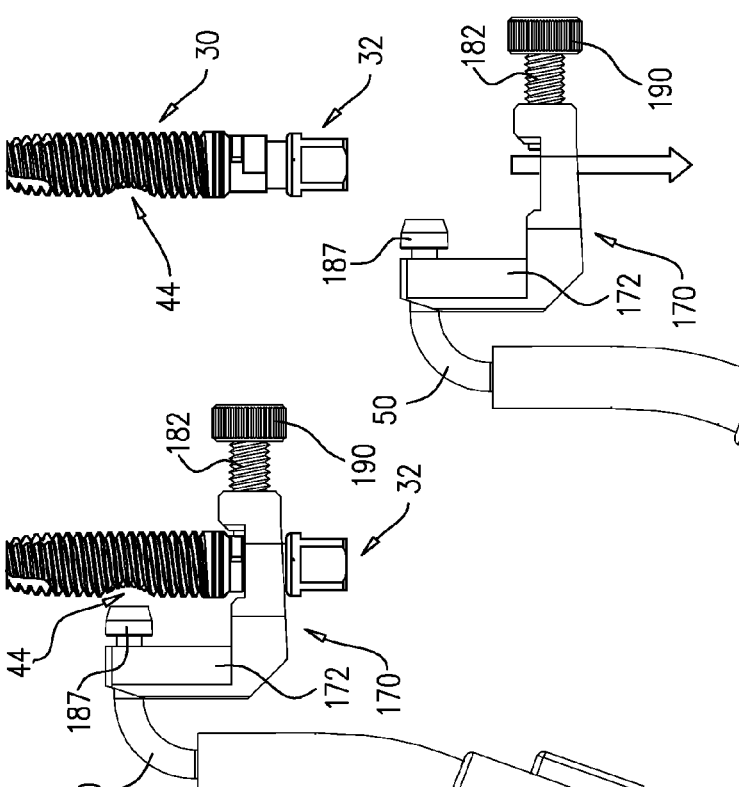
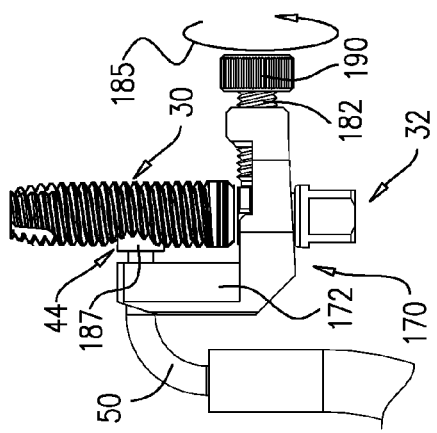

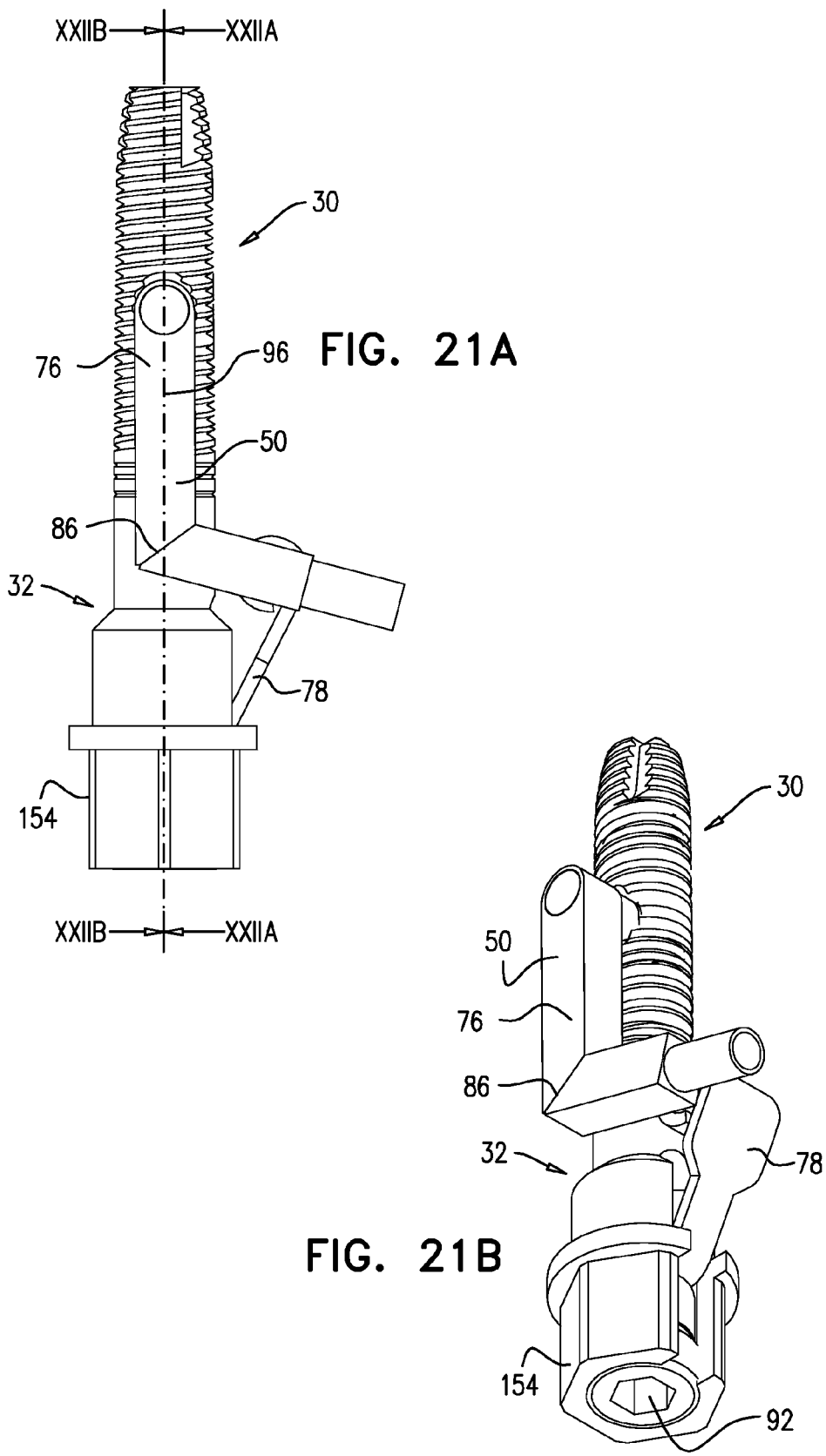

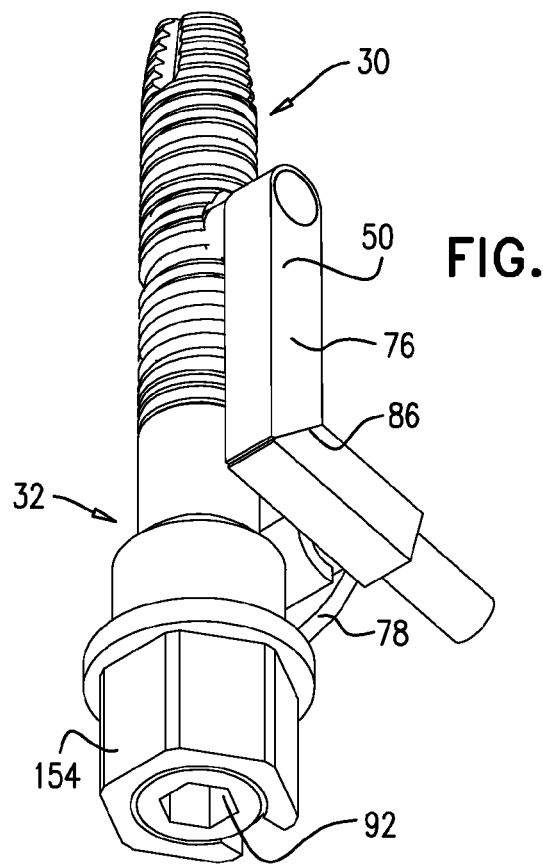
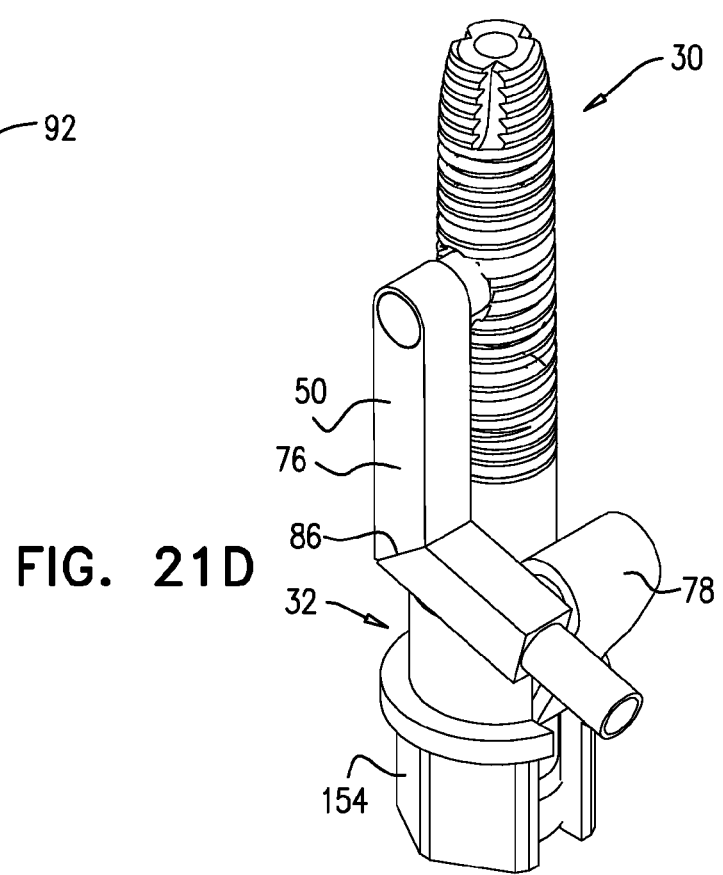
FIG. 21C
FIG. 21D

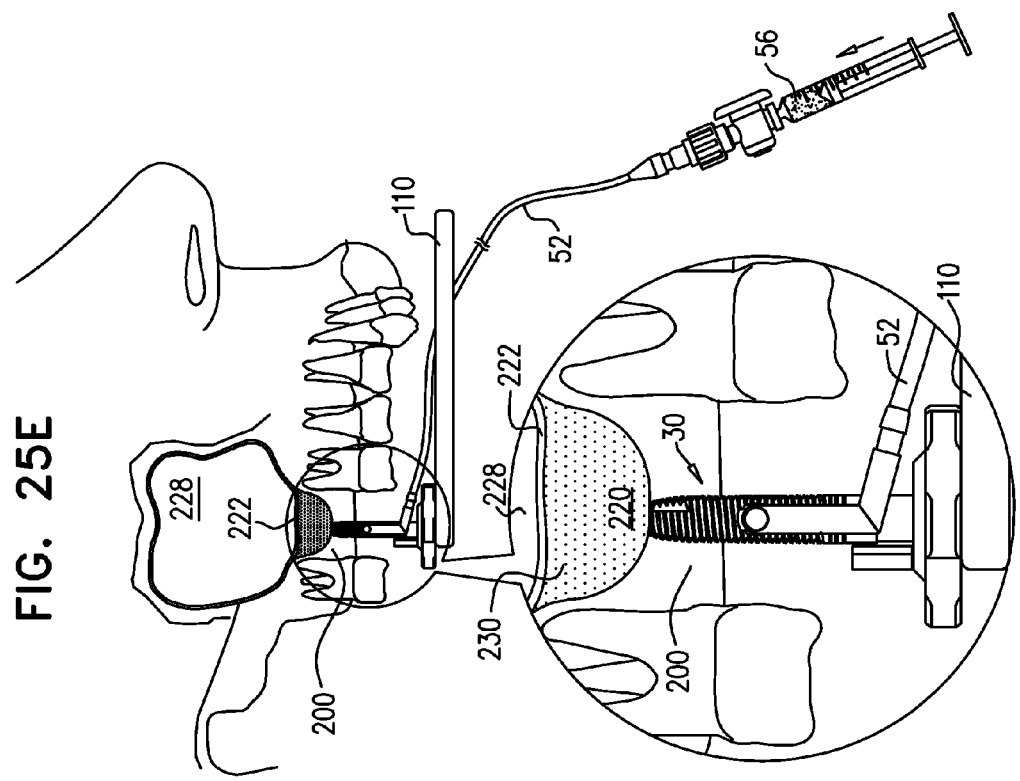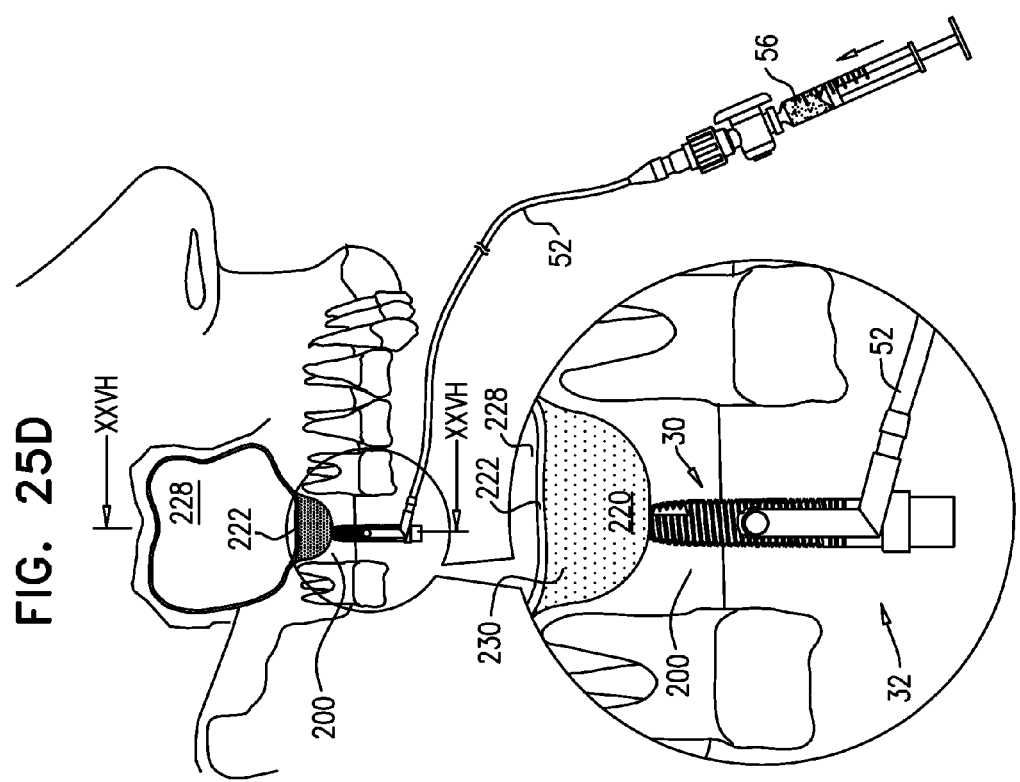

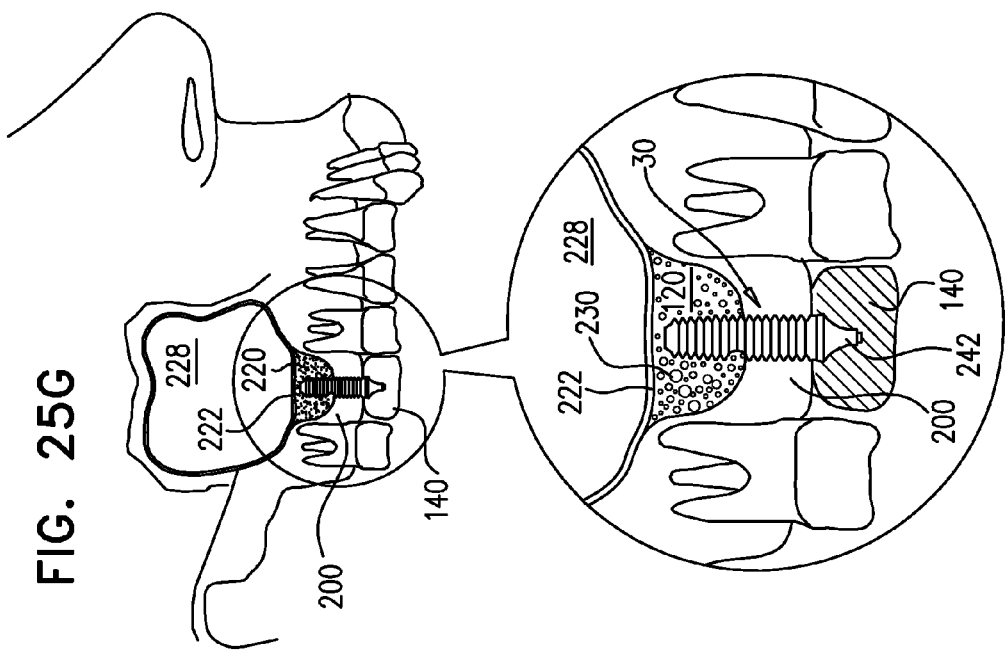
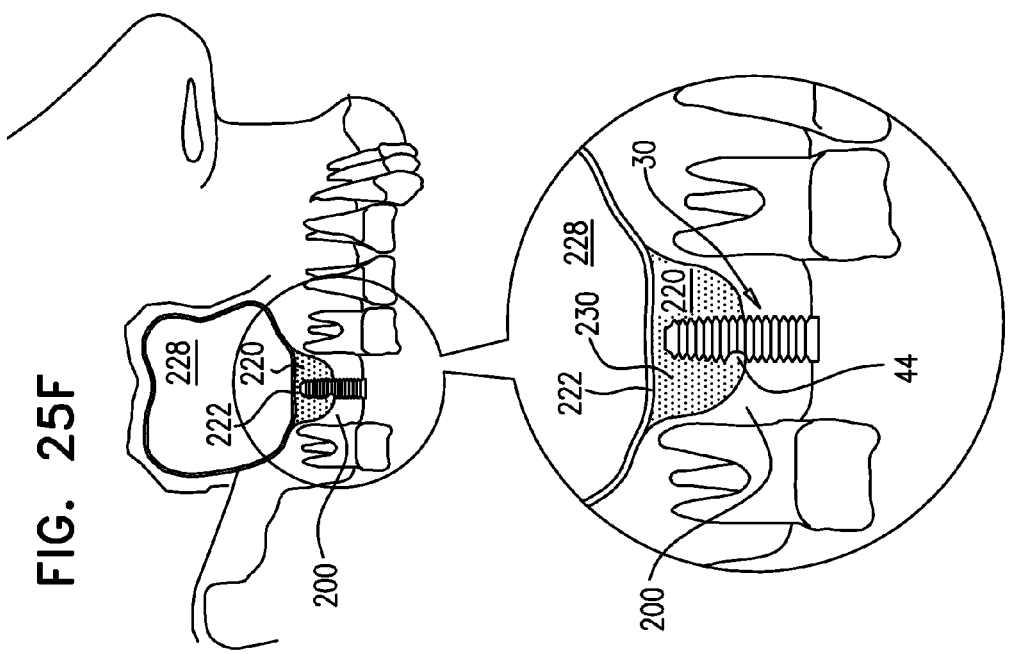

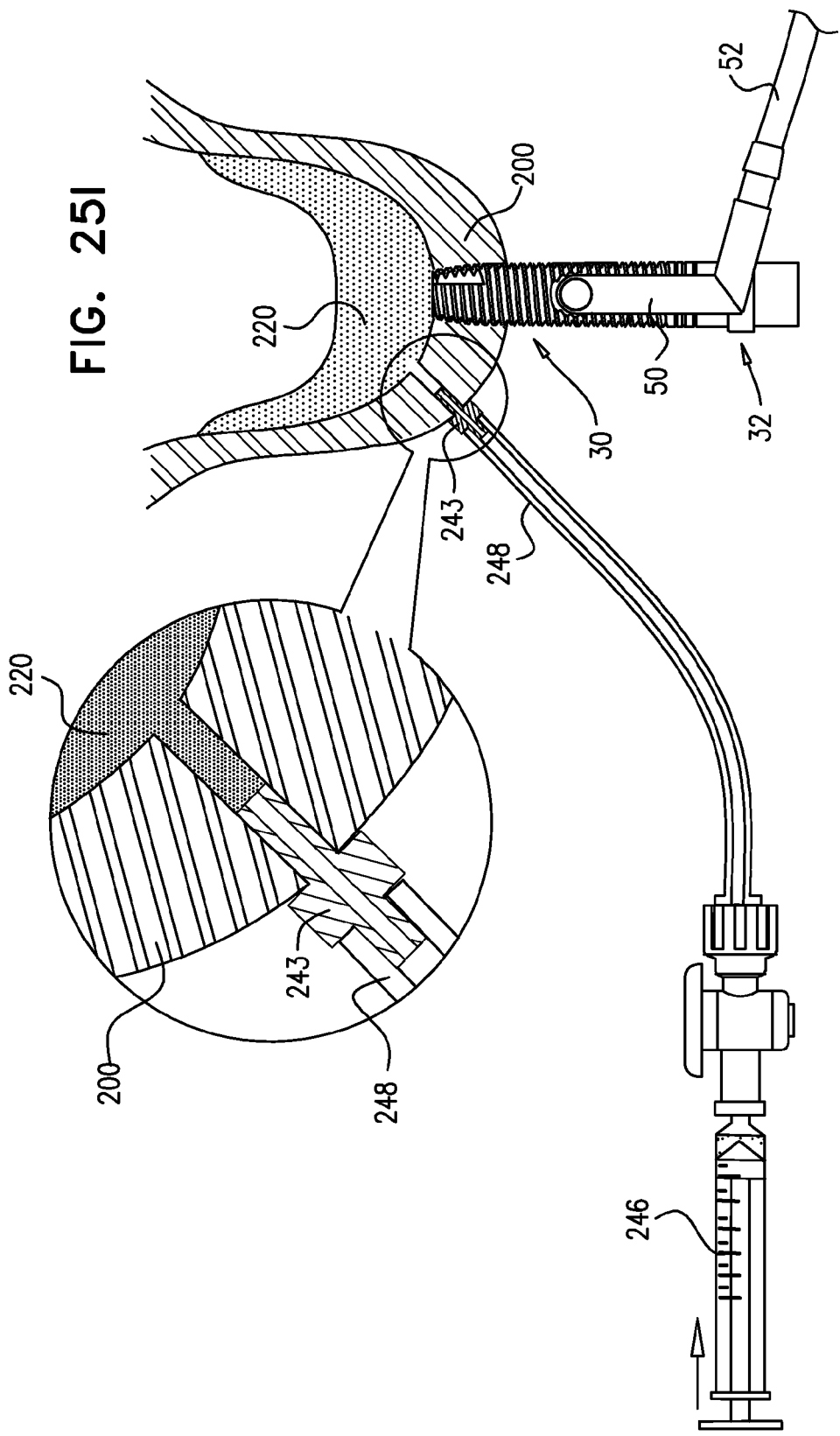

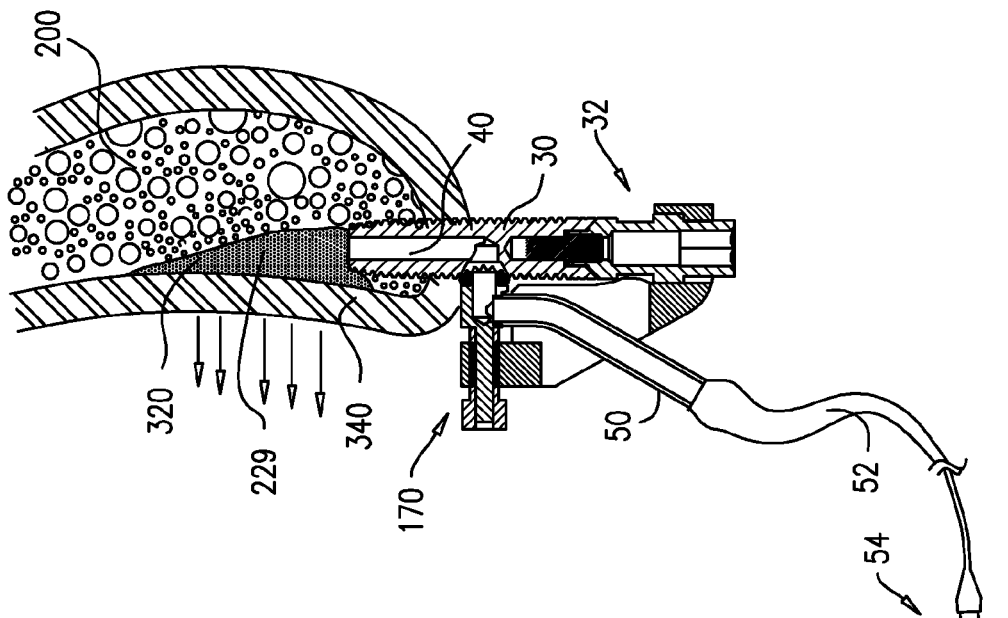
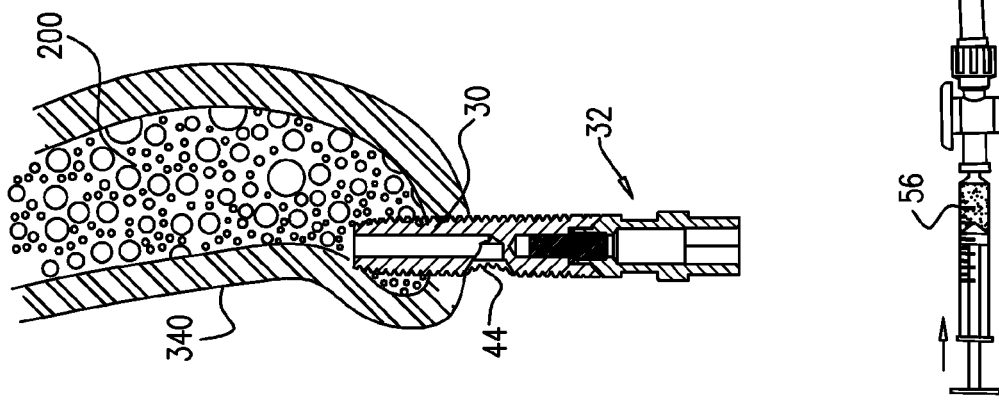
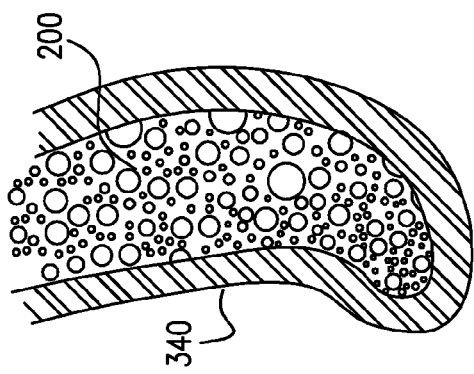

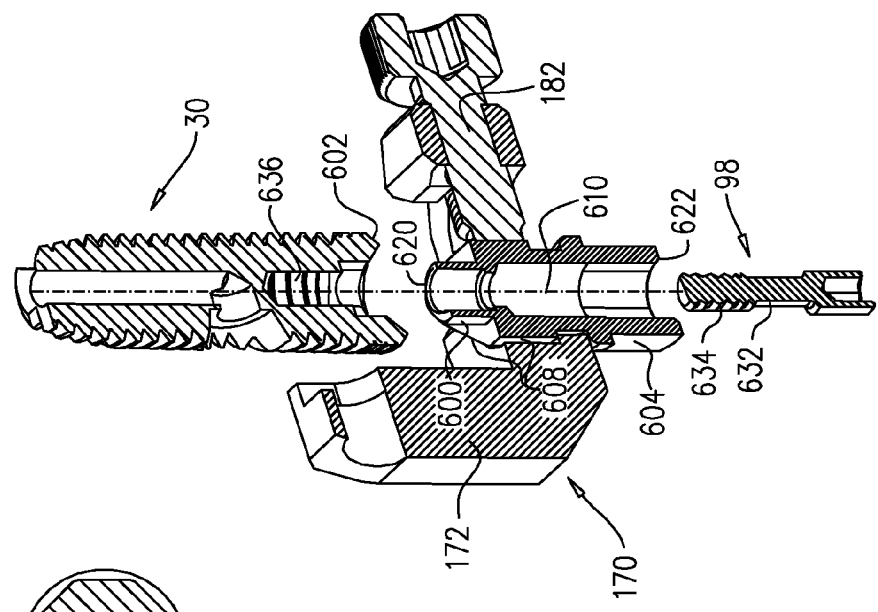
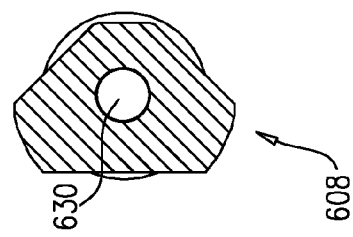
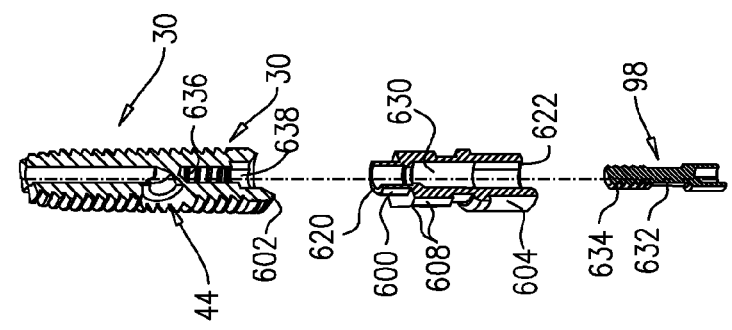
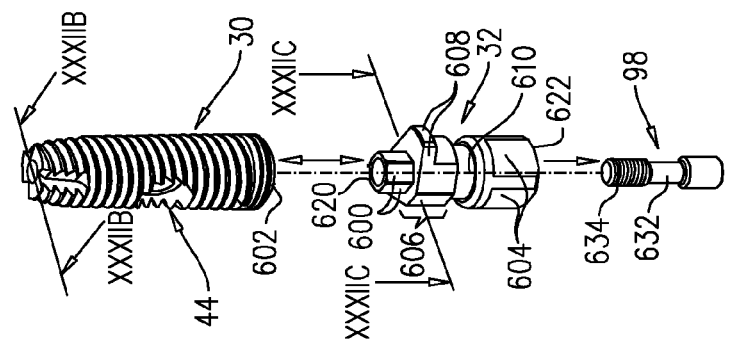

IMPLANTS, TOOLS, AND METHODS FOR SINUS LIFT AND LATERAL RIDGE AUGMENTATION

CROSS-REFERENCE TO RELATED APPLICATIONS

The present invention is:

(a) a continuation-in-part of International Application PCT/IL2010/000252, filed Mar. 24, 2010, which is a continuation-in-part of (i) U.S. application Ser. No. 12/485,199, filed Jun. 16, 2009, now U.S. Pat. No. 8,029,284, and (ii) International Application PCT/IL2009/000931, filed Sep. 29, 2009; and (b) a continuation-in-part of U.S. application Ser. No. 13/040,440, filed Mar. 4, 2011, now U.S. Pat. No. 8,356,994, which is a continuation of U.S. application Ser. No. 12/240,353, filed Sep. 29, 2008, now U.S. Pat. No. 7,934,929.

All of the above-mentioned applications are assigned to the assignee of the present application and are incorporated herein by reference.

FIELD OF THE APPLICATION

The present invention relates generally to dental implants and implantation methods, and specifically to minimally-invasive implants and implantation methods for sinus lift and lateral ridge augmentation procedures.

BACKGROUND OF THE APPLICATION

Osseointegrated dental implants are typically metallic or ceramic screws that are placed in the jawbone for supporting artificial teeth after the loss of natural teeth. Replacement of the maxillary teeth is often a challenging surgical procedure when the remaining maxillary bone has insufficient height to support the implant. One surgical technique for augmenting the maxillary bone includes injecting a regenerative material, such as autogeneic, allogeneic, xenogeneic, or synthetic bone graft, into the vicinity of the maxillary bone. The regenerative material forms additional bone mass that integrates with the existing maxillary bone, providing the necessary alveolar height to support the implant.

Bone augmentation procedures are often surgically difficult to perform, and are associated with complications, including infection of the maxillary sinus. The top of the maxillary alveolar ridge forms the floor of the maxillary sinus, and is covered by a thin membrane known as the Schneiderian or subantral membrane. In one surgical procedure, known as a closed or internal sinus lift or elevation procedure, the surgeon drills a bore through the maxillary alveolar ridge from the oral cavity at the desired location of the implant. The bore penetrates the ridge to below the Schneiderian membrane. The surgeon injects the regenerative material through the bore to below the membrane, forming a cavity defined by the top of the ridge and the bottom of the membrane, which cavity occupies a portion of the space initially occupied by the maxillary sinus.

To prevent potentially serious complications, the surgeon must be careful not to perforate the Schneiderian membrane. This is often difficult, because of the delicacy of the membrane, and the restricted access afforded by the closed approach.

SUMMARY OF APPLICATIONS

Some embodiments of the present invention provide a self-tapping osseointegrated dental implant and minimally-invasive closed sinus lift techniques for augmenting the maxillary alveolar ridge while reducing the risk of perforating the Schneiderian membrane and of infection. The dental implant is shaped so as to define a lumen therethrough having a distal opening through a distal external surface of a distal portion of the implant. During an implantation procedure, a surgeon advances the implant into a bore in the ridge until the distal implant end forms an opening through the top of the ridge to below the Schneiderian membrane, thereby bringing the distal opening into fluid communication with a surface of the membrane facing the ridge.

The surgeon gently lifts and separates the membrane from the top of the ridge by injecting a fluid, such as saline solution, via the lumen, so as to form a cavity below the membrane between the ridge and the membrane. For some applications, the surgeon drains the fluid and injects a regenerative material, such as liquid or gel bone graft, via the lumen into the cavity. Alternatively, the surgeon does not drain the fluid, or drains the fluid but does not inject the regenerative material. The surgeon further screws the implant into the cavity. After bone grows in the cavity, a dental appliance, such as a crown, is coupled to the implant.

For some applications, a proximal end of the lumen of the implant has a lateral opening through a lateral external surface of the implant, and is not open to a proximal external surface of the implant within 2 mm of the proximal-most part of the implant. The implant typically is permanently closed within 3 mm of the proximal-most part. During the implantation procedure, the additional screwing of the implant into the regenerative material advances the lateral external surface of the implant until the lateral opening is positioned entirely within the bore in the ridge and/or within the cavity between the ridge and the membrane. Such positioning of both ends of the lumen within bone (current or future) substantially reduces the risk of infection, because the proximal end of the implant that is exposed to the oral cavity or gingiva is permanently closed.

For some applications, a delivery tube is coupled to the lumen via the lateral opening. After injecting the fluid, and, optionally, the regenerative material, into the cavity from the delivery tube via the lumen, the surgeon decouples the delivery tube from the implant before further rotating the implant to bring the lateral opening entirely within the bore in the ridge and/or the cavity.

For some applications, a retaining element is provided, which is configured to assume a first position in which the retaining element couples a distal end of the delivery tube to the implant, and a second position in which the retaining element does not couple the distal tube end to the implant. Typically, a sealing element is configured to removably sealingly couple the delivery tube to the implant. For some applications, a distal portion of the sealing element is conical. Alternatively or additionally, the distal tube end is embedded in the sealing element.

For some applications, an applicator is provided, which is removably coupled to a proximal implant end of the implant. The retaining element is coupled to the delivery tube and shaped so as to be removably couplable to the proximal implant end via the applicator, such that the retaining element removably couples the distal tube end to the implant when the retaining element is removably coupled to the proximal end via the applicator and is in the first position. For some applications, the retaining element comprises a retaining element body, a portion of which is configured to be disposed alongside the implant, from the applicator to the lateral opening of the implant. For some applications, the retaining element further comprises a shaft, which is configured such that rotation of the shaft brings the distal tube end into contact with the lateral opening of the implant, to sealingly couple the distal tube end to the lateral opening. The retaining element may be configured such that when the retaining element is in the first position, the shaft and the distal tube end are positioned at circumferentially opposite sides of the implant. Typically, the shaft is oriented such that a longitudinal axis thereof forms an angle of 90 degrees with a longitudinal axis of the implant. Optionally, an external surface of a portion of the shaft is shaped so as to define a screw thread, which passes through a lumen of the retaining element body that is shaped so as to define a corresponding screw thread.

For some applications, a minimally-invasive closed lateral ridge augmentation surgical procedure is provided for implanting a dental implant. The procedure is typically employed when a patient's maxillary or mandibular alveolar ridge lacks sufficient bone width to support a dental implant. A dental implant is shaped so as to define a lumen therethrough having at least one distal opening through a distal external surface, and a lateral opening through a lateral external surface of the implant. The surgeon forms a bore in bone of an alveolar ridge, and inserts the implement into the bore at least until the distal opening comes into fluid communication with periosteal tissue covering a lateral surface of the bone. Optionally, the surgeon attaches a retaining element to the implant, or to an applicator coupled to the implant, and causes the retaining implant to removably sealingly couple a distal end of a delivery tube to the lateral opening. The surgeon delaminates the periosteal tissue from the bone by injecting a fluid through the lumen to form a cavity between the bone and the periosteal tissue. After delaminating the periosteal tissue, the surgeon optionally injects a regenerative material into the cavity via the lumen.

There is therefore provided, in accordance with an application of the present invention, apparatus including:

a dental implant having a lateral external surface, the implant being shaped so as to define a lumen therethrough having a lateral opening through the lateral external surface;

a delivery tube having a distal tube end; and a retaining element, which is configured to assume (a) a first position in which the retaining element removably couples the distal tube end to the implant such that the delivery tube is in fluid communication with the lumen via the lateral opening, and (b) a second position in which the retaining element does not couple the distal tube end to the implant.

For some applications, the apparatus further includes a sealing element, which is configured to removably sealingly couple the delivery tube to the implant when the retaining element is in the first position. For example, the sealing element may include an element selected from the group consisting of: an o-ring and a gasket. For some applications, a distal portion of the sealing element is conical. For some applications, the distal tube end is embedded in the sealing element.

For some applications, at least a portion of the retaining element includes a rigid material.

For some applications, at least a portion of the retaining element is disposed at least 1.5 cm from the lateral opening when the retaining element is in the first position.

For some applications, the retaining element is removably coupled to a proximal implant end of the implant, and coupled to the delivery tube.

For some applications, the apparatus further includes an applicator, which is removably coupled to a proximal implant end of the implant, and the retaining element is coupled to the delivery tube and shaped so as to be removably couplable to the proximal implant end via the applicator, such that the retaining element removably couples the distal tube end to the implant when the retaining element is removably coupled to the proximal end via the applicator and is in the first position.

For some applications, the retaining element includes a retaining element body, a portion of which is configured to be disposed alongside the implant, from the applicator to the lateral opening of the implant, when the retaining element is removably coupled to the proximal implant end via the applicator. For some applications, the retaining element further includes a shaft, which is configured such that rotation of the shaft brings the distal tube end into contact with the lateral opening of the implant, to sealingly couple the distal tube end to the lateral opening. For some applications, the retaining element is configured such that the shaft and the distal tube end are positioned at circumferentially opposite sides of the implant, when the retaining element is coupled to the proximal implant end via the applicator, and at least when the retaining element is in the first position. For some applications, the retaining element is configured such that the shaft and the distal tube end are positioned at a same circumferential side of the implant, when the retaining element is coupled to the proximal implant end via the applicator, and at least when the retaining element is in the first position. For some applications, the shaft is oriented such that a longitudinal axis thereof forms an angle of 90 degrees with a longitudinal axis of the implant, when the retaining element is coupled to the proximal implant end via the applicator, and at least when the retaining element is in the first position. For some applications, an external surface of a portion of the shaft is shaped so as to define a screw thread, which passes through a lumen of the retaining element body that is shaped so as to define a corresponding screw thread.

For some applications, the retaining element further includes a shaft, a first end of which serves as the distal tube end, which shaft is configured to sealingly couple the distal tube end to the lateral opening of the implant. For some applications, the shaft is configured such that rotation of a portion thereof brings the distal tube end into contact with the lateral opening of the implant.

For some applications, the retaining element is shaped so as to be removably couplable to the applicator, such that the retaining element removably couples the distal tube end to the implant when the applicator is removably coupled to the proximal implant end, and the retaining element is removably coupled to the applicator in the first position. For some applications, the applicator is shaped so as to define a longitudinal portion that is shaped so as to define an external surface that is rotationally asymmetric. For some applications, the retaining element is shaped such that the rotationally-asymmetric surface of the applicator constrains a rotational orientation of the retaining element to a single rotational orientation with respect to the applicator, and rotationally aligns the distal tube end with the lateral opening of the implant.

For some applications, the retaining element is fixed to the applicator.

For some applications, the applicator further includes a spring, which is configured to apply a force that separates the distal tube end from the implant when the retaining element assumes the second position.

For some applications, the lumen is not open to a proximal external surface of the implant within 2 mm of a proximal-most part of the implant. For some applications, the implant has a distal implant portion that extends from a distal implant end along up to 50% of a longitudinal length of the implant, and the lumen has at least one distal opening through a distal external surface of the distal implant portion. For some applications, the implant is shaped such that the lumen defines exactly one lateral opening through the lateral external surface.

For some applications, the apparatus further includes an applicator, which is removably coupled to a proximal implant end of the implant.

For some applications, the distal tube end is not welded to the implant.

For some applications, the retaining element is configured to rotationally align the distal tube end with the lateral opening when the retaining element assumes the first position.

For some applications, when the delivery tube is removably coupled to the implant, a portion of the delivery tube runs alongside the implant such that a greatest distance between a longitudinal axis of the implant and a surface of the portion of the delivery tube farthest from the longitudinal axis is less than 7 mm.

For some applications, a proximal end of the implant is shaped so as to define an abutment-coupling surface. For some applications, the apparatus further includes an abutment, which is configured to be coupled to the abutment-coupling surface. Alternatively, for some applications, the implant is shaped so as to define an integrated abutment.

There is further provided, in accordance with an application of the present invention, apparatus including:
a dental implant having a lateral external surface, the implant being shaped so as to define a lumen therethrough having a lateral opening through the lateral external surface;
a delivery tube having a distal tube end, which distal tube end is removably coupled to the implant such that the delivery tube is in fluid communication with the lumen via the lateral opening; and
a fixing element and a fixing element receptor, which are configured to be temporarily coupled together so as to prevent decoupling of the delivery tube from the implant.

For some applications, the apparatus further includes an applicator, which is removably coupled to a proximal implant end of the implant, and which is shaped so as to define the fixing element receptor. For some applications, the applicator is configured such that removal of the applicator from the implant frees the fixing element from the fixing element receptor.

For some applications, the delivery tube includes the fixing element.

For some applications, the fixing element and the fixing element receptor are configured, when temporarily coupled together, to prevent rotation of the delivery tube with respect to the implant.

For some applications, the fixing element is shaped so as to define a fixing pin, and the fixing element receptor is shaped so as to define a receptor hole.

For some applications, the fixing element is shaped so as to define a shape selected from the group consisting of: a slot and a groove, and the fixing element receptor is shaped so as to define a corresponding coupling surface that fixes the fixing element to the fixing element receptor.

For some applications, the distal tube end is removably coupled to the implant by being welded to the implant.

There is still further provided, in accordance with an application of the present invention, apparatus including:
a dental implant having a lateral external surface, the implant being shaped so as to define a lumen therethrough having a lateral opening through the lateral external surface; and
a delivery tube having a distal tube end, which distal tube end is removably coupled to the implant at a first interface, such that the delivery tube is in fluid communication with the lumen via the lateral opening,
wherein the delivery tube is removably coupled to the implant at a second interface remote from the first interface, so as to prevent movement of the distal tube end with respect to the implant.

For some applications, the delivery tube is directly removably coupled to the implant at the second interface. Alternatively, the delivery tube is indirectly removably coupled to the implant at the second interface. For some applications, the apparatus further includes an applicator, which (a) is removably coupled to a proximal implant end of the implant at the second interface, and (b) indirectly removably couples the delivery tube to the implant.

For some applications, the delivery tube is removably coupled to the implant at the second interface, so as to prevent rotation of the distal tube end with respect to the implant.

For some applications, the distal tube end is removably coupled to the implant by being welded to the implant.

There is additionally provided, in accordance with an application of the present invention, apparatus including:
a dental implant; and
a dental applicator, which is shaped so as to define:
a distal coupling surface, which is configured to removably engage the applicator with a proximal end of the dental implant,
a proximal coupling surface, and
a longitudinal portion, which is shaped so as to define an external surface that is rotationally asymmetric,
wherein the distal and the proximal coupling surfaces share a common central longitudinal axis.

For some applications, the apparatus further includes a retaining element, which is removably coupleable to the applicator, and which is shaped such that the rotationally-asymmetric surface of the applicator constrains a rotational orientation of the retaining element to a single rotational orientation with respect to the applicator.

For some applications, the distal coupling surface extends from a distal end of the applicator toward the proximal coupling surface.

Alternatively or additionally, for some applications, the proximal coupling surface extends from a proximal end of the applicator toward the distal coupling surface. For some applications, the distal coupling surface extends from a distal end of the applicator toward the proximal coupling surface.

For some applications, the distal coupling surface is rotationally symmetric and not circular. For example, the distal coupling surface may be regularly polygonally shaped. Alternatively or additionally, for some applications, the proximal coupling surface is rotationally symmetric and not circular. For example, the proximal coupling surface may be regularly polygonally shaped.

For some applications, each of the distal and the proximal coupling surfaces is rotationally symmetric and not circular. For example, the distal and the proximal coupling surface may be regularly polygonally shaped.

For some applications, the distal coupling surface is longitudinally non-overlapping with the rotationally-asymmetric external surface. Alternatively or additionally, for some applications, the proximal coupling surface is longitudinally non-overlapping with the rotationally-asymmetric external surface. For some applications, the distal and the proximal coupling surfaces are longitudinally non-overlapping with the rotationally-asymmetric external surface. For example, the distal and the proximal coupling surfaces may be male and regularly polygonally shaped.

For some applications, the distal coupling surface is male or female. Alternatively or additionally, for some applications, the proximal coupling surface is male or female.

For some applications, the applicator is shaped so as to define a channel therethrough, which is open to both distal and proximal ends of the applicator, and which is coaxial with the central longitudinal axis. For some applications, the applicator includes a connecting element, which is configured to be disposed at least partially in the channel, and to removably couple the applicator to the proximal implant end. For some applications, the connecting element includes a shaft, at least a portion of which defines a screw thread.

For some applications, the rotationally-asymmetric external surface extends from a distal end of the applicator toward a proximal end of the applicator. Alternatively or additionally, for some applications, the rotationally-asymmetric external surface extends from a proximal end of the applicator toward a distal end of the applicator.

There is yet additionally provided, in accordance with an application of the present invention, a method including:
providing (a) a dental implant having a lateral external surface, the implant being shaped so as to define a lumen therethrough having a lateral opening through the lateral external surface, (b) a delivery tube having a distal tube end, and (c) a retaining element;
causing the retaining element to assume a first position in which the retaining element removably couples the distal tube end to the implant such that the delivery tube is in fluid communication with the lumen via the lateral opening; and
causing the retaining element to assume a second position in which the retaining element does not couple the distal tube end to the implant.

For some applications, causing the retaining element to assume the second position includes causing the retaining element to assume the second position after causing the retaining element to assume the first position. Alternatively or additionally, for some applications, causing the retaining element to assume the second position includes causing the retaining element to assume the second position before causing the retaining element to assume the first position.

For some applications, the lumen has at least one distal opening through a distal external surface of the implant, and the method further includes:
forming a bore through a maxillary alveolar ridge;
inserting the implant into the bore at least until the distal opening comes into fluid communication with a surface of a Schneiderian membrane facing the ridge;
raising the membrane to form a cavity between the ridge and the membrane, by injecting a liquid through the lumen via the delivery tube when the retaining element is in the first position such that the distal tube end is removably coupled to the implant;
decoupling the distal tube end from the implant by transitioning the retaining element from the first position to the second position; and
further rotating the implant until the lateral opening is positioned entirely within at least one location selected from the group consisting of: the bore in the ridge, and the cavity between the ridge and the membrane.

For some applications, the method further includes providing a sealing element, which is configured to removably sealingly couple the delivery tube to the implant when the retaining element is in the first position. For some applications, the sealing element includes an element selected from the group consisting of: an o-ring and a gasket. For some applications, a distal portion of the sealing element is conical. For some applications, the distal tube end is embedded in the sealing element.

For some applications, providing the retaining element includes providing the retaining element in which at least a portion thereof includes a rigid material.

For some applications, at least a portion of the retaining element is disposed at least 1.5 cm from the lateral opening when the retaining element is in the first position.

For some applications, the retaining element is coupled to the delivery tube, and the method further includes removably coupling the retaining element to a proximal implant end of the implant.

For some applications, causing the retaining element to assume the first position includes removably coupling the retaining element to a proximal implant end of the implant via an applicator removably coupled to the proximal implant end, and causing the retaining element to assume the first position. For some applications, removably coupling the retaining element to the proximal implant end via the applicator includes disposing a portion of a retaining element body of the retaining element alongside the implant from the applicator to the lateral opening of the implant.

For some applications, the retaining element further includes a shaft, and causing the retaining element to assume the first position includes rotating the shaft to bring the distal tube end into contact with the lateral opening of the implant, to sealingly couple the distal tube end to the lateral opening. For some applications, removably coupling the retaining element to proximal implant end via the applicator includes positioning the shaft and the distal tube end at circumferentially opposite sides of the implant. For some applications, removably coupling the retaining element to proximal implant end via the applicator includes positioning the shaft and the distal tube end at a same circumferential side of the implant.

For some applications, the retaining element includes a shaft, a first end of which serves as the distal tube end, and causing the retaining element to assume the first position includes using the shaft to sealingly couple the distal tube end to the lateral opening of the implant. For some applications, causing the retaining element to assume the first position includes rotating the shaft to bring the distal tube end into contact with the lateral opening of the implant.

For some applications, removably coupling the retaining element to the proximal implant end via the applicator includes removably coupling the retaining element to the applicator. For some applications, the applicator is shaped so as to define a longitudinal portion that is shaped so as to define an external surface that is rotationally asymmetric. For some applications, the retaining element is shaped such that the rotationally-asymmetric surface of the applicator constrains a rotational orientation of the retaining element to a single rotational orientation with respect to the applicator.

For some applications, providing the retaining element includes providing the retaining element fixed to an applicator that is removably coupled to a proximal implant end of the implant.

For some applications, providing the implant includes providing the implant including a distal implant portion that extends from a distal implant end along up to 50% of a longitudinal length of the implant, and the lumen has at least one distal opening through a distal external surface of the distal implant portion.

For some applications, providing the implant includes providing the implant in which the lumen is not open to a proximal external surface of the implant within 2 mm of a proximal-most part of the implant.

For some applications, providing the implant includes providing the implant shaped such that the lumen defines exactly one lateral opening through the lateral external surface.

There is also provided, in accordance with an application of the present invention, a method including:

providing (a) a dental implant having a lateral external surface, the implant being shaped so as to define a lumen therethrough having a lateral opening through the lateral external surface, and (b) a delivery tube having a distal tube end;

removably coupling the distal tube end to the implant at a first interface, such that the delivery tube is in fluid communication with the lumen via the lateral opening; and removably coupling the delivery tube to the implant at a second interface remote from the first interface, so as to prevent movement of the distal tube end with respect to the implant.

There is further provided, in accordance with an application of the present invention, apparatus including:

a dental implant having a lateral external surface, the implant being shaped so as to define a lumen therethrough having a lateral opening through the lateral external surface; and a delivery tube having a distal tube end, which is removably coupled to the implant such that the delivery tube is in fluid communication with the lumen via the lateral opening.

For some applications, the lumen is not open to a proximal external surface of the implant within 2 mm of a proximal-most part of the implant. For some applications, the implant has a distal implant portion that extends from a distal implant end along up to 50% of a longitudinal length of the implant, and the lumen has at least one distal opening through a distal external surface of the distal implant portion. For some applications, the implant is shaped such that the lumen defines exactly one lateral opening through the lateral external surface. For some applications, when the delivery tube is coupled to the implant, a portion of the delivery tube runs alongside the implant such that a greatest distance between a longitudinal axis of the implant and a surface of the portion of the delivery tube farthest from the longitudinal axis is less than 7 mm, such as less than 6 mm.

For some applications, the distal tube end is welded to the implant, such that application of a breaking torque to the delivery tube breaks the delivery tube, thereby decoupling the delivery tube from the implant. For some applications, a portion of a wall of the delivery tube is thinner than the wall immediately adjacent to the portion, such that application of the breaking torque to the delivery tube breaks the delivery tube at the thinner portion. Typically, the thinner portion is within 3 mm of the distal tube end. For example the delivery tube may be shaped so as to be circumscribed with a groove that defines the thinner portion.

For some applications in which the distal tube end is welded to the implant, the apparatus further includes a rotation breaking tool, which is configured to be temporarily coupled to the dental implant, and to break the delivery tube by rotating the distal tube end with respect to the lateral opening, thereby applying the breaking torque to the delivery tube. For some applications, the apparatus further includes an applicator, which is removably coupled to a proximal implant end of the implant. For some applications, the rotation breaking tool is configured to be temporarily coupled to the proximal implant end after the applicator is decoupled therefrom.

For some applications, the applicator is configured to prevent application of the breaking torque to the delivery tube when the applicator is coupled to the proximal implant end. For some applications, the applicator is configured to prevent rotation of the distal tube end with respect to the lateral opening when the applicator is coupled to the proximal implant end. For some applications, the delivery tube includes a fixing element, the applicator includes a fixing element receptor, and, when the applicator is coupled to the proximal implant end, at least a portion of the fixing element is coupled to the fixing element receptor, thereby preventing the rotation of the distal tube end.

For some applications, the rotation breaking tool includes: a handle; a coupling element, which is positioned near a distal end of the handle, and which is configured to be coupled to the implant; and a breaking element, which is configured to apply the breaking torque to the delivery tube. For some applications, the rotation breaking tool further includes a rotating member, to which the breaking element is coupled, and which rotating member rotates with respect to the handle around the coupling element, and the coupling element remains stationary with respect to the handle even when the rotating member is rotated. For some applications, a longitudinal axis of the handle forms an angle of between 70 and 90 degrees with a longitudinal axis of the coupling element, such as 90 degrees.

Alternatively, a longitudinal axis of the handle forms an angle of between 0 and 30 degrees with a longitudinal axis of the coupling element, e.g., the longitudinal axis of the handle is parallel to the longitudinal axis of the coupling element. For some applications, the handle includes: a rotating sub-handle, which is in mechanical communication with the rotating member; and a stationary sub-handle, which is in mechanical communication with the coupling element. For some applications, the handle further includes: a rotating shaft, which provides the mechanical communication between the rotating sub-handle and the rotating member; and a stationary shaft, which provides the mechanical communication between the stationary sub-handle and the coupling element. For some applications, the handle is arranged such that the stationary shaft passes through the rotating shaft. Alternatively, the handle is arranged such that the rotating shaft passes through the stationary shaft.

For some applications in which the distal tube end is welded to the implant, the apparatus further includes an applicator, which is removably coupled to a proximal implant end of the implant, and which is configured to break the delivery tube by rotating the distal tube end with respect to the lateral opening. For some applications, the applicator is configured to apply a torque of greater than 50 Newton centimeters to the delivery tube, when rotating the distal tube end with respect to the lateral opening. For some applications, the applicator includes a lever arm, which is coupled to the delivery tube and arranged to rotate the distal tube end with respect to the lateral opening. For some applications, the applicator includes a rotatable surface accessible from a proximal end of the applicator, which rotatable surface is rotatable with respect to a portion of the applicator, rotation of which rotatable surface rotates the distal tube end by extending the lever arm. For some applications, the applicator includes: a connecting screw, which removably couples the applicator to the proximal implant end; and a rotatable surface accessible from a proximal end of the applicator, which rotatable surface is rotatable with respect to a portion of the applicator, and the applicator is configured such that rotation of the rotatable surface both (a) applies the breaking torque to the delivery tube that breaks the delivery tube, and (b) rotates the screw to decouple the applicator from the proximal implant end.

For some applications (in which the distal tube end is typically not welded to the implant), the apparatus further includes a retaining element, which is configured to assume a first position in which the retaining element couples the distal tube end to the implant, and a second position in which the retaining element does not couple the distal tube end to the implant. For some applications, the apparatus further includes a sealing element, which is configured to removably sealingly couple the delivery tube to the implant. For some applications, the retaining element is removably coupled to a proximal implant end of the implant, and coupled to the delivery tube.

For some applications in which the apparatus includes the retaining element, the apparatus further includes an applicator, which is removably coupled to a proximal implant end of the implant, and the retaining element is removably couplable to the applicator, and coupled to the delivery tube. For some applications, the retaining element includes a retaining element body, a portion of which is configured to be disposed alongside the implant, from the applicator to the lateral opening of the implant. For some applications, the retaining element further includes a shaft. For some applications, the shaft is configured such that rotation thereof brings the distal tube end into contact with the lateral opening of the implant.

For some applications in which the apparatus includes the retaining element, the apparatus further includes an applicator, which is removably coupled to a proximal implant end of the implant, and the retaining element is fixed to the applicator, and coupled to the delivery tube. For some applications, the distal tube end is shaped so as to define a cone. For some applications, the cone has an opening angle of between 0 and 60 degrees. For some applications, the cone is shaped so as to define a Morse taper. For some applications, the delivery tube is configured to pivot with respect to the applicator. For some applications, the applicator further includes a spring, which is configured to apply a force that separates the distal tube end from the implant when the retaining element assumes the second position.

There is further provided, in accordance with an application of the present invention, a method including:

forming a bore through a maxillary alveolar ridge;

inserting an implant into the bore at least until the distal opening comes into fluid communication with a surface of a Schneiderian membrane facing the ridge, which implant is shaped so as to define a lumen therethrough (a) having at least one distal opening through a distal external surface of the implant, and (b) having a lateral opening through a lateral external surface of the implant;

raising the membrane to form a cavity between the ridge and the membrane, by injecting a liquid through the lumen via a delivery tube having a distal tube end that is removably coupled to the implant such that the delivery tube is in fluid communication with the lumen via the lateral opening;

decoupling the distal tube end from the implant; and further rotating the implant until the lateral opening is positioned entirely within at least one location selected from the group consisting of: the bore in the ridge, and the cavity between the ridge and the membrane.

For some applications, the lumen is not open to a proximal external surface of the implant within 2 mm of a proximal-most part of the implant. For some applications, the implant is shaped such that the lumen defines exactly one lateral opening through the lateral external surface.

For some applications, the distal tube end is welded to the implant, and decoupling the distal tube end from the implant includes breaking the delivery tube by applying a breaking torque to the delivery tube. For some applications, a portion of a wall of the delivery tube is thinner than the wall immediately adjacent to the portion, and breaking the delivery tube includes breaking the delivery tube at the thinner portion by applying the breaking torque to the delivery tube. Typically, the thinner portion is within 3 mm of the distal tube end. For example, the delivery tube may be shaped so as to be circumscribed with a groove that defines the thinner portion.

For some applications in which the distal tube end is welded to the implant, applying the breaking torque includes: temporarily coupling a rotation breaking tool to the implant; breaking the delivery tube by using the rotation breaking tool to rotate the distal tube end with respect to the lateral opening, thereby applying the breaking torque to the delivery tube; and decoupling the rotation breaking tool from the implant.

For some applications, inserting the implant includes inserting the implant with an applicator removably coupled to a proximal implant end of the implant, and temporarily coupling the rotation breaking tool to the implant includes temporarily coupling the rotation breaking tool to the proximal implant end after decoupling the applicator therefrom. For some applications, the applicator is configured to prevent application of the breaking torque to the delivery tube when the applicator is coupled to the proximal implant end. For some applications, the applicator is configured to prevent rotation of the distal tube end with respect to the lateral opening when the applicator is coupled to the proximal implant end. For some applications, the delivery tube includes a fixing element, the applicator includes a fixing element receptor, and, when the applicator is coupled to the proximal implant end, at least a portion of the fixing element is coupled to the fixing element receptor, thereby preventing the rotation of the distal tube end.

For some applications, the rotation breaking tool includes (a) a handle, (b) a coupling element, which is positioned near a distal end of the handle, and (c) a breaking element, coupling the rotation breaking tool to the implant includes coupling the coupling element to the implant, and applying the breaking torque to the delivery tube includes using the breaking element to apply the breaking torque to the delivery tube. For some applications, the rotation breaking tool further includes a rotating member, to which the breaking element is coupled, and applying the breaking torque includes rotating the rotating member rotates with respect to the handle around the coupling element, while the coupling element remains stationary with respect to the handle.

For some applications, a longitudinal axis of the handle forms an angle of between 70 and 90 degrees with a longitudinal axis of the coupling element, such as 90 degrees. Alternatively, a longitudinal axis of the handle forms an angle of between 0 and 30 degrees with a longitudinal axis of the coupling element, e.g., the longitudinal axis of the handle is parallel to the longitudinal axis of the coupling element.

For some applications in which the distal tube end is welded to the implant, inserting the implant includes inserting the implant with an applicator removably coupled to a proximal implant end of the implant, and applying the breaking torque includes using the applicator rotate the distal tube end with respect to the lateral opening.

For some applications in which the distal tube end is welded to the implant, applying the breaking torque includes grasping the delivery tube with a human hand, and applying the breaking torque using the hand.

For some applications in which the distal tube end is welded to the implant, applying the breaking torque includes bringing a tool into contact with the delivery tube, and applying the breaking torque using the tool. For some applications, bringing the tool into contact includes grasping the delivery tube with the tool.

For some applications (in which the distal tube end is typically not welded to the implant), the method further includes providing a retaining element, which is configured to assume a first position in which the retaining element couples the distal tube end to the implant, and a second position in which the retaining element does not couple the distal tube end to the implant.

For some applications, raising the membrane includes removably coupling the retaining element to an applicator coupled to a proximal implant end of the implant, and causing the retaining element to assume the first position. For some applications, coupling the retaining element to the applicator including disposing a portion of a retaining element body of the retaining element alongside the implant from the applicator to the lateral opening of the implant. For some applications, the retaining element includes a shaft, a first end of which serves as the distal tube end, and coupling the distal tube end to the implant includes using the shaft to sealingly couple the distal tube end to the lateral opening of the implant. For some applications, coupling the distal tube end to the implant includes rotating the shaft to bring the distal tube end into contact with the lateral opening of the implant.

For some applications, providing the retaining element includes providing the retaining element (a) fixed to an applicator that is coupled to a proximal implant end of the implant, and (b) coupled to the delivery tube.

There is still further provided, in accordance with an application of the present invention, apparatus including:

a dental implant having a lateral external surface, the implant being shaped so as to define a lumen therethrough having a lateral opening through the lateral external surface; and a delivery tube having a distal tube end, which is removably coupled to the implant such that the delivery tube is in fluid communication with the lumen via the lateral opening, wherein the distal tube end is welded to the implant, such that application of a breaking torque to the delivery tube breaks the delivery tube, thereby decoupling the delivery tube from the implant.

For some applications, the lumen is not open to a proximal external surface of the implant within 2 mm of a proximal-most part of the implant. For some applications, the implant has a distal implant portion that extends from a distal implant end along up to 50% of a longitudinal length of the implant, and the lumen has at least one distal opening through a distal external surface of the distal implant portion. For some applications, the implant is shaped such that the lumen defines exactly one lateral opening through the lateral external surface. For some applications, when the delivery tube is coupled to the implant, a portion of the delivery tube runs alongside the implant such that a greatest distance between a longitudinal axis of the implant and a surface of the portion of the delivery tube farthest from the longitudinal axis is less than 7 mm, such as less than 6 mm.

For some applications, a portion of a wall of the delivery tube is thinner than the wall immediately adjacent to the portion, such that application of the breaking torque to the delivery tube breaks the delivery tube at the thinner portion. Typically, the thinner portion is within 3 mm of the distal tube end. For example, the delivery tube may be shaped so as to be circumscribed with a groove that defines the thinner portion.

For some applications, the apparatus further includes a rotation breaking tool, which is configured to be temporarily coupled to the dental implant, and to break the delivery tube by rotating the distal tube end with respect to the lateral opening, thereby applying the breaking torque to the delivery tube. For some applications, the apparatus further includes an applicator, which is removably coupled to a proximal implant end of the implant. For some applications, the rotation breaking tool is configured to be temporarily coupled to the proximal implant end after the applicator is decoupled therefrom. For some applications, the applicator is configured to prevent application of the breaking torque to the delivery tube when the applicator is coupled to the proximal implant end. For some applications, the applicator is configured to prevent rotation of the distal tube end with respect to the lateral opening when the applicator is coupled to the proximal implant end. For some applications, the delivery tube includes a fixing element, the applicator includes a fixing element receptor, and, when the applicator is coupled to the proximal implant end, at least a portion of the fixing element is coupled to the fixing element receptor, thereby preventing the rotation of the distal tube end.

For some applications, the rotation breaking tool includes: a handle; a coupling element, which is positioned near a distal end of the handle, and which is configured to be coupled to the implant; and a breaking element, which is configured to apply the breaking torque to the delivery tube. For some applications, the rotation breaking tool further includes a rotating member, to which the breaking element is coupled, and which rotating member rotates with respect to the handle around the coupling element, and the coupling element remains stationary with respect to the handle even when the rotating member is rotated.

For some applications, a longitudinal axis of the handle forms an angle of between 70 and 90 degrees with a longitudinal axis of the coupling element, such as 90 degrees. Alternatively, a longitudinal axis of the handle forms an angle of between 0 and 30 degrees with a longitudinal axis of the coupling element, e.g., the longitudinal axis of the handle is parallel to the longitudinal axis of the coupling element. For some applications, the handle includes: a rotating sub-handle, which is in mechanical communication with the rotating member; and a stationary sub-handle, which is in mechanical communication with the coupling element. For some applications, the handle further includes: a rotating shaft, which provides the mechanical communication between the rotating sub-handle and the rotating member; and a stationary shaft, which provides the mechanical communication between the stationary sub-handle and the coupling element. For some applications, the handle is arranged such that the stationary shaft passes through the rotating shaft. Alternatively, the handle is arranged such that the rotating shaft passes through the stationary shaft.

For some applications, the apparatus further includes an applicator, which is removably coupled to a proximal implant end of the implant, and which is configured to break the delivery tube by rotating the distal tube end with respect to the lateral opening. For some applications, the applicator is configured to apply a torque of greater than 50 Newton centimeters to the delivery tube, when rotating the distal tube end with respect to the lateral opening. For some applications, the applicator includes a lever arm, which is coupled to the delivery tube and arranged to rotate the distal tube end with respect to the lateral opening. For some applications, the applicator includes a rotatable surface accessible from a proximal end of the applicator, which rotatable surface is rotatable with respect to a portion of the applicator, rotation of which rotatable surface rotates the distal tube end by extending the lever arm. For some applications, the applicator includes: a connecting screw, which removably couples the applicator to the proximal implant end; and a rotatable surface accessible from a proximal end of the applicator, which rotatable surface is rotatable with respect to a portion of the applicator, and the applicator is configured such that rotation of the rotatable surface both (a) applies the breaking torque to the delivery tube that breaks the delivery tube, and (b) rotates the screw to decouple the applicator from the proximal implant end.

The present invention will be more fully understood from the following detailed description of applications thereof, taken together with the drawings, in which:

BRIEF DESCRIPTION OF THE DRAWINGS

FIGS. 3A-D are schematic illustrations of alternative configurations of the implant of FIGS. 1A-C and an applicator in which the distal end of a delivery tube is initially removably coupled to the implant, in accordance with respective applications of the present invention;

FIG. 4 is a schematic illustration of a rotation breaking tool, in accordance with an application of the present invention;

FIGS. 5A-B are schematic side-views of the rotation breaking tool of FIG. 4, in accordance with an application of the present invention;

FIGS. 9A-B are schematic isometric and cross-sectional illustrations, respectively, of yet another configuration of a rotation breaking tool, in accordance with an application of the present invention;

FIGS. 10A-B are schematic illustrations of a first component of the breaking tool of FIGS. 9A-B, in accordance with an application of the present invention;

FIGS. 11A-D are schematic illustrations of a second component of the breaking tool of FIGS. 9A-B, in accordance with an application of the present invention;

FIG. 12 is a schematic illustration of still another configuration of a rotation breaking tool, in accordance with an application of the present invention;

FIG. 13 is a schematic cross-sectional illustration of the rotation breaking tool of FIG. 12, in accordance with an application of the present invention;

FIGS. 19A-C are schematic illustrations of another configuration of a dental implant, an applicator, and a retaining element in a second position, in accordance with an application of the present invention;

FIG. 19D is a schematic illustration of the implant, applicator and retaining element of FIGS. 19A-C in a first position, in accordance with an application of the present invention;

FIGS. 20A-G are schematic illustrations of yet another configuration of the implant, the applicator, and the retaining element of FIGS. 19A-D, in accordance with an application of the present invention;

FIGS. 21A-D, 22A-B, 23, and 24 are schematic illustrations of a dental implant and an applicator in which the distal end of a delivery tube is initially welded to the implant, in accordance with an application of the present invention;

FIGS. 25A-G are schematic illustrations of several steps of a minimally-invasive closed sinus lift surgical procedure for implanting a dental implant, in accordance with an application of the present invention;

FIGS. 25H-J are schematic illustration of alternative techniques for injecting regenerative material, in accordance with an application of the present invention;

FIGS. 29A-F are schematic illustrations of several steps of a minimally-invasive closed lateral ridge augmentation surgical procedure for implanting a dental implant, in accordance with an application of the present invention;

FIGS. 32A-C are schematic illustrations of an implant and a dental applicator, in accordance with an application of the present invention; and FIG. 33 is a schematic cross-sectional illustration showing a retaining element removably coupled to the applicator of FIGS. 32A-C, in accordance with an application of the present invention.

DETAILED DESCRIPTION OF APPLICATIONS

Figure 1A:
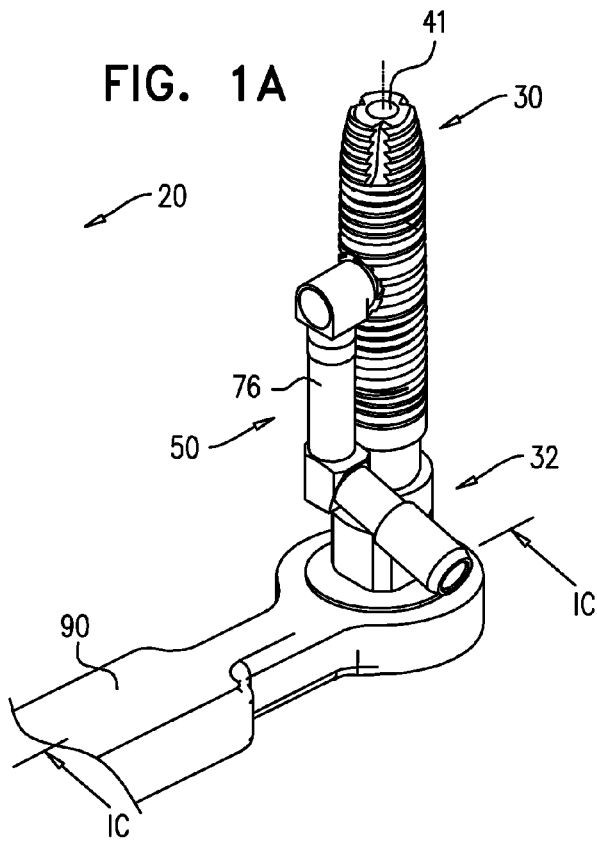
FIGS. 1A-C are schematic illustrations of a dental implant system, in accordance with an embodiment of the present invention.
Figure 1B:
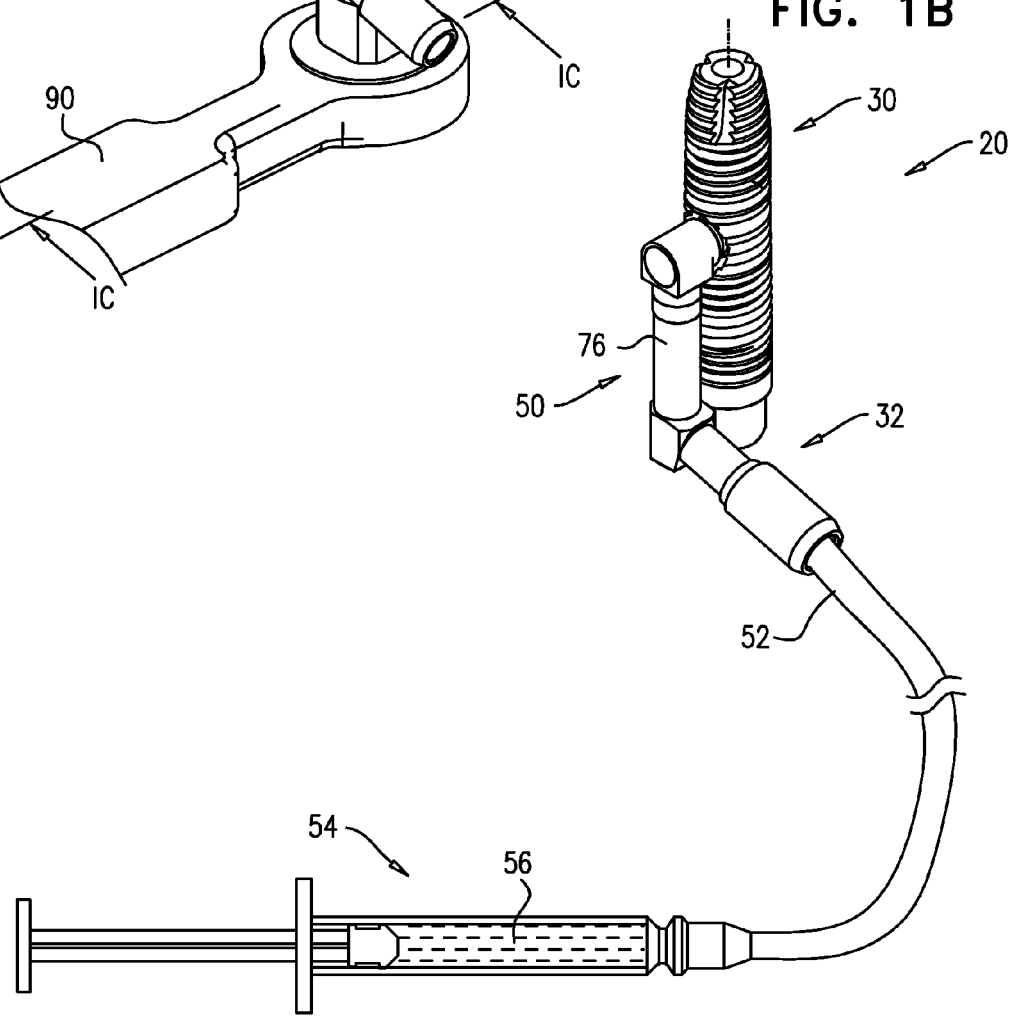
Figure 1C:
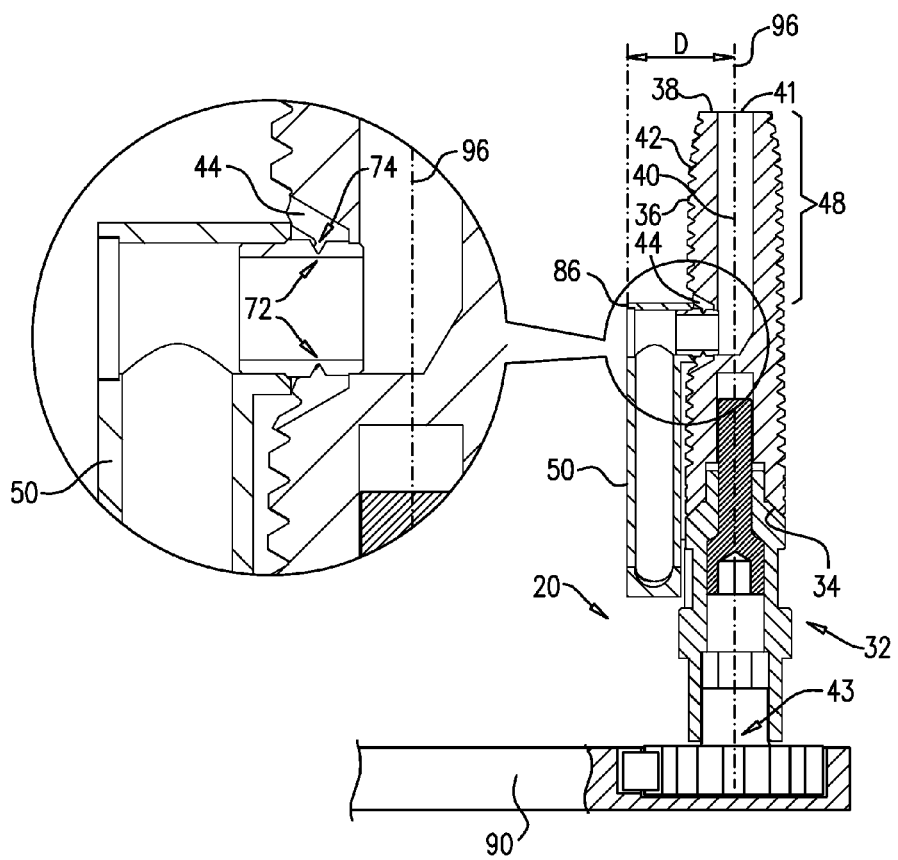

FIGS. 1A-C are schematic illustrations of a dental implant system 20, in accordance with an embodiment of the present invention. FIGS. 1A-B are isometric views of the system, and FIG. 1C is a cross-sectional view of FIG. 1A along line IC-IC. System 20 comprises a dental implant 30, which is typically shaped so as to define a lumen 40 therethrough that is open through a distal opening 41 to a distal portion 48 of the implant that extends from a distal implant end 38 of the implant along up to 50% of a longitudinal length of the implant, such as up to 30% of the length, up to 15% of the length, or up to 5% of the length. For some applications, distal portion 48 has a longitudinal length of up to 8 mm, such as up to 6 mm, up to 4 mm, or up to 2 mm, e.g., 5 mm or 8 mm. As used herein, including in the claims, the "distal" end of the implant is the end that is inserted first into a bone, such as an alveolar ridge, and is sometimes referred to in the art as the apical end, and the "proximal" end of the implant is the end of the implant opposite the distal end, e.g., that faces the oral cavity, and is sometimes referred to in the art as the coronal end. Similarly, "distal" means situated toward the distal end of the implant, and "proximal" means situated toward the proximal end of the implant.

Distal opening 41 may be located at distal implant end 38, such as centered on the distal implant end, e.g., at a distal tip of distal implant end 38, or not centered on the distal implant end (and thus located at a location other than the distal tip), such as described hereinbelow with reference to FIG. 2A. Alternatively, distal opening(s) 41 may be located at one or more locations along distal implant portion 48, including at locations on lateral surface 42. For some applications, the lumen is open to the distal end via a plurality of openings 41, which for some applications results in a more even distribution of regenerative material in the cavity between the ridge and the Schneiderian membrane, as described hereinbelow, and/or permits passage of the regenerative material even if some of the openings should become blocked with bone particles. Dental implant 30 is typically generally cylindrical, tapered, or conic in shape, other than the lumen, and typically comprises a metal such as titanium, or a ceramic, such as a zirconia (zirconium dioxide) ceramic. The implant may have a greatest diameter of between about 2 and about 7 mm, and may be provided in a variety of longitudinal lengths, e.g., between about 7 and about 18 mm, e.g., between about 12 and about 16 mm, such as about 15 mm. For some applications, the implant has a longitudinal length of less than 20 mm and a greatest diameter of less than 10 mm.

For some applications, dental implant 30 comprises a self-tapping osseointegrated dental implant. For these applications, at least a portion of a lateral external surface 42 of implant 30 is typically shaped so as to define a cutting surface, e.g., a screw thread 36, or other connecting element. For example, the portion may be in a vicinity of a distal end 38 of the implant, or may include all or nearly all of the lateral surface.

For some applications, system 20 comprises an applicator 32 that is removably coupled to a proximal end 34 of implant 30. For some applications, applicator 32 is shaped so as to define a distal male coupling element, e.g., a hexagonal head, that is inserted into a correspondingly shaped proximal female coupling element, e.g., a hexagonal socket, defined by dental implant 30. Friction between the head and socket removably couples the implant to the applicator. Alternatively, another coupling element removably couples the implant to the applicator. A proximal end of applicator 32 is typically shaped so as to define a coupling element 43, such as a female coupling element (as shown in FIG. 1), e.g., a hexagonal or square socket, or a male coupling element (configuration not shown), e.g., a hexagonal or square head. During an implantation procedure, such as described hereinbelow with reference to FIGS. 25A-J, 26A-B, 27A-E, and 29A-F, the gloved hand of the surgeon generally touches the applicator, rather than the implant itself. System 20 is typically packaged and provided to the surgeon with the applicator 32 coupled to implant 30.

Typically, implant 30 comprises a two-stage implant. The surgeon couples an abutment to the proximal end of the implant after osseointegration of the implant, as is known in the art, such as described hereinbelow with reference to FIG. 25G. Alternatively, implant 30 comprises a single-stage transgingival implant, which is shaped so as to define an integrated abutment, as is known in the art.

For some applications, as shown in FIGS. 1A-C (and in FIGS. 3A-D, 15-18, 19A-D, 20A-G, 21A-24, and 28A-B hereinbelow), a proximal end of lumen 40 has a lateral opening 44 (typically exactly one lateral opening) through lateral external surface 42 of the implant, and the lumen is not open to a proximal external surface of the implant within 2 mm of a proximal-most part of implant 30. For some applications, the lumen is not open to the proximal external surface within 3 mm of the proximal-most part of the implant. Implant 30 is typically permanently closed within 3 mm of the proximal-most part of the implant, for these applications. Alternatively, the proximal end of lumen 40 is open to proximal implant end 34. Typically, the lateral opening is at least 15 mm from distal implant end 38, such as at least 2 mm (e.g., 8 mm from the distal implant end). Typically, the lateral opening is at least 2 mm from the proximal implant end, such as at least 3 mm or at least 4 mm.

System 20 further comprises a delivery tube 50, a distal end of which is coupled to lumen 40 via lateral opening 44. For some applications, the distal end of delivery tube 50 is initially welded to implant 30. The welding of delivery tube 50 to implant 30 provides a strong seal that is able to withstand the pressure of the fluid provided by fluid source 54 (such as described hereinbelow with reference to FIG. 25C) and/or the injection of a regenerative material (as described hereinbelow with reference to FIG. 25D). The delivery tube may be welded to implant 30 by laser welding overlapping spots around the circumference of the delivery tube. Alternatively, for some applications, the distal end of delivery tube 50 is initially soldered to implant 30.

For some applications, as best seen in the blow-up in FIG. 1C, a portion 72 of the wall of delivery tube 50 is thinner than the wall immediately adjacent to the portion, such that application of a breaking torque to the delivery tube breaks the delivery tube at the thinner portion, thereby decoupling the delivery tube from the implant. Typically, the thinner portion is within 3 mm of the distal end of the delivery tube, such as within 2 mm or within 1 mm of the distal end. The thinner portion is typically recessed into lateral external surface 42 of the implant. For some applications, at least a portion of the lateral surface that includes lateral opening 44 is shaped so as to define screw thread 36. For these applications, the thinner portion is recessed into the lateral external surface below the raised helical rib of screw thread 36. As a result, the small distal broken portion of the delivery tube that remains coupled to the implant after the delivery tube is broken does not interfere with the functioning of screw thread 36.

Typically, thinner portion 72 of delivery tube 50 is sufficiently thin such that the application of a breaking torque of less than 50 Newton centimeters (Ncm) breaks the delivery tube at the thinner portion. For some applications, the thinner portion has a width of less than 0.1 mm, such as less than 0.05 mm.

In this application of the present invention (and in some other applications of the present invention), delivery tube 50 typically comprises a rigid material, such as metal (e.g., titanium). For some applications, the delivery tube is shaped so as to be circumscribed with a groove 74 that defines thinner portion 72. For example, the tube may be manufactured by scoring the implant to form the groove that serves as the thinner portion. Typically, the groove is V-shaped, such that application of the breaking torque causes a concentration of force to be applied at the tip of the V, thereby breaking the delivery tube at the groove.

For some applications, the delivery tube is shaped so as to define a bend 86 at between about 5 and about 20 mm from the distal tube end, such as within about 10 mm of the distal tube end. For example, the bend may have an angle of between about 85 and about 95 degrees.

Typically, when delivery tube 50 is coupled to the implant prior to breaking of thinner portion 72, portion 76 of the delivery tube runs alongside the implant such that, as shown in FIG. 1C, a greatest distance D between a longitudinal axis 96 of the implant and a surface of portion 76 of the delivery tube farthest from the longitudinal axis is less than 7 mm, e.g., less than 6 mm, such as less than 5 mm. Such a small distance allows the implant and delivery tube to be readily placed between adjacent teeth during an implantation procedure, such as described hereinbelow with reference to FIGS. 25B-E.

Alternatively, the delivery tube may be coupled to the lumen using a miniature luer connector, by friction, using a removable coupling element, and/or as described hereinbelow with reference to FIG. 15-18, 19A-D, or 20A-G. Alternatively, the tube may screw into the lumen, so as to be rotationally secured to the implant throughout the implantation procedure. Further alternatively or additionally, the distal end of delivery tube 50 comprises a sealing element, which is configured to removably sealingly couple delivery tube 50 to implant 30. For example, the sealing element may be configured as shown in and/or described hereinbelow with reference to FIGS. 19A-B or FIG. 30, or the sealing element may comprise an o-ring or a gasket.

As shown in FIGS. 1A and 1C, during a portion of an implantation procedure, a rotation tool 90 is coupled to coupling element 43 of the applicator 32, for rotating implant 30 via applicator 32. For example, the rotation tool may comprise a conventional manual wrench (e.g., a simple hand wrench, or a ratchet wrench), or a conventional drill or motor to which an appropriate drill head is attached, and which is operated at a low speed and at low torque, such as a physiodispenser. Alternatively, rotation tool 90 may comprise a conventional hexagonal tool with a knurled knob, such as a knurled hex screwdriver, and along its axis, a thin rod having a hexagonal head which fits into a female hexagonal socket defined by coupling element 43 of applicator 32.

As shown in FIG. 1B, during at least a portion of the implantation procedure, delivery tube 50 is in fluid communication with a supply tube 52, which in turn is in fluid communication with a source of fluid 54. Fluid source 54 may comprise a manual syringe 56 or powered drug delivery device, as is known in the art. For some applications, a proximal end of supply tube 52 is coupled to fluid source 54, e.g., manual syringe 56, by a luer lock, which is located remotely from implant 30.

Figure 2A:
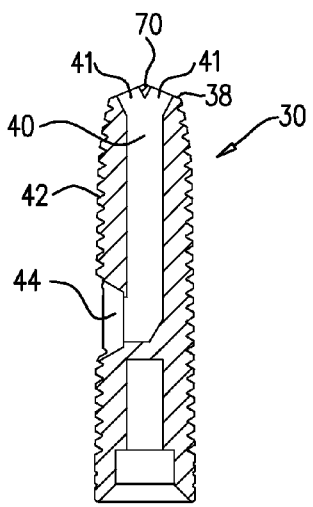
FIGS. 2A-C are schematic illustrations of alternative configurations of a dental implant of the dental implant system of FIGS. 1A-C, in accordance with respective applications of the present invention.
Figure 2B:
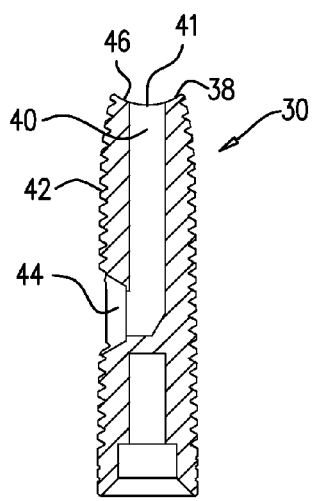
Figure 2C:
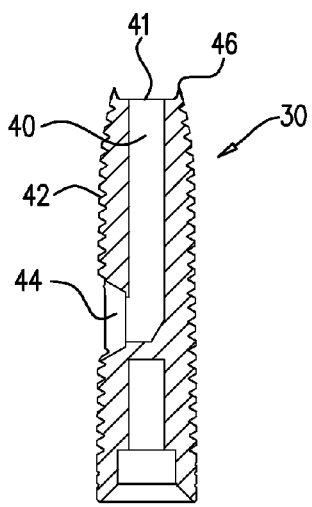

Reference is made to FIGS. 2A-C, which are schematic illustrations of alternative configurations of dental implant 30, in accordance with respective applications of the present invention. In the configuration shown in FIG. 2A, distal opening 41 of lumen 40 is located on distal implant end 38 at a location other than a distal tip 70 of the implant. For some applications, the location is within 3 mm of distal tip of 70, as measured along the surface of the distal tip. As mentioned above with reference to FIGS. 1A-C, for some applications, lumen 40 is open to the distal end via a plurality of distal openings 41, as shown in FIG. 2A. One or more of the openings may be at a location other than distal tip 70, including at one or more locations at distal implant end 38 and/or elsewhere on distal implant portion 48. Alternatively, lumen 40 is open to distal implant end 38 or distal implant portion 48 via exactly one opening (configuration not shown in FIG. 2A).

In the configuration shown in FIG. 2B, distal implant end 38 is concave, such that the raised edge of the concavity defines a sharp cutting surface 46. In the configuration shown in FIG. 2C, distal implant end 38 is generally flat, and the distal end is shaped so as to define sharp cutting surface 46, typically near the edge of the distal end.

Reference is now made to FIGS. 3A-D, which are schematic illustrations of alternative configurations of dental implant 30 and applicator 32 in which the distal end of delivery tube 50 is initially removably coupled to implant 30 at a first interface to implant 30, in accordance with respective applications of the present invention. For example, the delivery tube end may be removably coupled to the implant by being welded to the implant at the first interface. FIGS. 3A and 3C show dental implant 30 and applicator 32 not attached to each other, while FIGS. 3B and 3D show the applicator attached to the dental implant. For applications in which the delivery tube end is welded to the implant, a separate tool is used to break the delivery tube from the implant, such as one of the tools described hereinbelow with reference to FIG. 4-6B, 7-8B, 9A-11D, or 12-14. For some applications, applicator 32 is provided, in which case the applicator is typically removably coupled to the proximal end of implant 30, such as using coupling techniques described hereinabove with reference to FIGS. 1A-C.

In this configuration, delivery tube 50 and applicator 32, if provided, are configured such that the applicator 32 prevents decoupling of delivery tube 50 from implant 30, such as by preventing movement (e.g., rotation) of the delivery tube end with respect to the implant, for example by preventing application of a breaking torque to the delivery tube, typically by preventing rotation of the distal tube end with respect to the lateral opening of the implant. For some applications, delivery tube 50 is directly or indirectly removably coupled to implant 30 at a second interface remote from the first interface, so as to prevent the movement (e.g., the rotation) of the distal tube end with respect to the implant. For some applications in which applicator 32 is provided, the applicator is removably coupled to the proximal implant end at the second interface, and indirectly removably couples the delivery tube to the implant. For example, delivery tube 50 may comprise a fixing element 100, and applicator 32 may be shaped so as to define a corresponding fixing element receptor 102. When applicator 32 is coupled to implant 30, a proximal portion 104 of fixing element 100 is coupled to fixing element receptor 102, thereby preventing non-longitudinal movement of the fixing element, and thus rotation of the delivery tube. For example, the fixing element may be oriented generally parallel to distal portion 76 of delivery tube 50 and to longitudinal axis 96 of implant 30. Removal of applicator 32 from implant 30 frees the fixing element, thereby allowing rotation of delivery tube 50 and breaking thereof from the implant.

For some applications, as shown in FIGS. 3A-B, fixing element 100 is shaped so as to define a fixing pin, and fixing element receptor 102 is shaped so as to define a receptor hole. The fixing pin is positioned within the fixing hole. For other applications, as shown in FIGS. 3C-D, proximal portion 104 of fixing element 100 is shaped so as to define a slot or groove, and fixing element receptor 102 is shaped so as to define a corresponding coupling surface that fixes the fixing element to the fixing element receptor when the applicator is coupled to the implant. Other pairs of corresponding coupling elements will be evident to those skilled in the art who have read the present application, and are within the scope of the invention.

Alternatively, for some applications, delivery tube 50 and applicator 32 are not configured to prevent decoupling of the delivery tube from the implant, e.g., the delivery tube does not comprise the fixing pin, and the applicator is not shaped so as to define the fixing hole.

Figure 6A:
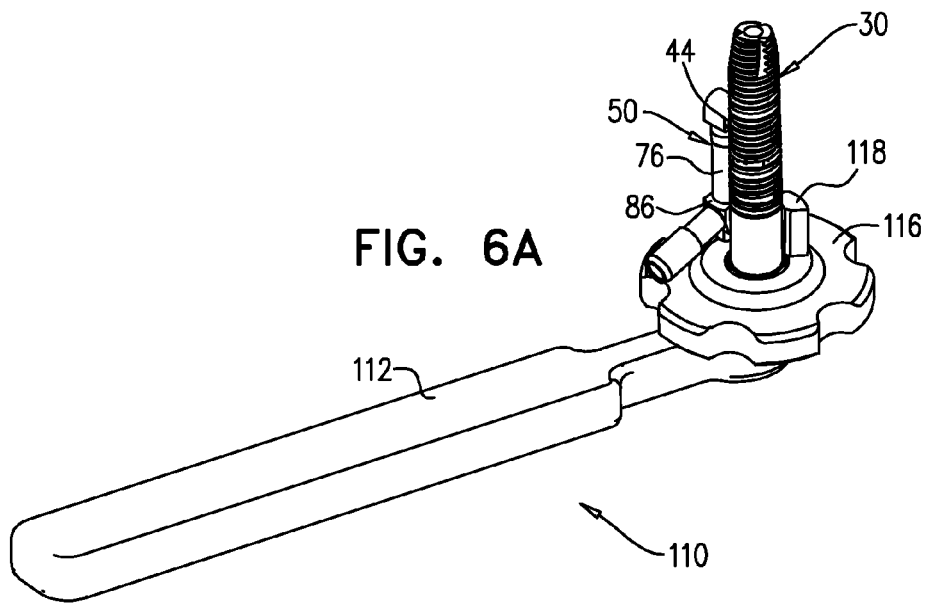
FIGS. 6A-B are schematic illustrations of the rotation breaking tool of FIG. 4 coupled to the implant of FIGS. 1A-C, in accordance with an application of the present invention.
Figure 6B:
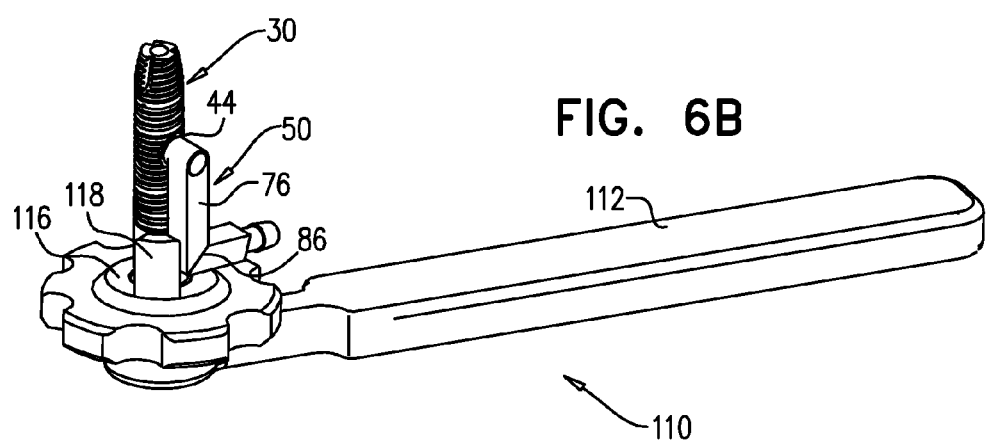

Reference is now made to FIGS. 4-6B, which are schematic illustrations of a rotation breaking tool 110, in accordance with an application of the present invention. FIG. 4 is an isometric view of tool 110, FIG. 5A is a side-view of the tool, and FIG. 5B is a cross-sectional side-view of the tool along line IXB-IXB of FIG. 4. FIGS. 6A-B show tool 110 coupled to implant 30. Tool 110 is used to break delivery tube 50 from implant 30, for applications in which applicator 32 is not configured to perform such breaking. For example, tool 110 may be used with the configuration of implant 30 and applicator 32 described hereinabove with reference to FIGS. 1A-C and 3A-D. Typically, tool 110 is temporarily coupled to the proximal end of implant 30 during a surgical procedure, after applicator 32 has been decoupled from the implant, for example as described hereinbelow with reference to FIG. 25E. (Typically, the tool is coupled to the same coupling surface of the implant to which the applicator is coupled.) Alternatively, tool 110 is coupled to implant 30 indirectly via applicator 32, by coupling the tool to the proximal end of the applicator (configuration not shown).

Tool 110 comprises a handle 112 and a coupling element 114 positioned near a distal end of the handle. For some applications, as shown in FIGS. 4-6B, a longitudinal axis of handle 112 forms an angle of between 70 and 90 degrees with a longitudinal axis of coupling element 114, e.g., is perpendicular to coupling element 114, as shown. Coupling element 114 is configured to temporarily engage a corresponding coupling element of implant 30. For example, coupling element 114 may comprise a male coupling element that is inserted into a corresponding female coupling element of the implant. Friction between coupling element 114 and the socket of the implant removably couples the tool to the implant. The male coupling element may, for example, be shaped so as do define a short cylinder extending from a hexagonal head. Tool 110 further comprises a rotating member 116, which is positioned around coupling element 114, such that a base 117 of the coupling element passes through the rotating member, as best seen in FIG. 5B. The rotating member is thus free to rotate with respect to the handle of the tool, while the coupling element remains stationary with respect to the handle. Rotating member 116 is shaped so as to define a human interface surface, in order to facilitate convenient direct rotation by the surgeon. In the configurations described with reference to FIGS. 4-6B, 7-8B, 9A-11D, and 12-14, handle 112 typically has a length along a longitudinal axis thereof of at least 2 cm, no more than 12 cm, and/or between 2 and 12 cm, e.g., between 4 and 9 cm.

Rotating member 116 comprises a breaking element 118, which extends in the same direction as coupling element 114 (e.g., perpendicular to the handle), partially alongside the coupling element. The breaking element may, for example, be shaped as a tab. As shown in FIGS. 6A-B, the breaking element is configured to apply a breaking torque to distal portion 76 of delivery tube 50, upon rotation of rotating member 116. The breaking element typically makes contact with the delivery tube near bend 86 of the delivery tube. In the exemplary configuration shown in FIGS. 6A-B, rotating member 116 is rotated counterclockwise as viewed from above (typically by between 180 and 360 degrees), in order to push breaking element 118 against delivery tube 50. The torque rotates the distal end of the delivery tube with respect to lateral opening 44 of implant 30, thereby breaking the delivery tube from the implant. After breaking the delivery tube from the implant, tool 110 is decoupled from the implant.

The portion of tool 110 not within implant 30 when the tool is coupled to the implant typically has a height H of between 0.5 and 3 cm, such as less than 2 cm, as shown in FIG. 5B. Such a small height requires minimal height in the mouth during use of the tool, thereby enabling minimal mouth opening by the patient in order to insert the tool into the mouth.

Figure 7:
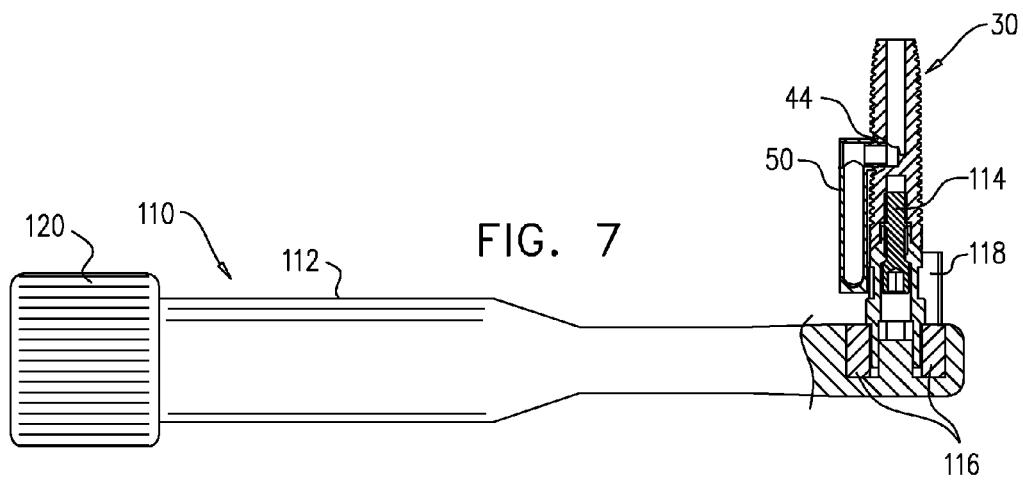
FIG. 7 is a schematic illustration of another configuration of a rotation breaking tool, in accordance with an application of the present invention.
Figure 8A:
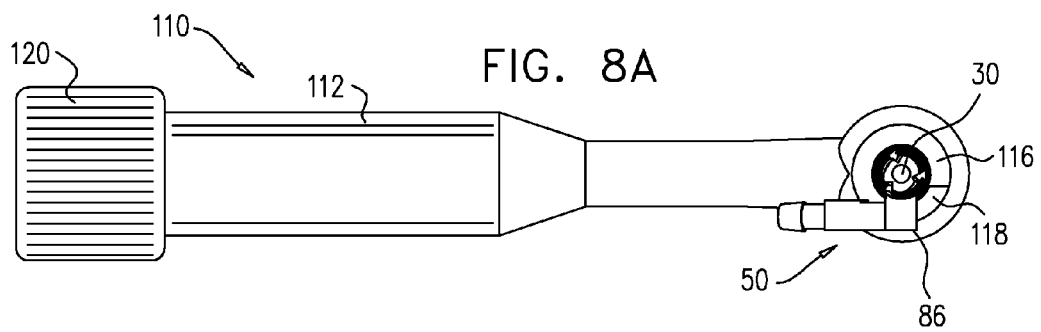
FIGS. 8A-B are schematic illustrations of the rotation breaking tool of FIG. 7 coupled to the implant of FIGS. 1A-C, in accordance with an application of the present invention.
Figure 8B:
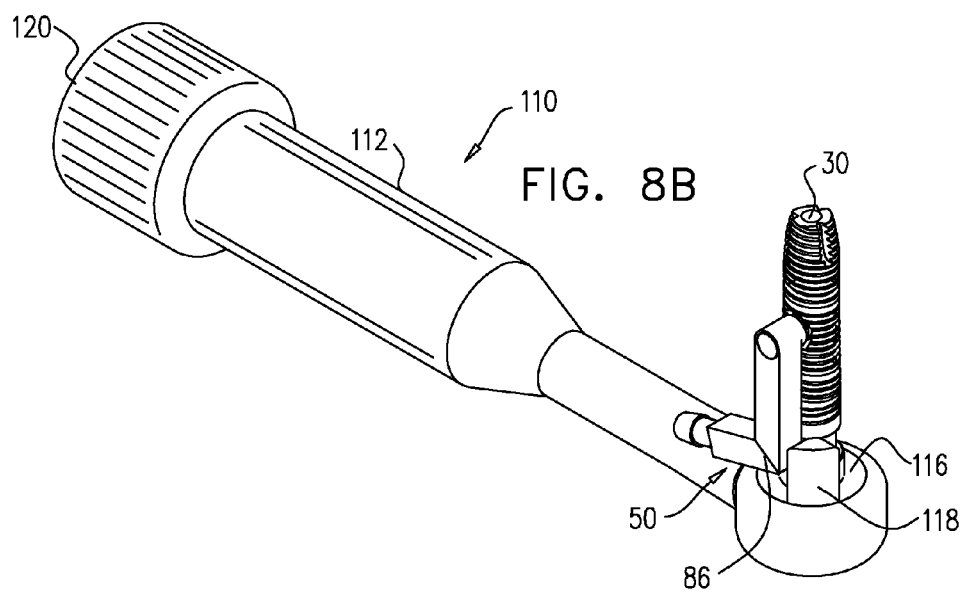

Reference is made to FIGS. 7-8B, which are schematic illustrations of another configuration of rotation breaking tool 110, in accordance with an application of the present invention. FIG. 7 is a cross-sectional side-view of tool 110 coupled to implant 30, and FIGS. 8A and 8B show the tool coupled to implant 30, viewed from the top (the direction in which coupling element 114 protrudes), and the side, respectively.

In this configuration of tool 110, as in the configuration shown in FIGS. 4-6B, coupling element 114 typically extends at an angle of between 70 and 90 degrees, e.g., at a right angle. However, unlike in the configuration shown in FIG. 8-6B, in this configuration the rotating member 116 is indirectly, remotely rotated by the surgeon by turning a knob 120 that is typically positioned at or near a proximal end of the handle. Tool 110 comprises one or more rods, gears, and/or cams (not shown), typically positioned within the handle, which together translate the rotation of knob 120 to rotation of rotating member 116. As in the configuration shown in FIGS. 4-6B, the coupling element remains stationary with respect to the handle while the rotating member rotates, typically by between 180 and 360 degrees.

Reference is made to FIGS. 9A-B, which are schematic isometric and cross-sectional illustrations, respectively, of yet another configuration of rotation breaking tool 110, in accordance with an application of the present invention. In this configuration of tool 110, unlike in the configurations shown in FIGS. 4-6B and 7-12, coupling element 114 is oriented at an angle of between 0 and 30 degrees with respect to a longitudinal axis 122 of handle 112, such as parallel to the longitudinal axis, typically concentric with the axis. Rotating member 116 and breaking element 118 rotate around axis 122.

Tool 110 is configured to enable rotation of breaking element 118 while coupling element 114 is held stationary. To enable such rotation, for some applications handle 112 comprises a rotating sub-handle 124 and a stationary sub-handle 126. Rotating sub-handle 124 is in mechanical communication with rotating member 116 via a rotating shaft 128, and stationary sub-handle 126 is in mechanical communication with coupling element 114 via a stationary shaft 130. For some applications, as shown in FIG. 9A-B, stationary shaft 130 passes through rotating shaft 128. Rotating and stationary sub-handles 124 and 126 typically are shaped so as to define respective knobs, to facilitate easy grasping by the surgeon. In the configuration shown in FIG. 9A-B, stationary sub-handle 126 is proximal to rotating sub-handle 124, i.e., the stationary sub-handle is farther from coupling element 114 than is the rotating sub-handle.

To use tool 110 to break delivery tube 50 from implant 30, the surgeon temporarily couples coupling element 114 to the proximal end of the implant. The surgeon holds stationary sub-handle 126 rotationally stationary, while at the same time rotating rotating sub-handle 124 (typically by between 180 and 360 degrees). This relative rotation pushes breaking element 118 against delivery tube 50, thereby breaking the delivery tube from the implant.

Reference is made to FIGS. 10A-B and 11A-D, which are schematic illustrations of components of tool 110 in the configuration shown in FIGS. 9A-B, in accordance with an application of the present invention. FIGS. 10A-B show a first component 132 of tool 110, which component comprises stationary sub-handle 126, stationary shaft 130, and coupling element 114. FIGS. 11A-D show a second component 134 of tool 110, which component comprises rotating sub-handle 124, rotating shaft 128, rotating member 116, and breaking element 118. Rotating sub-handle 124 and rotating shaft 128 together define a lumen 136 that passes through the rotating sub-handle and rotating shaft, as shown in FIG. 11B. FIG. 11D shows a distal view of the distal end of second component 134.

Tool 110 is assembled by passing stationary shaft 130 of first component 132 through lumen 136 of second component 134. First component 132 can freely rotate with respect to the second component 132. Typically, the components are configured to prevent the first component from separating from the second component.

Figure 14:
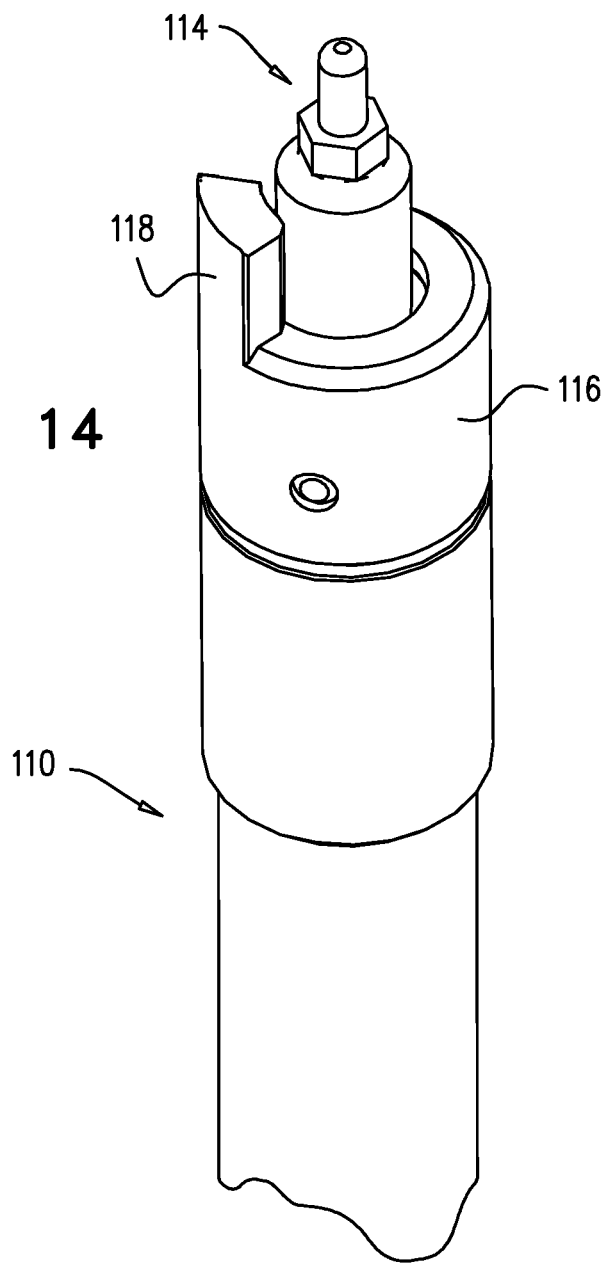
FIG. 14 is a schematic cross-sectional illustration of a distal end of the rotation breaking tool of FIG. 12, in accordance with an application of the present invention.

Reference is made to FIGS. 12-14, which are schematic illustrations of still another configuration of rotation breaking tool 110, in accordance with an application of the present invention. FIGS. 12 and 13 are isometric and cross-sectional views, respectively, of tool 110 temporarily coupled to implant 30, and FIG. 14 is an isometric enlargement of a distal end of the tool not coupled to the implant. In this configuration of tool 110, as in the configurations shown in FIGS. 9A-11D, coupling element 114 is oriented at an angle of between 0 and 30 degrees with respect to longitudinal axis 122 of handle 112, such as parallel to the longitudinal axis, typically concentric with the axis. Rotating member 116 and breaking element 118 rotate around axis 122.

Tool 110 is configured to enable rotation of breaking element 118 while coupling element 114 is held stationary. To enable such rotation, for some applications tool 110 comprises rotating sub-handle 124 and stationary sub-handle 126. Rotating sub-handle 124 is in mechanical communication with rotating member 116 via rotating shaft 128, and stationary sub-handle 126 is in mechanical communication with coupling element 114 via stationary shaft 130. For some applications, as shown in FIGS. 12 and 13, rotating shaft 128 passes through stationary shaft 130 (unlike the configuration shown in FIGS. 9A-11D, in which stationary shaft 130 passes through rotating shaft 128). Rotating shaft 128 is in mechanical communication with rotating member 116 via a connecting element 140 that passes through stationary shaft 130, as shown in FIG. 13. Rotating and stationary sub-handles 124 and 126 typically are shaped so as to define respective knobs, to facilitate easy grasping by the surgeon. In the configuration shown in FIG. 12-14, unlike in the configuration shown in FIGS. 9A-11D, rotating sub-handle 124 is proximal to stationary sub-handle 126, i.e., the rotating sub-handle is farther from coupling element 114 than is the stationary sub-handle.

To use tool 110 to break delivery tube 50 from implant 30, the surgeon temporarily couples coupling element 114 to the proximal end of the implant. The surgeon holds stationary sub-handle 126 rotationally stationary, while at the same time rotating rotating sub-handle 124 (typically by between 180 and 360 degrees). This relative rotation pushes breaking element 118 against delivery tube 50, thereby breaking the delivery tube from the implant.

Rotation breaking tool 110, as described hereinabove with reference to FIGS. 4-6B, 7-8B, 9A-11D, and 12-14, is configured to stabilize implant 30 during the breaking of delivery tube 50 from the implant. During breaking, the surgeon holds handle 112 stable, which in turn holds coupling element 114 of tool 110 stable, and thereby stabilizes the implant to which the coupling element is coupled. Rotating member 116, when rotated, applies stress only between breaking element 118 and delivery tube 50.

In some applications of the present invention in which delivery tube 50 is initially coupled to implant 30 (such as by welding), the human hand of the surgeon grasps the delivery tube and applies the breaking torque to the delivery tube to decouple the distal tube end from the implant. Alternatively or additionally, the breaking torque is applied using a tool that is brought into contact with the delivery tube. Optionally, the tool may be configured to grasp the delivery tube; for example, the tool may comprise a needle holder, forceps, or tweezers.

Figures 15, 16:
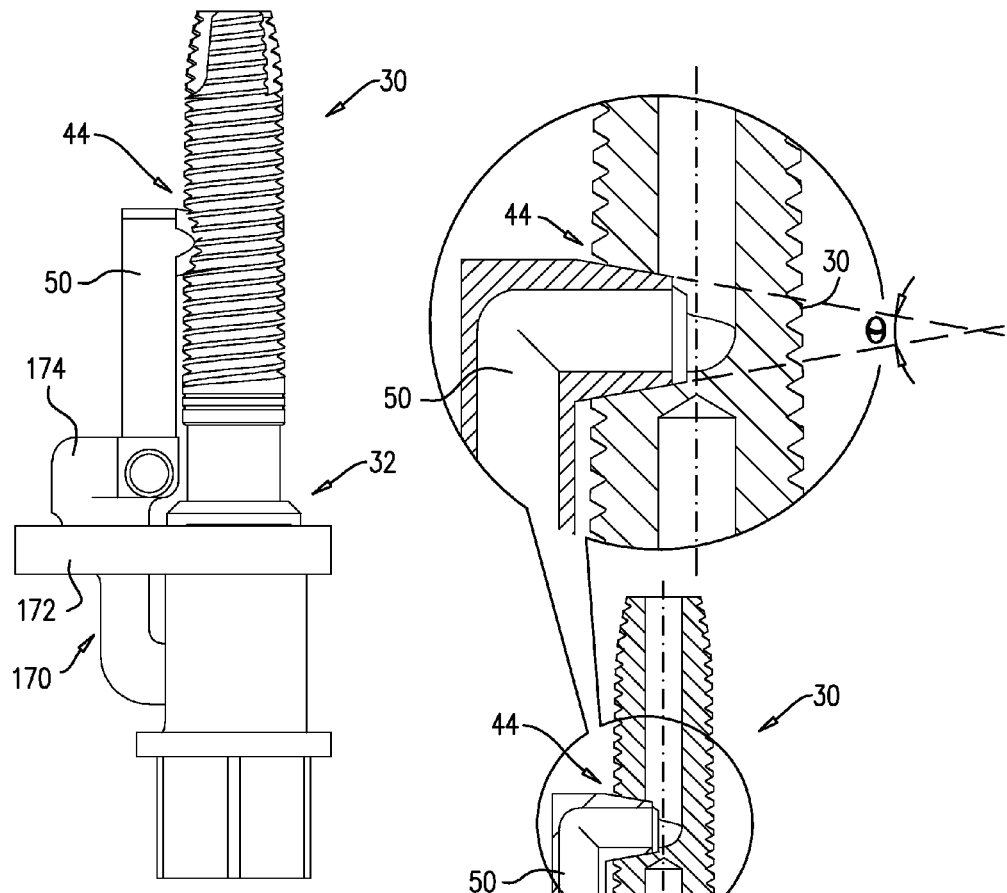
FIG. 15 is a schematic illustration of a dental implant and an applicator comprising a retaining element in a first position, in accordance with an application of the present invention.
FIG. 16 is a schematic cross-sectional illustration of the implant and applicator of FIG. 15, in accordance with an application of the present invention.

Reference is made to FIGS. 15, 16, 17A-E, and 18, which are schematic illustrations of dental implant 30 and applicator 32 comprising a retaining element 170, in accordance with an application of the present invention. FIG. 15 and FIG. 16 (a cross-section view of FIG. 15) show retaining element 170 in a first position in which the retaining element prevents the distal end of delivery tube 50 from separating from implant 30. Retaining element 170 thus holds the distal end of delivery tube 50 sealingly coupled to implant 30 such that the delivery tube is in fluid communication with lumen 40 of implant 30 via lateral opening 44 of implant 30. In this application, delivery tube 50 is not welded to implant 30. Retaining element nevertheless 170 provides a strong seal that is able to withstand the pressure of the fluid provided by fluid source 54 and the injection of a regenerative material, if performed. As can be seen in FIGS. 15 and 16, at least a portion of retaining element 170 is disposed remotely from lateral opening 44 when the retaining element is in the first position, e.g., at least 1 cm, such as 1.5 cm or 2 cm from lateral opening 44 when the retaining element is in the first position. Typically, at least a portion of (e.g., all of) retaining element 170 comprises one or more rigid materials, such as metal and/or plastic.

FIGS. 17A-E are views from respective directions in which retaining element 170 assumes a second position in which the retaining element does not prevent the distal tube end from separating from the implant, such that delivery tube 50 becomes decoupled from the implant. FIG. 18 is a cross-sectional view of FIG. 17A.

In this configuration, retaining element 170 is typically an integral part of applicator 32, e.g., applicator 32 is fixed to retaining element 170, and delivery tube 50 is coupled to retaining element 170. Implant 30 is typically packaged and provided to the surgeon pre-coupled to applicator 32, with the retaining element in the first position in which it prevents the distal end of the delivery tube from separating from the implant. The implant, applicator, and retaining element are configured such that the coupling of the applicator to the implant provides proper rotational orientation to precisely align the distal end of delivery tube 50 with lateral opening 44. After the dental implant has been screwed into the ridge, and fluid and/or regenerative material has been injected through delivery tube 50 and implant 30, the surgeon causes the retaining element to assume the second position, thereby decoupling the delivery tube from the implant.

Applicator 32 is typically removably coupled to the proximal end of implant 30, such as using coupling techniques described hereinabove with reference to FIGS. 1A-C. A proximal end of applicator 32 is typically shaped so as to define a coupling element, such as a male coupling element (as shown in FIGS. 15-18), e.g., a hexagonal head, or a female coupling element (configuration not shown), e.g., a hexagonal socket. Implant 30 may comprise a two-stage implant, or a single-stage transgingival implant, both of which are described hereinabove with reference to FIGS. 1A-C.

For some applications, the distal end of delivery tube 50 is shaped so as to define a cone. For example, as shown in FIG. 16, the cone may have an opening angle θ (theta) of between 0 and 90 degrees, such as between about 0 and about 60 degrees. For some applications, the cone forms a Morse taper, in which case the distal end of delivery tube 50 must be removed with force when retaining element 170 assumes the second position.

For some applications, retaining element 170 comprises a retaining element body 172, a pivoting element 174, and a proximal blocking element 176. Delivery tube 50 is coupled to the pivoting element. The pivoting element is configured to pivot with respect to the retaining element body, such that the delivery tube also pivots with respect to the retaining element body, and thereby with respect to applicator 32.

Blocking element 176 can be advanced distally and withdrawn proximally within applicator 32, such as by rotating the blocking element. When in a distal position, the blocking element prevents pivoting element 174 from pivoting freely, thereby causing retaining element 170 to assume the first position in which the retaining element prevents the distal end of delivery tube 50 from separating from implant 30. When in a proximal position, the blocking element does not interfere with the pivoting of pivoting element 174, thereby allowing retaining element 170 to assume the second position in which the retaining element does not prevent the distal end of delivery tube 50 from separating from implant 30.

Figure 17A:
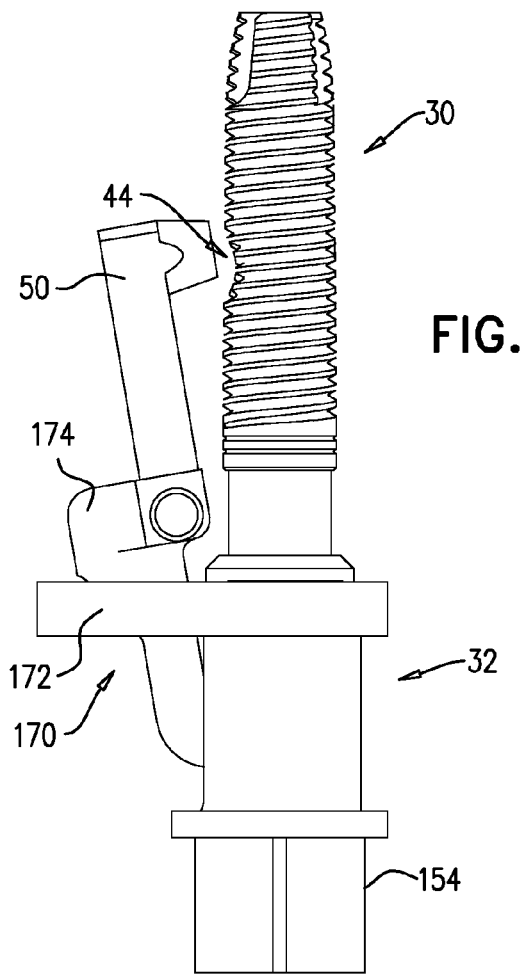
FIGS. 17A-E are schematic views from respective directions of the implant and applicator of FIG. 15 in a second position, in accordance with an application of the present invention.
Figure 17B:
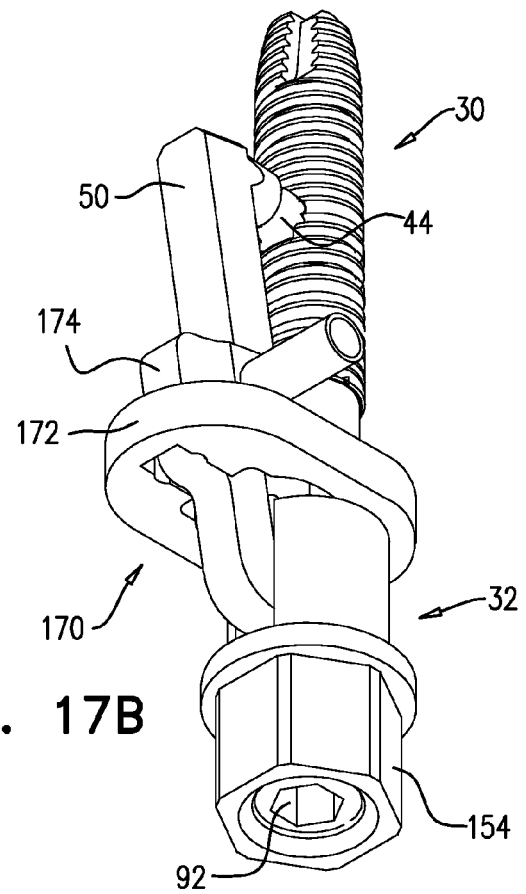
Figure 17C:
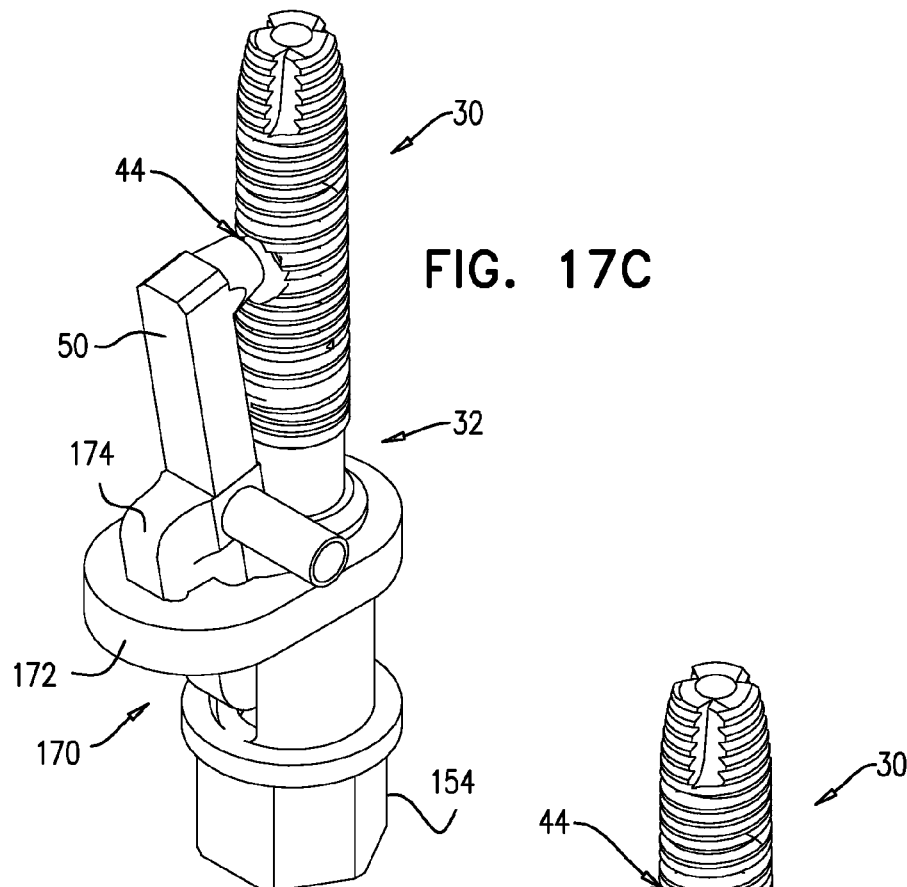
Figure 17D:
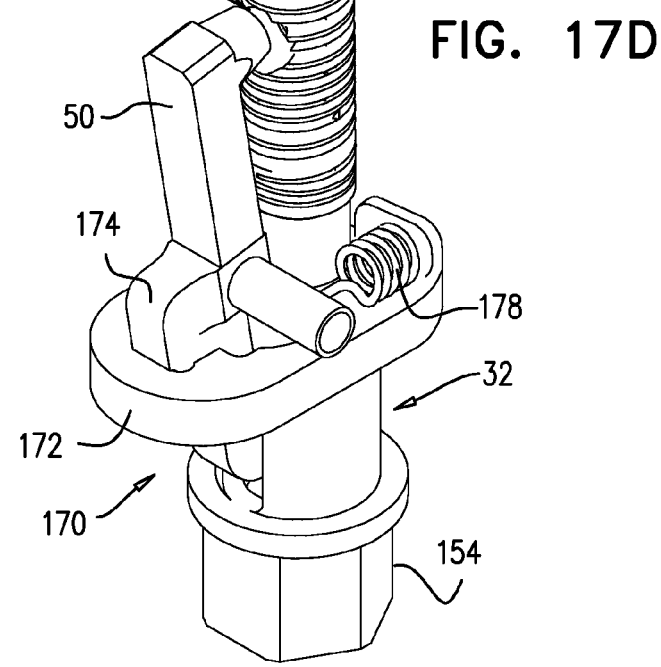
Figures 17E, 18:
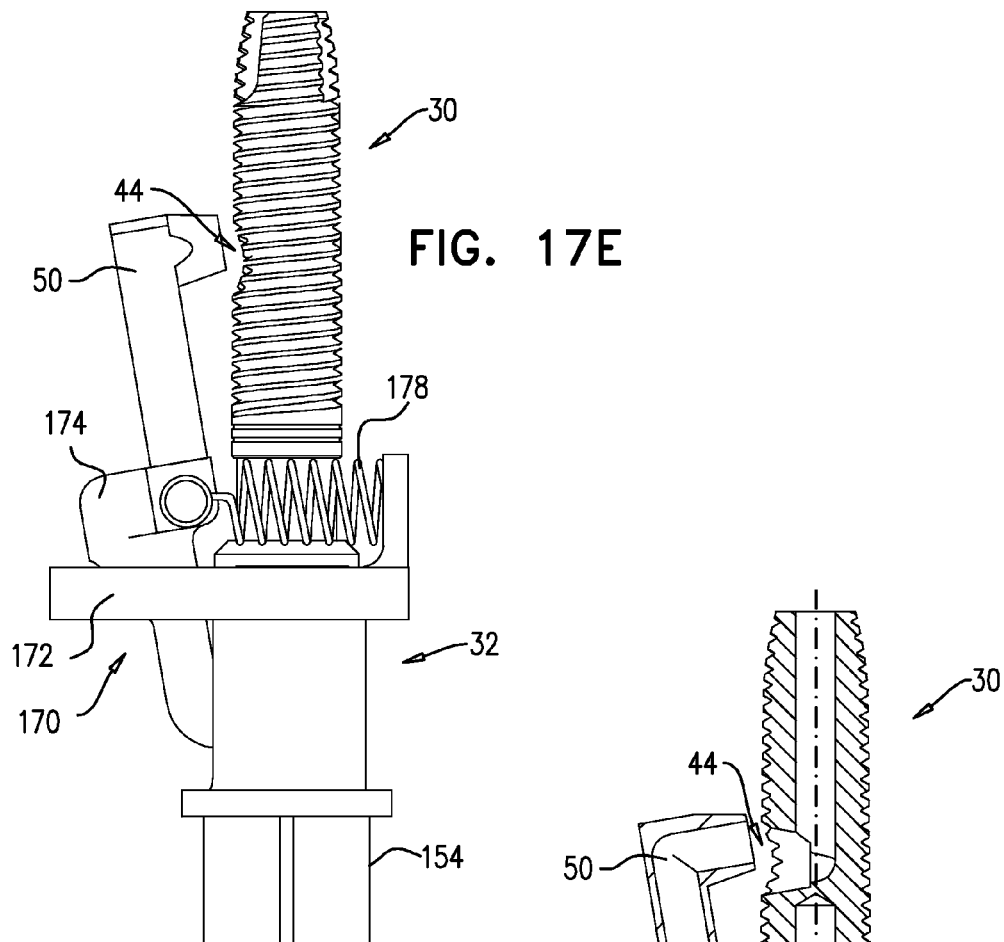
FIG. 18 is a schematic cross-sectional view of FIG. 17A, in accordance with an application of the present invention.

For some applications, as shown in FIGS. 17D-E, applicator 32 further comprises a spring 178, which is configured to apply a force that separates the distal tube end from the implant when the retaining element assumes the second position.

For some applications, the distal end of delivery tube 50 comprises a sealing element, which is configured to removably sealingly couple delivery tube 50 to lateral opening 44 of implant 30. For example, the sealing element may be configured as shown in and/or described hereinbelow with reference to FIGS. 19A-B or FIG. 30, or the sealing element may comprise an o-ring or a gasket.

Figure 19A:
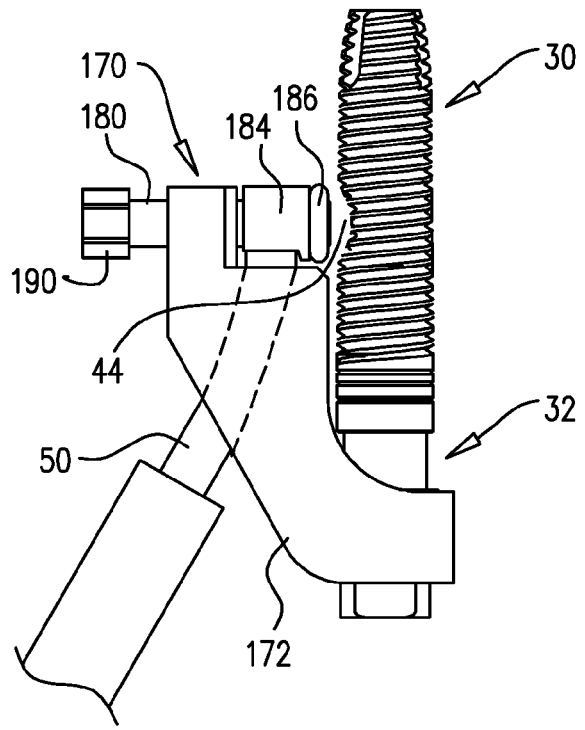
Figure 19B:
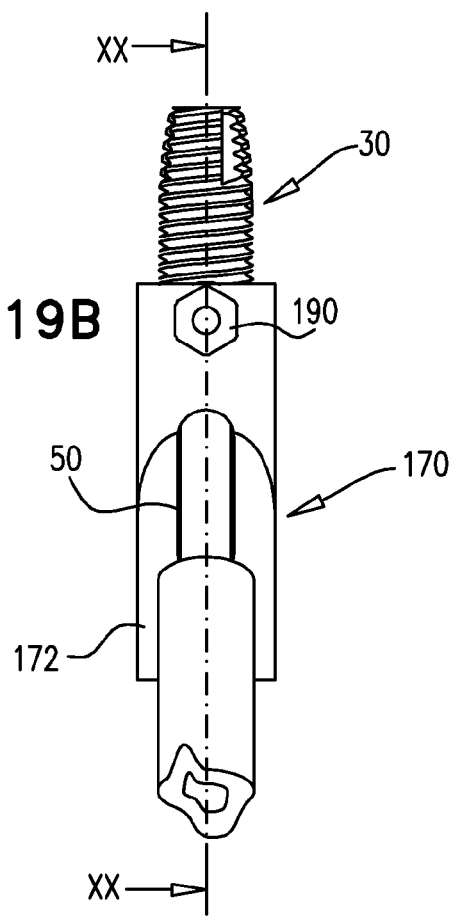

Reference is now made to FIGS. 19A-D, which are schematic illustrations of another configuration of dental implant 30, applicator 32, and retaining element 170, in accordance with an application of the present invention. FIGS. 19A-B and 19C are isometric and cross-sectional views, respectively, showing retaining element 170 in a second position (similar to the second position described hereinabove with reference to FIGS. 17A-E), in which the distal end of delivery tube 50 is not coupled to implant 30. FIG. 19D is a cross-sectional view showing retaining element 170 in a first position (similar to the first position described hereinabove with reference to FIGS. 15 and 16), in which the retaining element holds the distal end of the delivery tube sealingly coupled to implant 30 such that the delivery tube is in fluid communication with lumen 40 of the implant 30 via lateral opening 44 of implant 30. As can be seen in FIG. 19D, at least a portion of retaining element 170 is disposed remotely from lateral opening 44 when the retaining element is in the first position, e.g., at least 1 cm, such as 1.5 cm or 2 cm from lateral opening 44 when the retaining element is in the first position. Typically, at least a portion of (e.g., all of) retaining element 170 comprises one or more rigid materials, such as metal and/or plastic.

Applicator 32 is typically removably coupled to the proximal end of implant 30, such as using the coupling techniques described hereinabove with reference to FIGS. 1A-C. A proximal end of applicator 32 is typically shaped so as to define a coupling element, such as a male coupling element (as shown in FIGS. 19A-D), e.g., a hexagonal head, or a female coupling element (configuration not shown), e.g., a hexagonal socket. Implant 30 may comprise a two-stage implant, or a single-stage transgingival implant, both of which are described hereinabove with reference to FIGS. 1A-C.

In this application, delivery tube 50 is not welded to implant 30. Retaining element nevertheless 170 provides a strong seal that is able to withstand the pressure of the fluid provided by fluid source 54 (as described hereinbelow with reference to FIG. 26B) and the subsequent injection of a regenerative material, if performed.

In this configuration, retaining element 170 and applicator 32 are typically provided as separate components of dental implant system 20, that are removably coupled to each other by the surgeon during a dental procedure. Delivery tube 50 is coupled to retaining element 170. Implant 30 is typically packaged and provided to the surgeon pre-coupled to applicator 32, while retaining element 170 is provided separately, not coupled to the applicator or implant. Alternatively, the surgeon couples applicator 32 to implant 30 during the implantation procedure. After the dental implant has been screwed into the ridge, such as described hereinbelow with reference to FIG. 26A, the surgeon attaches retaining element 170 to applicator 32, with the retaining element in the second position, such as described hereinbelow with reference to FIG. 26B. The surgeon then causes the retaining element to assume the first position, thereby coupling the delivery tube to the implant. The implant, applicator, and retaining element are configured such that the coupling of the applicator to the implant provides proper rotational and longitudinal orientation to precisely align the distal end of delivery tube 50 with lateral opening 44.

The surgeon injects fluid and/or regenerative material through delivery tube 50 and implant 30. The surgeon decouples the delivery tube from the implant, removes the retaining element from the applicator, and then removes the applicator from the implant.

For some applications, retaining element 170 comprises retaining element body 172, a portion of which is configured to be disposed alongside implant 30 from applicator 32 to lateral opening 44 of implant 30. Optionally, the proximal end of applicator 32 slightly protrudes proximally from retaining element body 172, as shown in FIGS. 19A-D. For some applications, retaining element 170 further comprises a shaft 180, a first end of which serves as the distal end of delivery tube 50, and is shaped so as to provide a coupling port 184 for delivery tube 50. The shaft is configured to sealingly couple the coupling port to lateral opening 44 of implant 30. To this end, the coupling port 184 (i.e., the distal end of delivery tube 50) typically comprises a sealing element 186. For example, the sealing element may be configured as described hereinbelow with reference to FIG. 30, or the sealing element may comprise an o-ring or a gasket. The shaft is typically oriented such that a longitudinal axis thereof forms an angle of 90 degrees with the longitudinal axis of the implant, e.g., 90 degrees. As is shown in FIGS. 19A-D, when retaining element 170 is in the first and the second positions, shaft 180 and the distal end of delivery tube 50 are positioned at a same circumferential side of implant 30 (e.g., the left side in FIG. 19A, and the right side in FIGS. 19C-D).

For some applications, shaft 180 is configured such that rotation of a portion thereof brings coupling port 184 (and the distal tube end) into contact with lateral opening 44 of implant

30. For example, an external surface of a portion of shaft 180 may be shaped so as to define a screw thread 188, which passes through a lumen of retaining element body 172 that is shaped so as to define a corresponding screw thread. The end of shaft 180 opposite the end that provides coupling port 184 is typically shaped so as to define a knob 190, for facilitating rotation of the shaft 180 by the surgeon.

For some applications, implant 30 comprises a removable plug that is configured to seal lateral opening 44. The plug is removed before retaining element 170 is applied to couple the distal end of delivery tube 50 to implant 30.

For some applications, the distal end of delivery tube 50 is shaped so as to define a cone, such as described hereinabove with reference to FIG. 16. For example, the cone may have an opening angle of between 0 and 90 degrees, such as between 0 and 60 degrees.

For some applications, retaining element 170 is configured to be coupled directly to dental implant 30, rather than to applicator 32. For these applications, retaining element 170 is typically removably coupled to the proximal end of implant 30, such as using the coupling techniques for coupling applicator 32 to implant 30, described hereinabove with reference to FIGS. 1A-C, mutatis mutandis. A surface of retaining element 170 is typically shaped so as to define a coupling element, such as a male coupling element, e.g., a hexagonal head, or a female coupling element, e.g., a hexagonal socket. For example, retaining element 170 may comprise and be fixed to the component that is shown as applicator 32 in FIG. 19A-D.

For these applications, applicator 32 still may be provided for use in one or more steps of an implantation procedure before the retaining element is coupled to the dental implant (but not for coupling the retaining element to the implant). For example, applicator 32 may be used for the step of the implantation procedure described hereinbelow with reference to FIG. 26A. The applicator is decoupled from the implant before coupling the retaining element to the dental implant, for performing the step of the procedure described hereinbelow with reference to FIG. 26B.

Reference is now made to FIGS. 20A-G, which are schematic illustrations of yet another configuration of dental implant 30, applicator 32, and retaining element 170, in accordance with an application of the present invention. FIGS. 20A-B and 20E-F are isometric views showing retaining element 170 in a second position (similar to the second position described hereinabove with reference to FIGS. 17A-E and FIGS. 19A-B and 19C), in which the distal end of delivery tube 50 is not coupled to implant 30. FIGS. 20C-D are isometric views showing retaining element 170 in a first position (similar to the first position described hereinabove with reference to FIGS. 15 and 16 and FIG. 19D), in which the retaining element holds the distal end of the delivery tube sealingly coupled to implant 30 such that the delivery tube is in fluid communication with lumen 40 of the implant 30 via lateral opening 44 of implant 30. Another view of this configuration of retaining element 170 is provided in FIG. 30, which is described hereinbelow. As can be seen in FIGS. 20C-D, at least a portion of retaining element 170 is disposed remotely from lateral opening 44 when the retaining element is in the first position. For example, at least a portion of retaining element 170 may be disposed at least 1 cm, such as 1.5 cm or 2 cm from lateral opening 44 when the retaining element is in the first position. Typically, at least a portion of (e.g., all of) retaining element 170 comprises one or more rigid materials, such as metal or plastic.

Except as described hereinbelow, this configuration of dental implant 30, applicator 32, and retaining element 170 is generally similar to, and may incorporate any of the features of, the configuration described hereinabove with reference to FIGS. 19A-D. For some applications, a proximal end of delivery tube 50 is coupled to a fluid source, e.g., fluid source 54, such as manual syringe 56 (described hereinabove with reference to FIG. 1B), by a luer lock, which is located remotely from implant 30. A luer lock may also be used to couple the distal end of the delivery tube to a fluid source in the other configurations described herein, including, but limited to, the configuration described with reference to FIGS. 19A-D.

In this configuration, retaining element 170 and applicator 32 are typically provided as separate components of dental implant system 20, that are removably coupled to each other by the surgeon during a dental procedure. Delivery tube 50 is coupled to retaining element 170. Implant 30 is typically packaged and provided to the surgeon pre-coupled to applicator 32, while retaining element 170 is provided separately, not coupled to the applicator or implant. Alternatively, the surgeon couples applicator 32 to implant 30 during the implantation procedure. After the dental implant has been screwed into the ridge, such as described hereinbelow with reference to FIG. 26A, the surgeon attaches retaining element 170 to applicator 32, with the retaining element in the second position, as shown in FIG. 20B, and such as described hereinbelow with reference to FIG. 26B. The surgeon then causes the retaining element to assume the first position, thereby coupling the delivery tube to the implant, as shown in FIG. 20C. The implant, applicator, and retaining element are configured such that the coupling of the applicator to the implant provides proper rotational and longitudinal orientation to precisely align the distal end of delivery tube 50 with lateral opening 44.

The surgeon injects fluid and/or regenerative material through delivery tube 50 and implant 30. The surgeon decouples the delivery tube from the implant, removes the retaining element from the applicator, as shown in FIGS. 20D-F. The surgeon then decouples the applicator from the implant, as shown in FIG. 20G. For example, the surgeon may decoupled connecting element 98 from the applicator and the implant, such as described hereinbelow with reference to FIGS. 21A-D, 22A-B, 23, and 24.

For some applications, retaining element 170 comprises retaining element body 172, a portion of which is configured to be disposed alongside implant 30 from applicator 32 to lateral opening 44 of implant 30. Optionally, the proximal end of applicator 32 slightly protrudes proximally from retaining element body 172, as shown in FIGS. 20A-G.

For some applications, retaining element 170 further comprises a shaft 182. The shaft is configured to couple retaining element 170 to implant 30, such that the distal end of delivery tube 50 is removably sealingly coupled to lateral opening 44 of implant 30. To this end, the distal end of delivery tube 50 typically comprises a sealing element 187. For some applications, sealing element 187 is configured as described hereinbelow with reference to FIG. 30. Alternatively, the sealing element may comprise an o-ring or a gasket. The shaft is typically oriented such that a longitudinal axis thereof forms an angle of 90 degrees with the longitudinal axis of the implant, e.g., 90 degrees.

For some applications, retaining element 170 is configured such that when the retaining element is in the first position (coupled to implant 30), shaft 182 and the distal end of delivery tube 50 are positioned at circumferentially opposite sides of implant 30, albeit typically at different longitudinal positions along the implant (the shaft is typically positioned longitudinally proximal to the delivery tube end). For some applications, during an implantation procedure, shaft 182 (and knob 190) are positioned at the palatal aspect of the ridge.

For some applications, shaft 182 is configured such that rotation thereof in a first direction, as symbolically indicated by a clockwise arrow 183 in FIG. 20C, transitions the retaining element from the second (uncoupled) position to the first (coupled) position, thereby coupling the retaining element to the implant, and bringing the distal tube end into contact with lateral opening 44 of implant 30, as shown in FIG. 20C. Rotation of the shaft in a second direction opposite the first direction, as symbolically indicated by a clockwise arrow 185 in FIG. 20D, transitions the retaining element from the first position to the second position, thereby decoupling the retaining element from the implant. For example, an external surface of a portion of shaft 182 may be shaped so as to define screw thread 188, which passes through a lumen of retaining element body 172 that is shaped so as to define a corresponding screw thread. The end of shaft 182 near the implant pushes against a lateral surface of the applicator (as shown) or of the implant (configuration not shown), thereby drawing the distal tube end, which is disposed on the opposite side of the retaining element, toward opening 44. The end of shaft 182 away from the implant is typically shaped so as to define knob 190, for facilitating rotation of the shaft 182 by the surgeon.

Figure 22A:
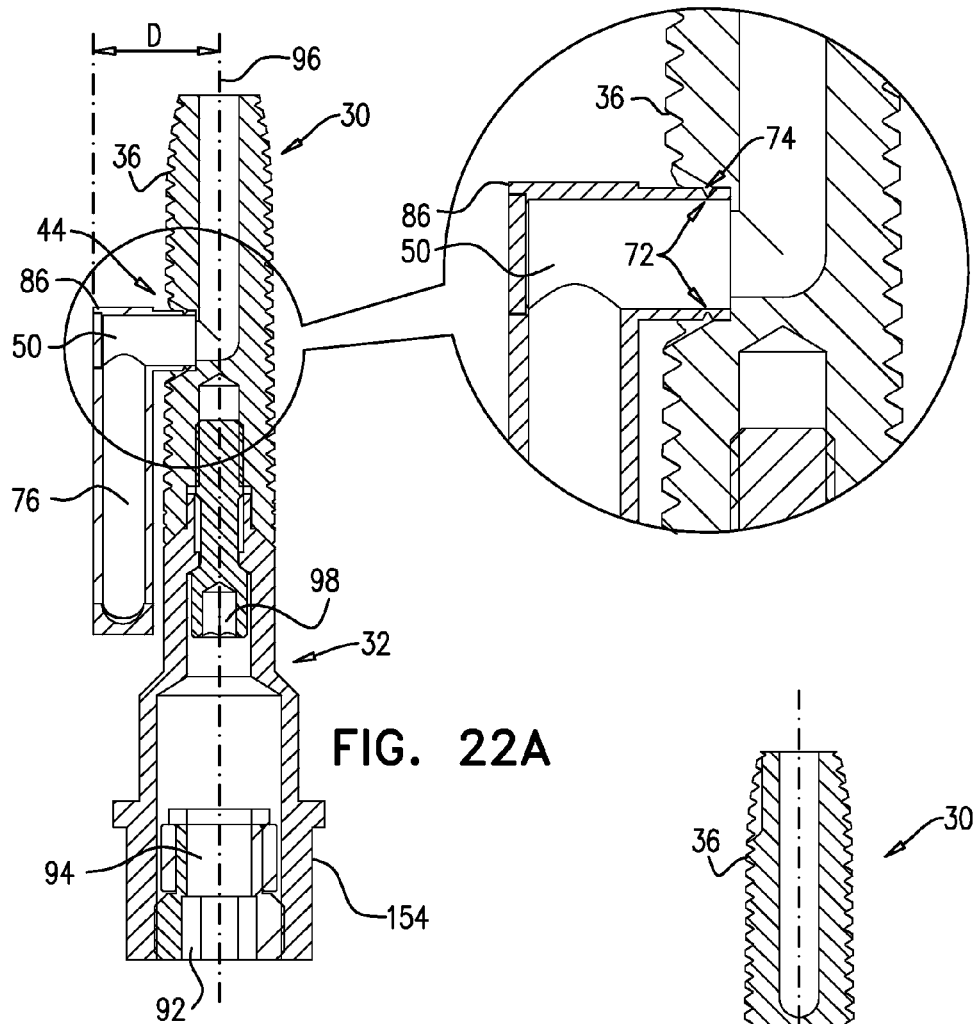
Figure 22B:
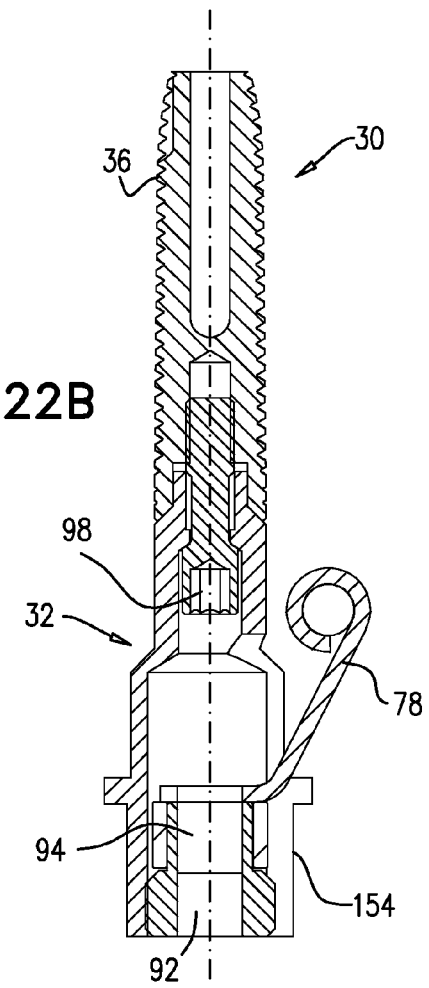
Figure 23:
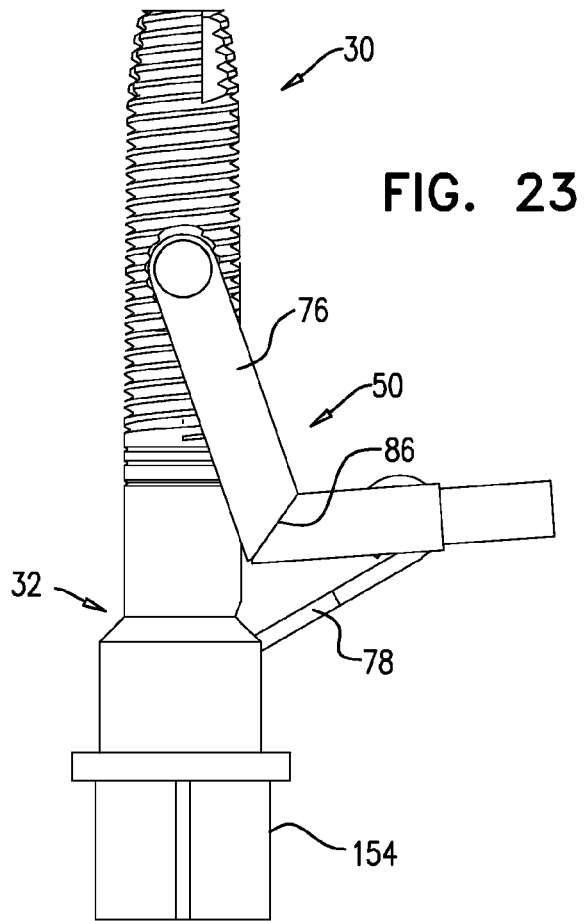
Figure 24:
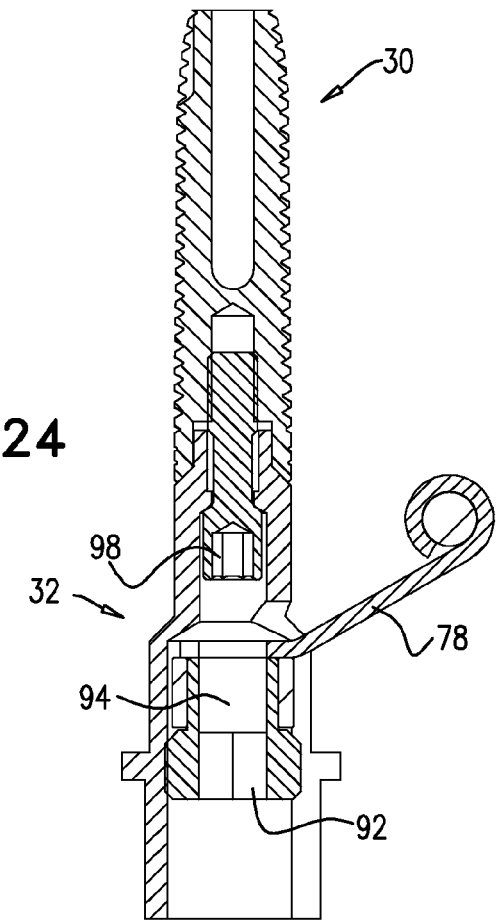

Reference is made to FIGS. 21A-D, 22A-B, 23, and 24, which are schematic illustrations of dental implant 30 and applicator 32 in which the distal end of delivery tube 50 is initially welded to implant 30, in accordance with an application of the present invention. In this configuration of system 20, applicator 32 is configured to break delivery tube 50 from the implant. FIGS. 21A-D are views from respective directions of the implant and applicator in which delivery tube 50 is coupled to the implant, such that the delivery tube is in fluid communication with lumen 40 of implant 30 via lateral opening 44 of implant 30. FIGS. 22A-B are cross-sectional views taken along lines IVA-IVA and IVB-IVB of FIG. 21A, respectively. FIG. 23 shows the implant and applicator after the delivery tube has been broken, as described hereinbelow, and FIG. 24 is a cross-sectional view of FIG. 23.

Applicator 32 is typically removably coupled to the proximal end of implant 30, such as using coupling techniques described hereinabove with reference to FIGS. 1A-C. A proximal end of applicator 32 is typically shaped so as to define a coupling element, such as a male coupling element (as shown in FIGS. 3A-6), e.g., a hexagonal head, or a female coupling element (configuration not shown), e.g., a hexagonal socket. Implant 30 may comprise a two-stage implant, or a single-stage transgingival implant, both of which are described hereinabove with reference to FIGS. 1A-C.

For some applications, applicator 32 is configured to break delivery tube 50 at thinner portion 72 by rotating the distal end of the delivery tube with respect to lateral opening 44 of the implant. Typically, applicator 32 is configured to apply a torque of greater than 50 Newton centimeters to the delivery tube, when rotating the distal tube end with respect to the lateral opening. The applicator typically applies the torque to the delivery tube without applying any meaningful torque to the implant itself, and thus does not dislodge or misalign the implant, which has been precisely placed in a bore in the ridge. For some applications, a distal portion 76 of delivery tube 50 is initially positioned generally parallel to central longitudinal axis 96 of implant 30 before thinner portion 72 is broken, as shown in FIGS. 21A-D and 22A-B. Applicator 32 rotates the distal end of the delivery tube by rotating portion 76 between about 5 and about 20 degrees, e.g., about 10 degrees, until thinner portion 72 breaks, as shown in FIGS. 5 and 6.

For some applications, applicator 32 comprises a lever arm 78, which is coupled to delivery tube 50 and arrange to rotate the distal tube end with respect to lateral opening 44. For some applications, the delivery tube is shaped so as to define bend 86 at between about 5 and about 20 mm from the distal tube end, and lever arm 78 is coupled to the delivery tube at a location proximal to the bend. For these applications, the bend typically has an angle of between 85 and 180 degrees. For some applications, applicator 32 comprises a rotatable surface 92 accessible from a proximal end of the applicator, which rotatable surface is rotatable with respect to a portion of the applicator. Rotation of rotatable surface 92 rotates the distal tube end by extending lever arm 78. For example, rotation of the rotatable surface may distally advance a transfer element 94 that extends the lever arm. For example, rotatable surface 92 may define an internal hex, e.g., having an internal width of about 2.4 mm (the hex width is the distance between parallel sides of the hexagon).

For some applications, applicator 32 comprises a connecting element 98, which removably couples the applicator to the proximal implant end. For some applications, the connecting element comprises a connecting screw; for example, the connecting element may comprise a shaft, at least a portion of which defines a screw thread. Typically, the head of connecting element 98 is accessible from a channel than passes through rotatable surface 92, such that the head can be rotated with a screwdriver tool inserted through the proximal end of the applicator, in order to decouple the applicator from the implant. For example, the connecting screw may define an internal hex that has an internal width less than that of rotatable surface 92, e.g., about 1.25 mm. For some applications, the applicator is configured such that rotation of rotatable surface 92 both (a) applies the breaking torque to the delivery tube that breaks the delivery tube at the thinner portion, and (b) rotates connecting element 98 to decouple the applicator from the proximal implant end.

For other applications, the connecting element does not comprise a screw, and instead comprises one or more surfaces, such as conical surfaces, that are configured to removably couple the applicator to the proximal implant end by friction. For example, the applicator may comprise a male coupling element, that is configured to be coupled to a female coupling element of the implant.

Reference is made to FIGS. 25A-G, which are schematic illustrations of several steps of a minimally-invasive closed sinus lift surgical procedure for implanting dental implant 30, in accordance with an application of the present invention. The procedure is typically employed when a patient's maxillary alveolar ridge lacks sufficient bone mass to support a conventional dental implant. The procedure is particularly appropriate for implanting the configuration of implant 30 described hereinabove with reference to FIGS. 1A-C, optionally in combination with one or more of the features described hereinabove with reference to FIGS. 2A-C, 3A-B, 3C-D, and/or 28A-B.

Figure 25A:
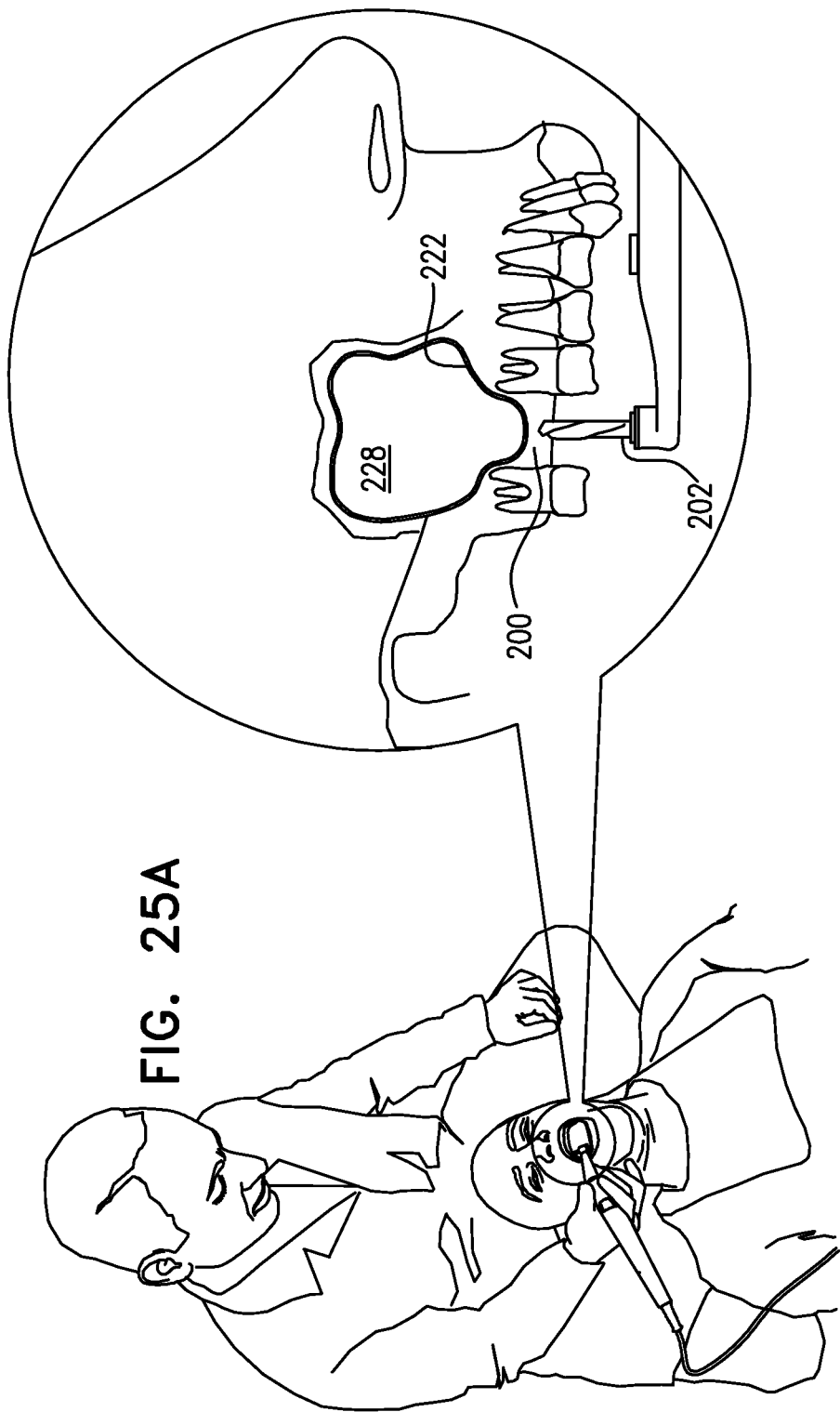

A surgeon begins the procedure by preparing the oral facial region, and administering a local anesthetic. Optionally, as shown in FIG. 25A, the surgeon initiates an osteotomy in a maxillary alveolar ridge 200 by making a preliminary portion of a bore using a dental drill, such as a conventional sinus bur 202. This preliminary bore portion typically has a diameter of between about 1 and about 7 mm, e.g., between about 2 and about 6 mm, and leaves residual bone thickness of between about 0.5 and about 5 mm, e.g., between about 1 and about 4 mm, or between about 0.5 and about 2 mm, e.g., between about 1 and about 2 mm. Optionally, the surgeon widens the bore using a series of successively wider drill bits, until a desired bore diameters is achieved (for example, the largest drill bit may have a diameter of 3.65 mm for an implant having a diameter of 4.2 mm, or a diameter of 4.2 mm for an implant having a diameter of 5 mm). The bore may be measured using techniques known in the art, such as CT, x-ray, or x-ray with a depth guide. For some applications, a surgical guide is used to ensure clearance between the center of the osteotomy and the nearest tooth surfaces. Optionally, a pre-surgery radiograph (e.g., CT or x-ray) is performed, in order to enable the surgeon to estimate the height of the residual bone and plan the osteotomy accordingly.

For some applications, the surgeon uses a surgery guidance system for ensuring that the osteotomy is drilled to the requisite depth. For example, the surgeon may use Nobel Guide™ (Nobel Biocare, Zurich, Switzerland) or Simplant® dental software (Materialise Dental NV, Leuven, Belgium). These techniques use a combination of computerized models with physical surgical guiding devices to allow the dentist to drill an osteotomy at the requisite location, angulation, and depth.

Figure 25C:
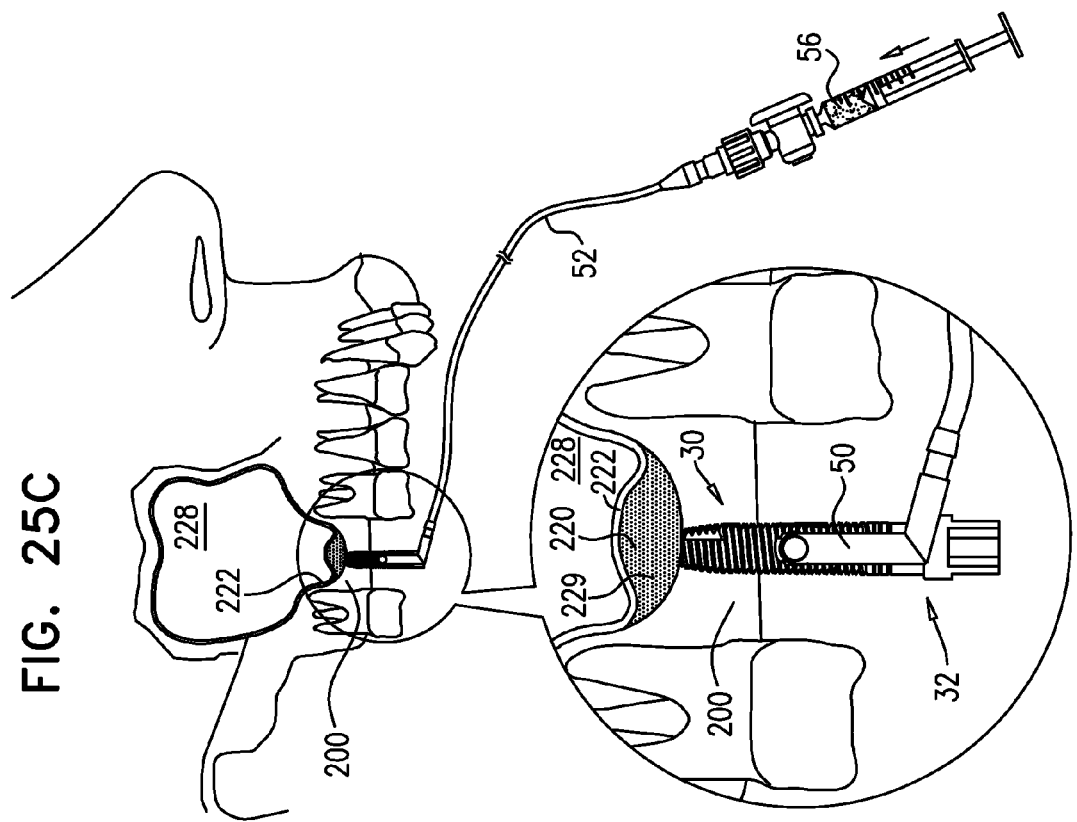
Figure 25B:
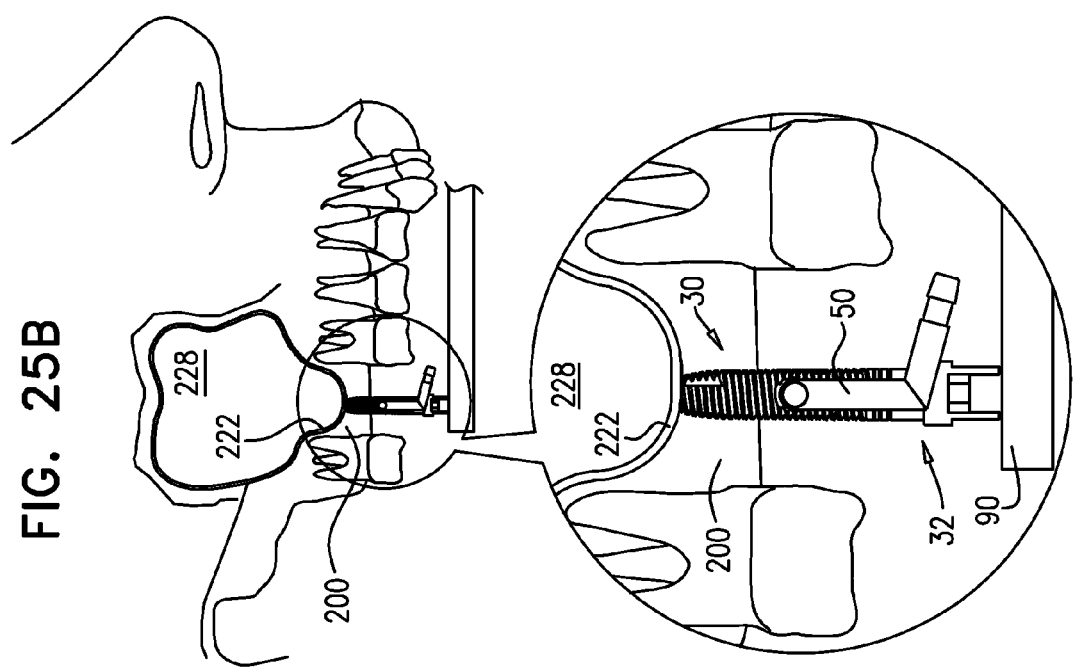

After drilling the preliminary bore portion, the surgeon advances dental implant 30 into the bore by screwing the implant into ridge 200 using surgical rotation tool 90 (described hereinabove with reference to FIGS. 1A and 1C), as shown in FIG. 25B. The surgeon typically screws the implant until distal implant end 38 reaches the end of the osteotomy. The surgeon then advances the implant slightly (typically, by about one additional rotation), causing the implant to break through the top of ridge 200 to below a Schneiderian membrane 222, thereby bringing distal opening(s) 41 into fluid communication with a surface of the membrane facing ridge 200, as shown in FIG. 25B. Distal implant end 38 typically does not pass through the top of ridge 200, at least at this stage in the procedure.

Optionally, after the initial insertion of the implant into the bore, the surgeon uses a periapical radiograph to estimate remaining distance from implant tip to the sinus floor. The surgeon rotates the implant to penetrate into the sinus, such as by rotating the implant by a number of rotations equal to the remaining distance divided by a constant, e.g., 1.2 mm. Optionally, the surgeon performs an additional periapical radiograph to ensure that the implant has penetrated into the sinus cavity.

After the implant has been advanced to membrane 222, the surgeon decouples rotation tool 90 from applicator 32, and couples supply tube 52 to the proximal end of delivery tube 50, as shown in FIG. 25C. The surgeon gently lifts and separates membrane 222 from the top of ridge 200 into a maxillary sinus 228, by injecting a fluid 229, such as a biocompatible solution such as normal saline solution or a gas, from fluid source 54 (optionally, under controlled pressure) via supply tube 52, delivery tube 50, and lumen 40, so as to form a cavity 220 under the membrane between the ridge and the membrane (in FIG. 25C, the membrane is shown partially raised). Typically, the surgeon injects sufficient fluid 229 into cavity 220 to inflate the cavity to a vertical height of between about 2 and about 20 mm from the top of ridge 200, such as between about 2 and about 11 mm, e.g., between about 2 and about 8 mm For some applications, a measured volume of fluid 229 is injected in order to achieve the desired cavity height, such as between about 0.5 and about 6 ml of fluid, e.g., between about 1 and about 4 ml, between about 1 and about 3 ml, or between about 2 and about 4 ml.

For some applications, the fluid is drained from the cavity. For some applications, the surgeon detects that membrane 222 has detached from the top of ridge 200 by observing blood within the drained fluid 229. The membrane bleeds as it detaches because of the hydraulic pressure of fluid 229. Blood flows into the fluid and may be observed in supply tube 52 and/or fluid source 54, e.g., syringe 56. The presence of this blood serves as positive indication that the distal end of the implant has reached the sinus and the membrane has separate from the ridge. If blood is not seen, the surgeon may inject additional fluid and/or advance the implant farther into the ridge. Optionally, the surgeon may instruct the patient to sit up as well, to enhance the return of fluid from the cavity.

For some applications, after draining the fluid from the cavity, the surgeon injects a regenerative material 230, such as liquid or gel bone graft, into cavity 220, as shown in FIG. 25D. Fluid source 54 or a separate syringe or powered drug delivery device is used for injecting the regenerative material. If a separate syringe or device is used to inject the material, the material may be provided via supply tube 52, or via a separate supply tube coupled to the proximal end of delivery tube 50. Regenerative material 230 may comprise an allograph, an autogeneous bone graft, or a xenograft, and may, for example, comprise a natural material, a synthetic material, or a mixture thereof. For example, regenerative material 230 may comprise one of the following commercially available fluid bone graft materials: DBX Paste (MTF), Allomatrix (Wright), Cerament (Bone Support), DynaGraft (Citagenix/ISOTIS), Fisiograft (Ghimas), Grafton (Osteotech), Optium DBM Gel (Lifenet/Depuy J&J), OsteoMax (Orthfix), PD VitalOs Cemen (VitalOs), or Regenafil® (Exactech). Alternatively, regenerative material 230 may comprise the composition described hereinbelow that comprises saline solution mixed with solid bone graft particles. Optionally, the system monitors and generates an output indicative of the pressure of the regenerative material as it is injected.

For some applications, system 20 measures the volume of fluid 229 injected into the cavity between the ridge and the membrane while forming cavity 220, at the step of the procedure described hereinabove with reference to FIG. 25C. Responsively to the measured volume, the surgeon determines an amount of regenerative material 230 to inject into cavity 220 at the step of the procedure described hereinabove with reference to FIG. 25D. Typically, the amount of regenerative material 230 is approximately equal to the volume of injected fluid 229, or slightly greater or less than the volume of the injected fluid. As a result, waste of regenerative material 230 is generally minimized, and the likelihood of perforating the membrane by injection of the regenerative material is generally reduced.

For some applications, the surgeon uses a flexible wire as a piston to help push the regenerative material through the supply tube and/or lumen. This technique may be helpful when the regenerative material is viscous and thus difficult to inject using an ordinary syringe.

Alternatively, for some applications, regenerative material 230 is not injected into the cavity, i.e., the step of the procedure described hereinabove with reference to FIG. 25D is omitted. Fluid 229, which may comprise saline solution, is left in cavity 220, or, alternatively, is drained from the cavity. Recent research has shown that elevation of the Schneiderian membrane and subsequent support thereof in a tented position promotes new bone formation even without the introduction of bone regenerative material (for example, see the above-mentioned article by Pjetursson et al., which is incorporated herein by reference). If fluid 229 is left in place in the cavity, the fluid holds the membrane in the raised position. If the fluid is drained, implant 30, when advanced as described hereinbelow with reference to FIG. 25F, holds the membrane in the raised position.

Further alternatively, at the step described hereinabove with reference to FIG. 25D, instead of injecting regenerative material 230, the surgeon injects an alternative therapeutic material, such as one or a mixture of more than one of the following materials: a bone growth stimulating substance, such as a bone morphogenetic protein (BMP), and blood.

Still further alternatively, the surgeon injects regenerative material 230, rather than fluid 229, to lift membrane 222, thereby combining the steps of the procedure described hereinabove with reference to FIGS. 25C and 25D. In this case, the regenerative material typically comprises a liquid.

As shown in FIG. 25E, the surgeon breaks delivery tube 50 from implant 30, for example using one of the tools described hereinabove with reference to FIG. 4-6B, 7-8B, 9A-11D, or 12-14. Before coupling the tool to the implant, the surgeon decouples applicator 32 from the implant, for example using a driver tool, e.g., similar to driver 262 described hereinbelow with reference to FIG. 27C. (For applications in which implant 30 implements the techniques described hereinabove with reference to FIG. 3A-B or 3C-D, such decoupling additionally allows rotation of delivery tube 50 and breaking thereof from the implant.) Optionally, the surgeon is provided with more than one of these tools, and selects the tool that is most convenient to use based on the location of the implant in the patient's oral cavity, and the particular characteristics of the patient and the surgical procedure. The surgeon may break delivery tube 50 from implant 30 before or after decoupling supply tube 52 from the proximal end of delivery tube 50, as decided by the surgeon based on surgical conditions. After breaking the delivery tube from the implant, the surgeon decouples the tool from the implant.

After decoupling delivery tube 50 from implant 30, the surgeon further advances (e.g., by rotating or screwing) implant 30 into regenerative material 230 in cavity 220, as shown in FIG. 25F. For example, the surgeon may use the same surgical rotation tool 90 described hereinabove with reference to FIG. 25B, by coupling the rotation tool to the proximal coupling element defined by implant 30. This additional advancing of the implant advances lateral surface 42 of implant 30 at least until lateral opening 44 is positioned entirely within the bore in ridge 200 and/or in regenerative material 230 in cavity 220. Such positioning of both ends of lumen 40 within bone substantially reduces the risk of infection, because proximal end 34 of implant 30 that is exposed to the oral cavity or gingiva is permanently closed. Typically, the surgeon couples a cover screw to the proximal end of the implant using a hand driver, and sutures the gingiva.

For some applications, after decoupling delivery tube 50 from implant 30 and before further advancing the implant, the surgeon plugs lateral opening 44 of implant 30, using a plug (configuration not shown). The plug may be configured to be (a) screwed in, (b) pushed in by friction or a Morse taper, and/or (c) glued in using a cement or adhesive. Alternatively or additionally, the plug may comprise a cement or adhesive material that solidifies in opening 44. Optionally, the outer surface of the plug is treated using known techniques for implant surface treatment to enhance osseointegration.

As shown in FIG. 25G, after bone grows in cavity 220 (into regenerative material 230, if injected) and is integrated into ridge 200, an appliance 140, such as a crown, is coupled to implant 30, typically using an abutment 242 coupled to implant 30, as is known in the art. Alternatively, as mentioned above, implant 30 comprises a single-stage transgingival implant/abutment, as is known in the art.

Figure 25H:
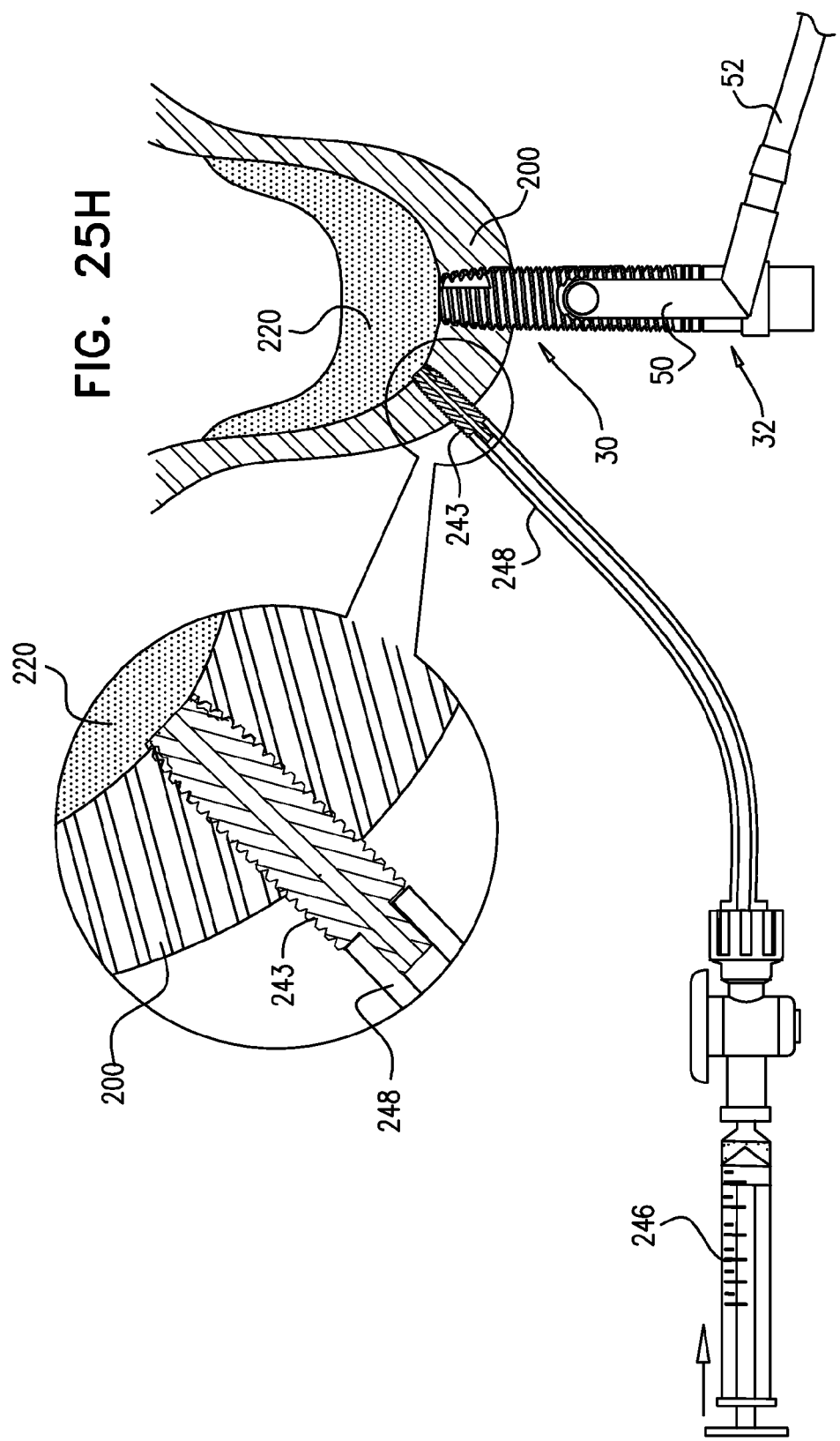
Figure 25J:
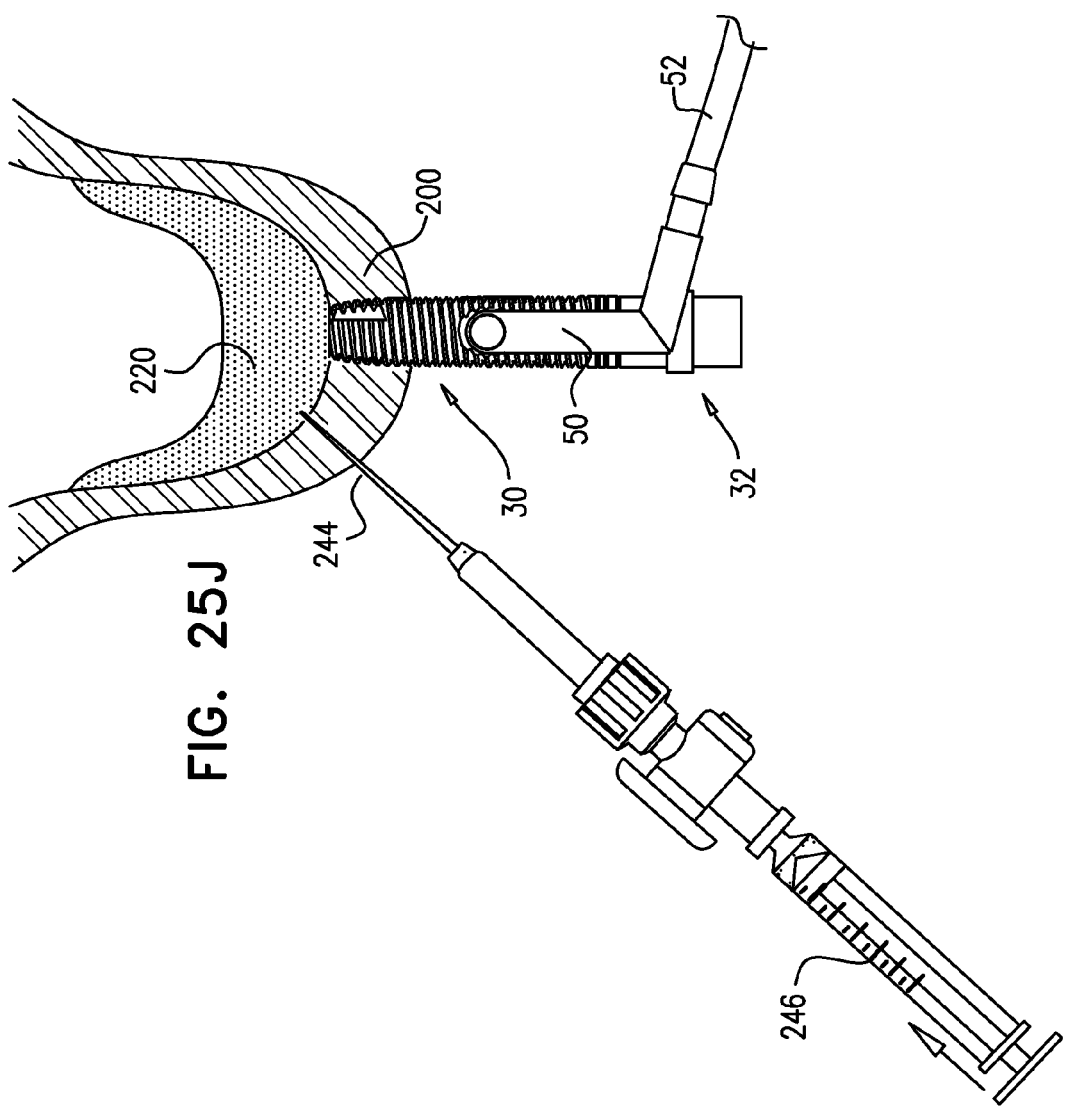

Reference is made to FIGS. 25H-J, which are schematic cross-sectional illustrations of alternative techniques for injecting regenerative material 230, taken along line XXVH-XXVH of FIG. 25D, in accordance with respective applications of the present invention. These techniques are used instead of or in addition to the injection technique described hereinabove with reference to FIG. 25D. In these techniques, after membrane 222 has been lifted from the top of ridge 200, as described hereinabove with reference to FIG. 25C, the surgeon forms a second bore through the ridge at a second bore location, e.g., using a dental drill. The second bore location is typically at least 1 mm, such as at least 2 mm or at least 3 mm, from a first bore location of the bore described hereinabove with reference to FIG. 25C. The surgeon injects regenerative material 230 into cavity 220, typically using a separate syringe 246 or powered drug delivery device, via a supply line 248.

For some applications, as shown in FIGS. 25H and 25I, the surgeon injects the regenerative material by inserting an adaptor 243 into the second bore. The adaptor is shaped so as to define a channel therethrough. Supply line 248 is coupled to the proximal end of the channel. For example, adaptor 243 may be threaded, as shown in FIG. 25H, in which case the surgeon screws the adaptor into the second bore. In this configuration, adaptor 243 is typically rigid, and may comprise a metal. Alternatively, the adaptor may not be threaded, as shown in FIG. 25I, in which case the surgeon presses the adaptor into the second bore. In this configuration, the adaptor may be rigid (e.g., may comprise a metal) or flexible (e.g., may comprise rubber). Optionally, the adaptor is conical.

For other applications, the surgeon injects the regenerative material using a needle 244, as shown in FIG. 25J. The surgeon may form the second bore using a dental drill, or form the second bore directly using the needle. For still other applications, the surgeon injects the material through a channel of a drill bit.

Insertion of the regenerative material through a separate bore allows the use of an implant having a narrower lumen 40 and/or delivery tube 50, because the lumen and delivery tube need only allow passage of the fluid as described hereinabove with reference to FIG. 25C, and not the regenerative material, which is generally more viscous than the fluid.

For some applications, the sinus lift is performed using a conventional surgical drill with irrigation, such as internal irrigation, as is known in the art and commercially available. The regenerative material is injected through a second bore, as described hereinabove with reference to FIGS. 25H-J. In addition to allowing the use of a narrower lumen through the drill bit, insertion of the regenerative material through a separate bore allows the use of a narrower drill bit for performing the sinus lift through the first bore.

Figure 26B:
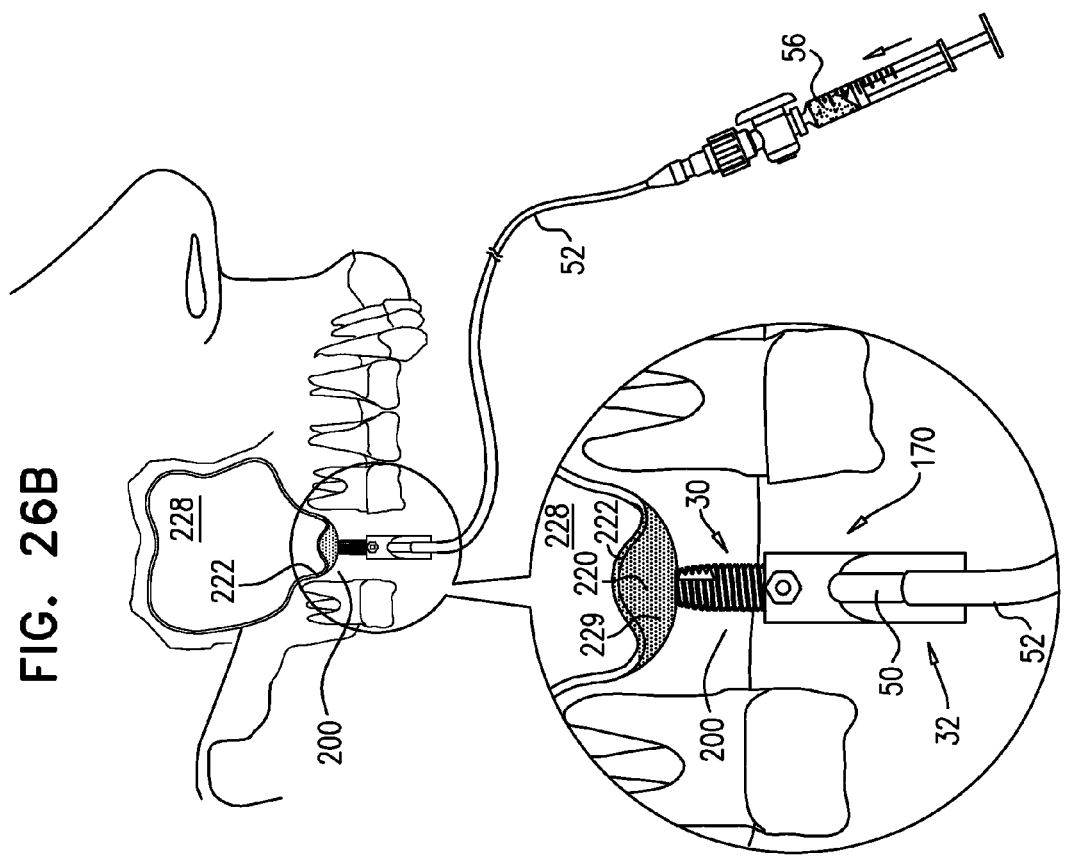
FIGS. 26A-B are schematic illustrations of several steps of another minimally-invasive closed sinus lift surgical procedure for implanting a dental implant, in accordance with an application of the present invention.
Figure 26A:
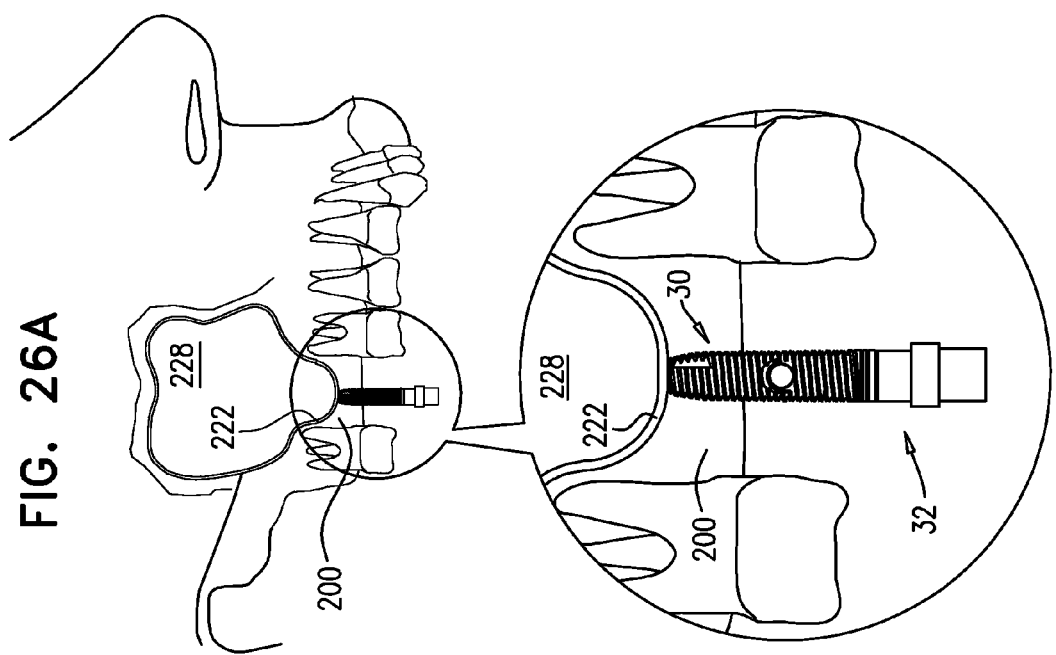

Reference is made to FIGS. 26A-B, which are schematic illustrations of several steps of another minimally-invasive closed sinus lift surgical procedure for implanting dental implant 30, in accordance with an application of the present invention. The procedure is typically employed when a patient's maxillary alveolar ridge lacks sufficient bone mass to support a conventional dental implant. The procedure is particularly appropriate for implanting the configuration of implant 30 described hereinabove with reference to FIGS. 19A-D and 20A-G, optionally in combination with one or more of the features described hereinabove with reference to FIGS. 2A-C and/or 28A-B.

A surgeon begins the procedure by drilling a preliminary bore portion in maxillary alveolar ridge 200, such as described hereinabove with reference to FIG. 25A. After drilling the preliminary bore portion, the surgeon advances dental implant 30 into the bore by screwing the implant into ridge 200 using surgical rotation tool 90 (such as described hereinabove with reference to FIGS. 1A and 1C), as shown in FIG. 26A. In this application, at this stage of the procedure, delivery tube 50 is not yet coupled to implant 30. Because delivery tube 50 is not coupled to the implant, the surgeon can readily rotate the implant even if adjacent teeth are present. This enables implantation of the implant with the same intra-teeth distance possible in conventional implantation procedures of conventional implants.

The surgeon typically screws the implant until distal implant end 38 reaches the end of the osteotomy. The surgeon then advances the implant slightly (typically, by about one additional rotation), causing the implant to break through the top of ridge 200 to below Schneiderian membrane 222, thereby bringing distal opening(s) 41 into fluid communication with a surface of the membrane facing ridge 200, as shown in FIG. 26A. Distal implant end 38 typically does not pass through the top of ridge 200, at least at this stage in the procedure. It is noted that, if necessary to reach sufficient depth for the distal end of the implant to reach the top of the ridge, the surgeon may advance the implant so far as to advance all or a portion of lateral opening 44 into ridge 200. The implant is subsequently withdrawn in order to enable access to lateral opening 44, as described hereinbelow with reference to FIG. 26B.

Optionally, after the initial insertion of the implant into the bore, the surgeon uses a periapical radiograph to estimate remaining distance from implant tip to the sinus floor. The surgeon rotates the implant to penetrate into the sinus, such as by rotating the implant by a number of rotations equal to the remaining distance divided by a constant, e.g., 1.2 mm. Optionally, the surgeon performs an additional periapical radiograph to ensure that the implant has penetrated into the sinus cavity.

The surgeon ensures that upon the final rotation of implant 30, lateral opening 44 faces either in a lingual or buccal direction, in order to provide access to the opening for coupling the retaining element, as described immediately hereinbelow.

After the implant has been advanced to membrane 222, the surgeon decouples rotation tool 90 from applicator 32, and couples retaining element 170 (described hereinabove with reference to FIGS. 19A-D and 20A-G) to applicator 32, as shown in FIG. 26B. Supply tube 52 is coupled to the proximal end of delivery tube 50. At the initial time of coupling of retaining element 170 to applicator 32, the retaining element is in its second position, in which the distal end of delivery tube 50 is not coupled to implant 30, as described hereinabove with reference to FIGS. 19A-C and 20B. The surgeon then transitions retaining element 170 to its first position, thereby coupling the distal end of the delivery tube to the implant, such as described hereinabove with reference to FIGS. 19D and 20C-D.

The surgeon gently lifts and separates membrane 222 from the top of ridge 200 into a maxillary sinus 228, by injecting a fluid 229, such as a biocompatible solution such as normal saline solution or a gas, from fluid source 54 (optionally, under controlled pressure) via supply tube 52, delivery tube 50, and lumen 40, so as to form a cavity 220 under the membrane between the ridge and the membrane (in FIG. 26B, the membrane is shown partially raised). Typically, the surgeon injects sufficient fluid 229 into cavity 220 to inflate the cavity to a vertical height of between about 2 and about 20 mm from the top of ridge 200, such as between about 2 and about 11 mm, e.g., between about 2 and about 8 mm. For some applications, a measured volume of fluid 229 is injected in order to achieve the desired cavity height, such as between about 0.5 and about 6 ml of fluid, e.g., between about 1 and about 4 ml, between about 1 and about 3 ml, or between about 2 and about 4 ml.

For some applications, the surgeon detects that membrane 222 has detached from the top of ridge 200 by observing blood within fluid 229, such as saline solution, returning from the sinus, as described hereinabove with reference to FIG. 25C.

For some applications, the fluid is drained from the cavity, and the surgeon injects a regenerative material 230, such as liquid or gel bone graft, into cavity 220, as described hereinabove with reference to FIG. 25D, mutatis mutandis. Alternatively, for some applications, regenerative material 230 is not injected into the cavity, i.e., the step of the procedure described hereinabove with reference to FIG. 25D is omitted. Fluid 229, which may comprise saline solution, is left in cavity 220, or, alternatively, is drained from the cavity. Further alternatively, instead of injecting regenerative material 230, the surgeon injects an alternative therapeutic material, such as one or a mixture of more than one of the following materials: a bone growth stimulating substance, such as a bone morphogenetic protein (BMP), and blood. Still further alternatively, the surgeon injects regenerative material 230, rather than fluid 229, to lift membrane 222. In this case, the regenerative material typically comprises a liquid.

The surgeon transitions retaining element 170 back to its second position, as described hereinabove with reference to FIGS. 19A-C and 20C-D, and decouples the retaining element from implant 30. After decoupling delivery tube 50 from implant 30, the surgeon further advances (e.g., by rotating or screwing) implant 30 into regenerative material 230 in cavity 220, as described hereinabove with reference to FIG. 25F. As described hereinabove with reference to FIG. 25G, after bone grows in cavity 220 (into regenerative material 230, if injected) and is integrated into ridge 200, an appliance 140, such as a crown, is coupled to implant 30, typically using an abutment 242 coupled to implant 30, as is known in the art. Alternatively, as mentioned above, implant 30 comprises a single-stage transgingival implant/abutment, as is known in the art.

Optionally, the procedure is performed in combination with the techniques described hereinabove with reference is made to FIGS. 25H-J.

Figure 27A:
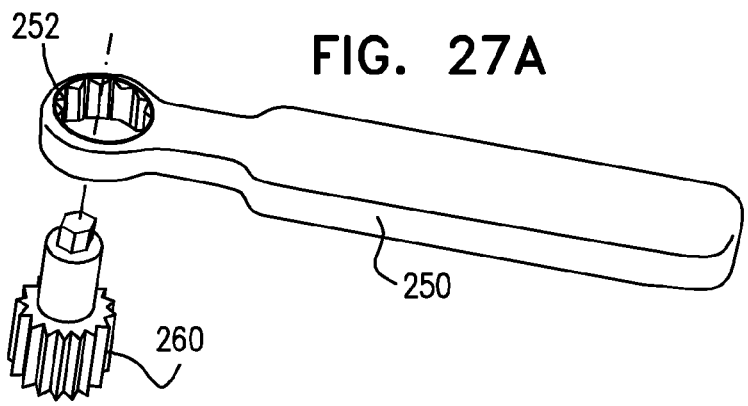
FIGS. 27A and 27B are schematic illustrations of tools and techniques, respectively, for decoupling a delivery tube from the implant of FIGS. 21A-24, in accordance with an application of the present invention.
Figure 27B:
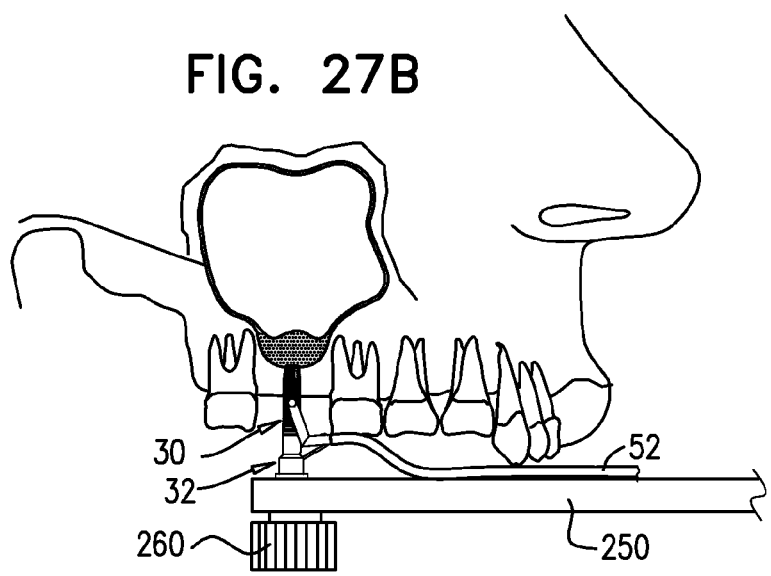

Reference is made to FIGS. 27A and 27B, which are schematic illustrations of tools and techniques, respectively, for decoupling delivery tube 50 from implant 30, in accordance with an application of the present invention. These tools and techniques are particularly useful for the configuration of delivery tube 50, implant 30, and applicator 32 described hereinabove with reference to FIGS. 21A-24.

FIG. 27A shows a stabilization tool 250 and a driver tool 260. A distal end of the stabilization tool is shaped so as to define a coupling opening 252, having, for example, an internal hex width of 6.35 mm. Driver tool 260 may be a conventional hand driver having a hex width of 2.4 mm, for example. For some applications, driver tool 260 is coupled to stabilization tool 250 within coupling opening 252, such that the driver tool is rotatable with respect to the distal end of the stabilization tool.

As shown in FIG. 27B, the surgeon stabilizes applicator 32 by coupling stabilization tool 250 to the proximal end of the applicator. Applicator 32, as shown hereinabove in FIGS. 21A-D and 22A-B, comprises an applicator body, which comprises rotatable surface 92 accessible from the proximal end of the applicator. Applicator 32 is also shaped so as to define a stabilization surface 154 accessible from the proximal end of the applicator. Application of a stabilizing force to stabilization surface 154 stabilizes the implant during rotation of rotatable surface 92. As a result, the decoupling of delivery tube 50 from implant 30 does not dislodge or misalign the implant, which has been precisely placed in a bore in the ridge, as described hereinabove with reference to FIG. 25B. Furthermore, application of the stabilizing force reduces or prevents the transfer of force to the bone from tools operating on the applicator and/or implant.

The outer diameter (or width, such as if the surface is hexagonal) of the stabilizing surface is approximately equal to the internal diameter (or width) of coupling opening 252 of stabilization tool 250, and the stabilizing surface and coupling opening have corresponding shapes.

The surgeon positions stabilization tool 250 such that coupling opening 252 is removably coupled to stabilization surface 154, and applies the stabilizing force to stabilization surface 154. For example, both the coupling opening and the stabilization surface may be hexagonal. Typically, rotatable surface 92 and stabilization surface 154 are configured to facilitate on-axis rotation of the rotatable surface, thereby minimizing any off-axis force that the rotation may cause the apparatus to apply to its surroundings.

In order to decouple delivery tube 50 from implant 30 by breaking thinner portion 72 of the delivery tube, while the stabilization tool stabilizes the applicator, the surgeon removably couples a driver tool 260 to rotatable surface 92 of applicator 32 through opening 252 of stabilization tool 250, and rotates the driver tool, thereby rotating the rotatable surface and breaking thinner portion 72, as described hereinabove with reference to FIGS. 21A-24. For example, driver tool 260 may be a conventional dental hand driver having a hex width of 2.4 mm.

Figure 27C:
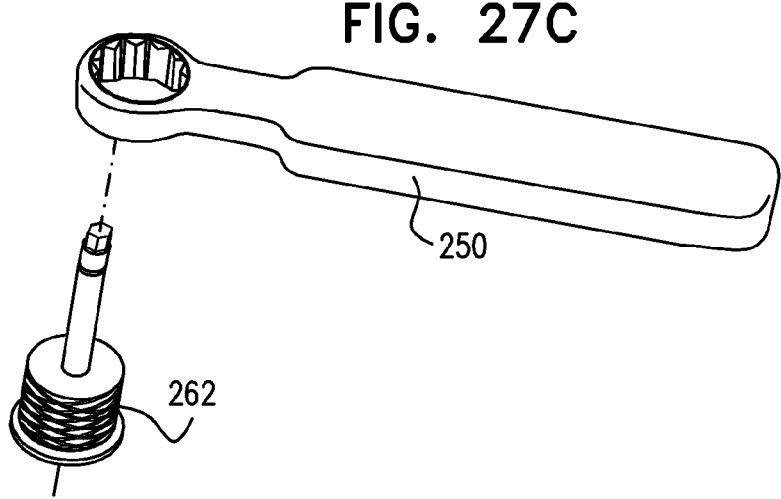
FIGS. 27C and 27D-E are schematic illustrations of a tool and techniques, respectively, for decoupling the applicator from the implant of FIGS. 21A-24, in accordance with an application of the present invention.
Figure 27D:
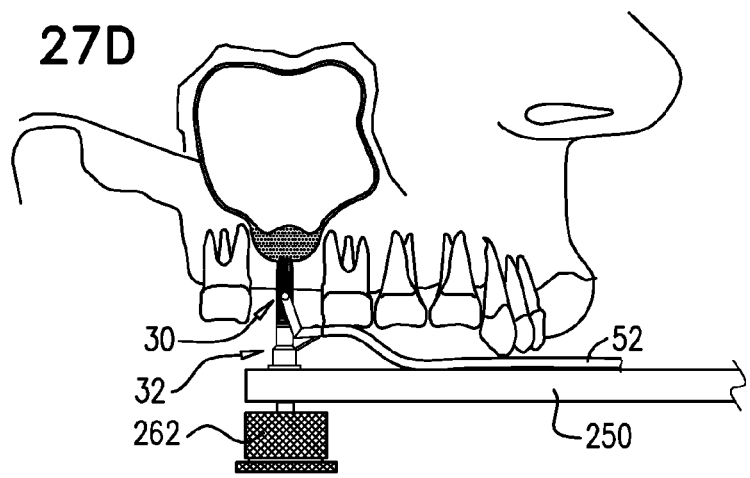
Figure 27E:
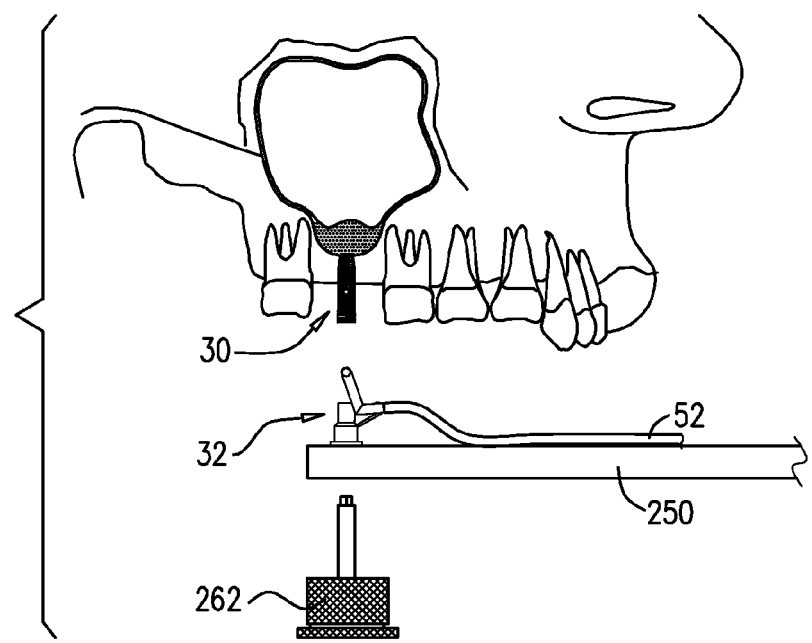

Reference is made to FIGS. 27C and 27D-E, which are schematic illustrations of a tool and techniques for decoupling applicator 32 from implant 30, respectively, in accordance with an application of the present invention. This tool and these techniques are particularly useful for the configuration of delivery tube 50, implant 30, and applicator 32 described hereinabove with reference to FIGS. 21A-24.

FIG. 27C shows a driver tool 262, such as a conventional hand driver having a hex width of 1.25 mm, for example.

As shown in FIG. 27D, the surgeon decouples applicator 32 from implant 30 by inserting driver tool 262 into the head of connecting element 98, described hereinabove with reference to FIGS. 21A-24. The surgeon rotates driver tool 262 (typically counterclockwise) to unscrew connecting element 98, thereby decoupling applicator 32 from implant 30. Typically, stabilizing tool 250 remains coupled to stabilization surface 154 of implant 30 during this decoupling. FIG. 27E shows the applicator after it has been decoupled from the implant, leaving the implant in place in the ridge.

For some applications, the techniques described herein are used for performing nasal floor elevation, mutatis mutandis, in order to implant a dental implant in the incisor position. A bore is formed through a maxillary alveolar ridge in a region of the upper incisors from the front side, and the implant is inserted into the bore at least until the distal opening comes into fluid communication with a surface of a nasal floor membrane facing the ridge. The membrane is raised to form a cavity between the ridge and the membrane.

For some applications, the techniques described herein are used with an inclined entry, for patients in which the residual bone of the maxillary alveolar ridge is too thin to achieve stability. A bore is formed with an inclined entry at a location adjacent the site of the implant where there is sufficient bone, and sinus lift is performed via the bore using the techniques described herein, mutatis mutandis. For some applications, the bore is formed using a biodegradable drilling element that is configured to biodegrade as the regenerative material integrates with the native bone. Regenerative material is injected into the cavity between the ridge and the Schneiderian membrane. Prior to or after the material integrates, a second straight bore is made at the desired implant location through the thin preexisting bone and into the regenerative material or new bone, and a conventional implant is inserted into the bore.

For some applications, the techniques described herein are used with a palatal entry. A bore is formed in the palate (which is thicker than the maxillary alveolar ridge), and sinus lift is performed via the bore using the techniques described herein, mutatis mutandis. For some applications, the bore is formed using a biodegradable drilling element that is configured to biodegrade as the regenerative material integrates with the native bone. The drilling element is withdrawn or allowed to biodegrade. Regenerative material is injected into the cavity between the ridge and the Schneiderian membrane. Prior to or after the material integrates, a second bore is made at the desired implant location through the maxillary alveolar ridge and the new bone, and a conventional implant is inserted into the bore.

For some applications, the regenerative material comprises a composition comprising solid bone graft particles mixed with a physiological solution, such as saline solution, blood, or diluted blood. For example, the solid bone graft particles may comprise freeze-dried bone allograft (FDBA). Typically, the volume concentration of the particles in the composition before filtering is less than 50%, e.g., less than 25%, such as between about 10% and about 20%, as described below. For some applications, two bores are formed through the maxillary alveolar ridge to below the Schneiderian membrane. The regenerative material is injected though a first bore, and at least a portion of the physiological solution drains through a filter in (or in communication with) the second bore, leaving at least a portion of solid bone graft particles in a cavity formed between the ridge and the membrane. Typically, the volume concentration of the particles in the composition after filtering is greater than 50%, e.g., between about 80% and about 100%. For some applications, this technique is used for bones other than the maxillary alveolar ridge, such as a mandibular alveolar ridge.

Figure 28A:
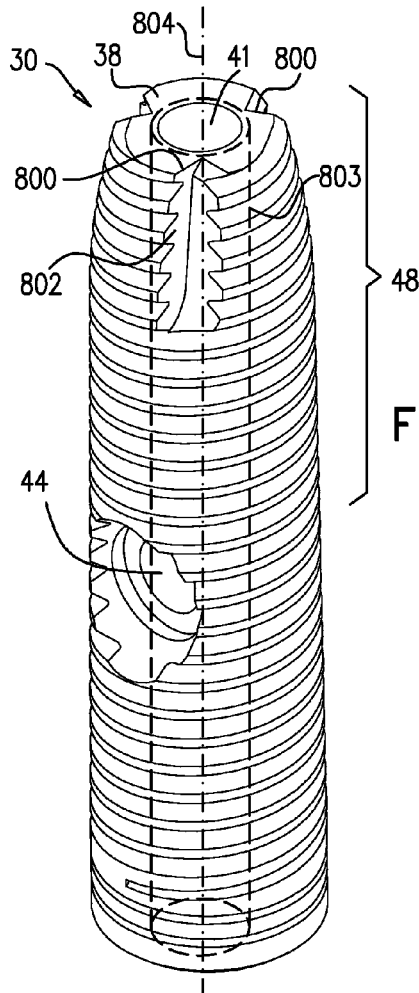
FIGS. 28A-B are schematic lateral and head-on illustrations, respectively, of a configuration of a distal surface of the dental implant of FIGS. 1A-C, in accordance with an application of the present invention.
Figure 28B:
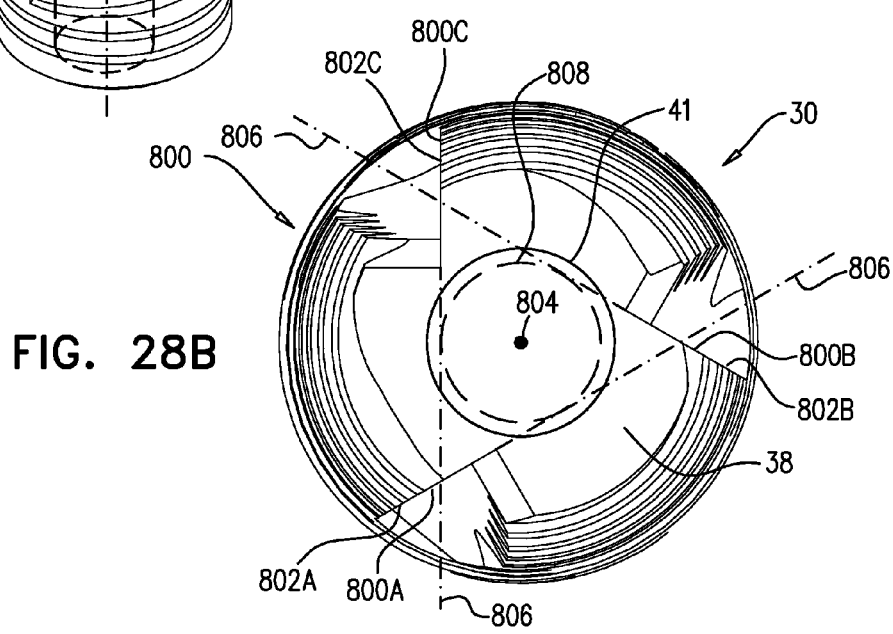

Reference is made to FIGS. 28A-B, which are schematic lateral and head-on illustrations, respectively, of a configuration of a distal surface of dental implant 30, in accordance with an application of the present invention. For some applications, this configuration is used for implants described hereinabove with reference to FIGS. 1A-C, 2A-C, 3A-D, 4A-B, 15-18, 19A-D, 20A-G, and/or 21A-24. As described hereinabove with reference to FIGS. 1A-C, implant 30 is shaped so as to define a lumen therethrough that is open through at least one distal opening 41 to distal portion 48 of the implant that extends from distal implant end 38 of the implant along up to 50% of a longitudinal length of the implant. Typically, the at least one opening is located at the center of the distal implant end.

In the present configuration, distal portion 48 is shaped so as to define at least one surface selected from the group consisting of: at least one end mill cutter surface 800, at least one self-tapping surface 802, and both the at least one end mill cutter surface and the at least one self-tapping surface (as shown in FIGS. 28A-B). Unlike conventional end mill and self-tapping surfaces, the end mill cutter and self-tapping surfaces do not extend into a central area of the implant that defines the lumen. This confining of the surfaces to the outer area of the implant accommodates the distal opening and lumen. For some applications, the end mill and self-tapping surfaces do not extend into a cylindrical area 803, a central axis of which coincides with a central axis 804 of the implant, and which area extends along the entire length of the implant. Cylindrical area 803 typically has a diameter of at least 0.3 mm, such as at least 0.5 mm, or at least 1.5 mm. For some applications, the diameter of the lumen is between 0.3 and 2 mm, such as between 0.5 and 2 mm, e.g., between 1.5 and 1.6 mm. For some applications, the greatest diameter of the implant (i.e., the diameter of the implant at its widest portion) is no more than 5 mm, such as no more than 4.2 mm, or is between 3 and 6.5 mm.

The end mill cutter surface creates bone fragments and bone dust that protects the Schneiderian membrane or periosteal tissue as the implant is advanced through the bone. In addition, the end mill cutter surface grinds the bone of the ridge, which is generally effective for breaking through bone. Distal portion 48 both engages the lower portion of the bone while at the same time breaking through the upper portion of the bone.

For some applications, end mill cutter surface 800 is shaped so as to define exactly two, exactly three, exactly four, exactly five, or exactly six cutting surfaces. For example, in the configuration shown in FIGS. 28A and 28B, end mill cutter surface 800 defines exactly three cutting surfaces 800A, 800B, and 800C, i.e., is tripartite, and self-tapping surface 802 defines exactly three self-tapping surfaces 802A, 802B, and 802C. Typically, the cutting surfaces are distributed evenly about a central axis 804 of the implant, offset from the center. Lines 806 respectively defined by the cutting surfaces are typically tangential to a circle 808 having a center which is intersected by central axis 804 of the implant (the circle may or may not have the same radius as distal opening 41). Thus, for example, for applications in which the end mill cutter surface defines exactly two cutting surfaces 802, lines 806 are parallel to one another; for applications in which the end mill cutter surface defines exactly three cutting surfaces 802, lines 806 form a triangle; and, for application in which the end mill cutter surface defines exactly four cutting surfaces 802, lines 806 form a square.

For some applications, distal portion 48 is shaped so as to define a conical cross-section that is configured to cause bone condensation, which generally improves bone density.

Figure 29F:
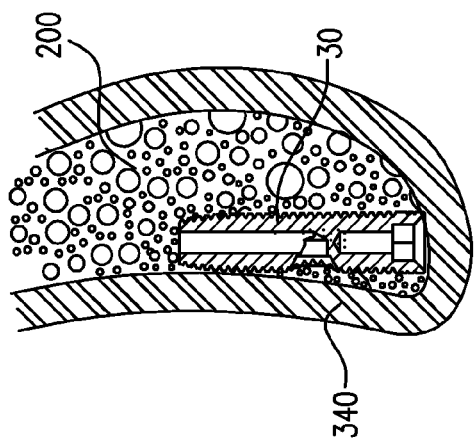

Reference is made to FIGS. 29A-F, which are schematic illustrations of several steps of a minimally-invasive closed lateral ridge augmentation surgical procedure for implanting dental implant 30, in accordance with an application of the present invention. The procedure is typically employed when a patient's maxillary or mandibular alveolar ridge 200 lacks sufficient bone width to support a dental implant, as shown in FIG. 29A. For example, the procedure may be employed for implanting an implant to replace the upper canines, lower molars, upper incisors, or lower incisors.

The lateral ridge augmentation procedure may be performed with the configuration of implant 30 described hereinabove with reference to FIGS. 19A-D (as shown in and described hereinbelow with reference to FIGS. 29A-F), with the configuration of implant 30 described hereinabove with reference to FIGS. 20A-G, or with the configuration of implant 30 described hereinabove with reference to FIGS. 15-18. Alternatively the lateral ridge augmentation procedure may be performed with the configuration of implant 30 described hereinabove with reference to FIGS. 1A-3D, in which case the techniques described hereinbelow with reference to FIGS. 29A-F are performed in combination with the techniques described hereinabove with reference to FIGS. 25A-G. Further alternatively, the lateral ridge augmentation procedure may be performed with the configuration of implant 30 described hereinabove with reference to FIGS. 21A-24, in which case the techniques described hereinbelow with reference to FIGS. 29A-F are performed in combination with the techniques described hereinabove with reference to FIGS. 27A-E. This closed lateral ridge augmentation surgical procedure may be performed in combination with other techniques described herein. For some applications, the distal opening of the lumen is located on a lateral surface of the implant near the distal end, rather than on the distal end itself.

A surgeon begins the procedure by preparing the oral facial region, and administering a local anesthetic. Optionally, the surgeon initiates an osteotomy in alveolar ridge 200 by making a preliminary portion of a bore using a dental drill, such as a conventional sinus bur. This preliminary bore portion typically has a diameter of between about 1 and about 7 mm, e.g., between about 2 and about 6 mm. Optionally, the surgeon widens the bore using a series of successively wider drill bits, until a desired bore diameters is achieved (for example, the largest drill bit may have a diameter of 3.65 mm for an implant having a diameter of 4.2 mm, or a diameter of 4.2 mm for an implant having a diameter of 5 mm). The bore may be measured using techniques known in the art, such as CT, x-ray, or x-ray with a depth guide. For some applications, a surgical guide is used to ensure clearance between the center of the osteotomy and the nearest tooth surfaces. Optionally, a pre-surgery radiograph (e.g., CT or x-ray) is performed, to enable the surgeon to estimate the necessary depth of the osteotomy.

After drilling the preliminary bore portion, the surgeon advances dental implant 30 into the bore by screwing the implant into ridge 200 using surgical rotation tool 90 coupled to applicator 32, as described hereinabove with reference to FIGS. 1A and 1C.

As shown in FIG. 29B, the surgeon inserts implant 30 into the bore at least until the distal opening comes into fluid communication with periosteal tissue 340 covering a lateral surface of the bone.

After the implant has been advanced, the surgeon decouples rotation tool 90 from applicator 32, and couples retaining element 170 (described hereinabove with reference to FIGS. 19A-D and 20A-G) to applicator 32, as shown in FIG. 29C. Supply tube 52 is coupled to the proximal end of delivery tube 50. At the initial time of coupling of retaining element 170 to applicator 32, the retaining element is in its second position, in which the distal end of delivery tube 50 is not coupled to implant 30, as described hereinabove with reference to FIGS. 19A-C and 20B. The surgeon then transitions retaining element 170 to its first position, thereby coupling the distal end of the delivery tube to the implant, as described hereinabove with reference to FIGS. 19D and 20C-D.

The surgeon delaminates periosteal tissue 340 from the bone by injecting fluid 229 from fluid source 54 via supply tube 52, delivery tube 50, and lumen 40 of the implant, to form a cavity 320 between the bone and periosteal tissue 340, as shown in FIG. 29C.

Figure 29E:
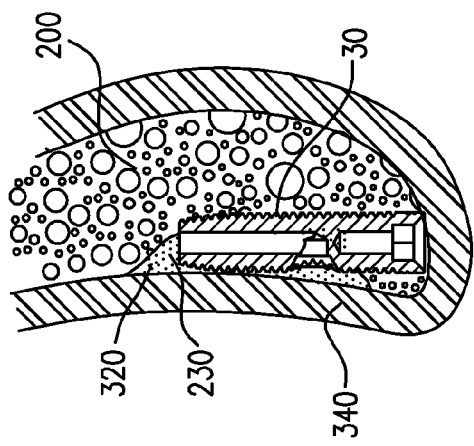
Figure 29D:
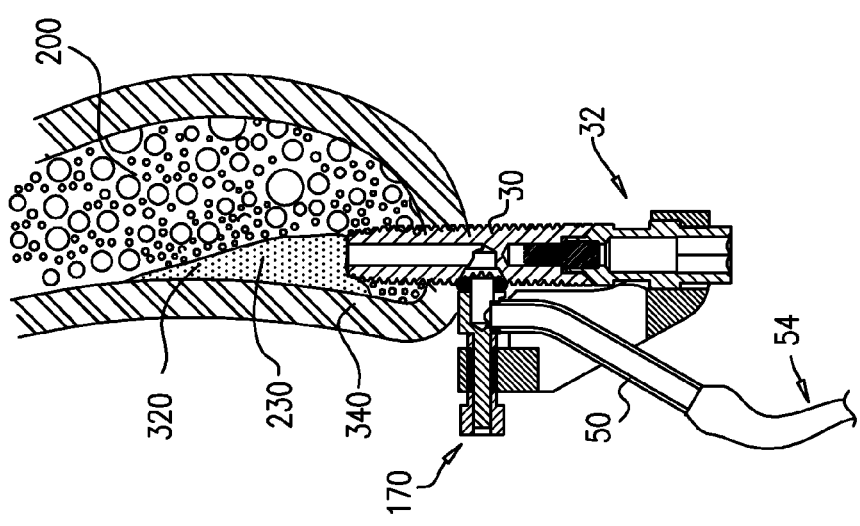

For some applications, the fluid is drained from the cavity, and the surgeon injects a regenerative material 230, such as liquid or gel bone graft, into cavity 320, as shown in FIG. 29D. Fluid source 54 or a separate syringe or powered drug delivery device is used for injecting the regenerative material. If a separate syringe or device is used to inject the material, the material may be provided via supply tube 52, or via a separate supply tube. Regenerative material 230 may comprise any of the materials mentioned hereinabove with reference to 25D Optionally, the system monitors and generates an output indicative of the pressure of the regenerative material as it is injected. Alternatively, for some applications, regenerative material 230 is not injected into the cavity. Fluid 229, which may comprise saline solution, is left in cavity 320, or, alternatively, is drained from the cavity. Further alternatively, instead of injecting regenerative material 230, the surgeon injects an alternative therapeutic material, such as one or a mixture of more than one of the following materials: a bone growth stimulating substance, such as a bone morphogenetic protein (BMP), and blood. Still further alternatively, the surgeon injects regenerative material 230, rather than fluid 229, to delaminate periosteal tissue 340. In this case, the regenerative material typically comprises a liquid.

For some applications, the system measures the volume of fluid 229 injected into the cavity while forming the cavity, at the step of the procedure described hereinabove with reference to FIG. 29C. Responsively to the measured volume, the surgeon determines an amount of regenerative material 230 to inject into cavity 320 at the step of the procedure described hereinabove with reference to FIG. 29D. Typically, the amount of regenerative material 230 is approximately equal to the volume of injected fluid 229, or slightly greater or less than the volume of the injected fluid. As a result, waste of regenerative material 230 is generally minimized.

For some applications, the surgeon uses a flexible wire as a piston to help push the regenerative material through the supply tubes and/or lumen. This technique may be helpful when the regenerative material is viscous and thus difficult to inject using an ordinary syringe.

The surgeon transitions retaining element 170 back to its second position, as described hereinabove with reference to FIGS. 19A-C and 20C-D, and decouples the retaining element from implant 30. After decoupling delivery tube 50 from implant 30, the surgeon further advances (e.g., by rotating or screwing) implant 30 into regenerative material 230 in cavity 320, as shown in FIG. 29E. This additional advancing of the implant advances the lateral surface of implant 30 at least until lateral opening 44 is positioned entirely within the bore in ridge 200 and/or in regenerative material 230 in cavity 320. Such positioning of both ends of the lumen within bone substantially reduces the risk of infection, because the proximal end of implant 30 that is exposed to the oral cavity or gingiva is permanently closed.

The surgeon decouples applicator 32 from implant 30, such as by pulling the male coupling element out of the female coupling element, or using the tool and techniques described hereinabove with reference to FIG. 27C-E. Typically, the surgeon couples a cover screw to the proximal end of the implant using a hand driver, and sutures the gingiva.

As shown in FIG. 29F, bone grows in cavity 220 (into regenerative material 230, if injected) and is integrated into ridge 200. Thereafter, an appliance, such as a crown, is coupled to implant 30, typically using an abutment coupled to the implant, as is known in the art. Alternatively, implant 30 comprises a single-stage transgingival implant/abutment, as is known in the art.

Figures 30, 31:
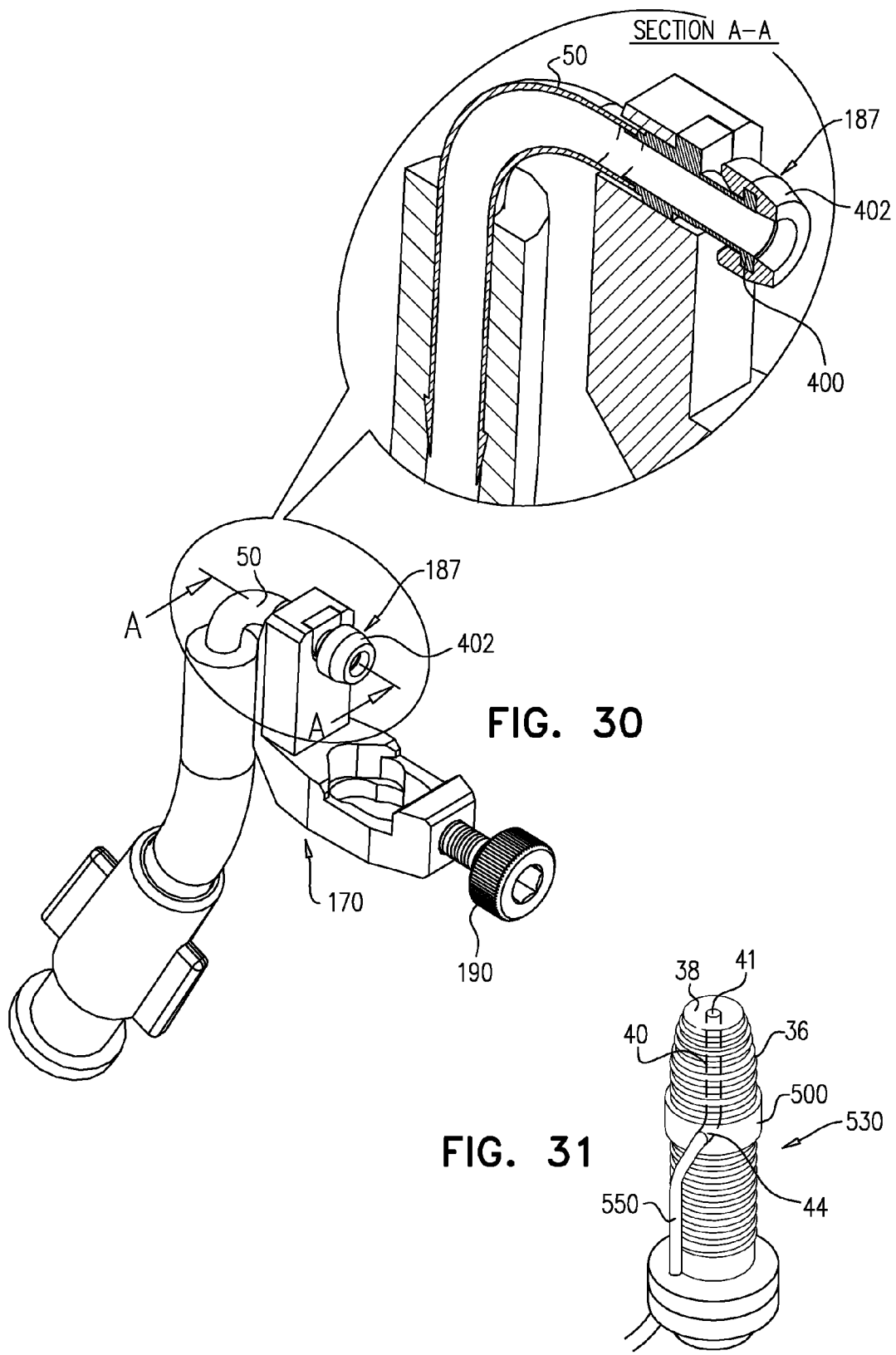
FIG. 30 is a schematic illustration of a configuration of a sealing element of a retaining element, in accordance with an application of the present invention.
FIG. 31 is a schematic illustration of a removable coupling element coupled to a dental implant, in accordance with an embodiment of the present invention.

Reference is now made to FIG. 30, which is a schematic illustration of a configuration of sealing element 187 of retaining element 170, in accordance with an application of the present invention. Although illustrated for the configuration of retaining element 170 described hereinabove with reference to FIGS. 20A-G, this configuration of sealing element 187 may also be used for the configuration of retaining element 170 described hereinabove with reference to FIGS. 15, 16, 17A-E, and 18 and FIGS. 19A-D.

In this configuration, retaining element 170 comprises sealing element 187 at the distal end of delivery tube 50. Typically, the distal end of delivery tube 50 is embedded in sealing element 187. Delivery tube 50 includes an increased-diameter distal portion 400, which may be disc-shaped, which helps couple tube 50 to sealing element 187, and forms a surface that applies even pressure to the sealing element, thereby helping the sealing element to seal with lateral opening 44 of the implant. The sealing element may also be coupled to the tube using an adhesive. Sealing element 187 typically comprises silicone, silicone rubber, or another biocompatible compliant sealing material. For some applications, a distal portion 402 of sealing element 187 is conical. For example, distal portion 402 may be shaped as a cone that has an opening angle of between 0 and 90 degrees, such as between about 15 and about 75 degrees, e.g., between about 15 and about 60 degrees.

Reference is now made to FIG. 31, which is a schematic illustration of a removable coupling element 500 coupled to a dental implant 530, in accordance with an embodiment of the present invention. Implant 530 is generally similar to implant 30, described hereinabove, and may implement all or a portion of the features thereof. In particular, implant 530 is shaped so as to define lumen 40 therethrough that is open through distal opening 41 to a distal portion of the implant. A proximal end of lumen 40 has a lateral opening 44 through a lateral external surface of the implant.

Removable coupling element 500 removably secures a delivery tube 550 to lateral opening 44. When the surgeon decouples delivery tube 550 from implant 530, the surgeon also decouples coupling element 500 from the implant. The coupling element is typically removably coupled to an external surface of the implant. For some applications, coupling element 500 is configured to be placed around at least a portion of the circumference of the implant, such as the entire circumference.

In an embodiment, coupling element 500 comprises an elastic band that is placed around the entire circumference of the implant, as shown in FIG. 31. The distal end of delivery tube 550 may pass through an opening in the band, such that the band holds the tube in place coupled to lateral opening 44. For other applications, coupling element 500 comprises a more rigid material.

Reference is now made to FIGS. 32A-C, which are schematic illustrations of implant 30 and dental applicator 32, in accordance with an application of the present invention. FIG. 32A is an isometric view of the implant and applicator, and FIGS. 32B and 32C are cross-sectional views of FIG. 32A along lines XXXIIB-XXXIIB and XXXIIC-XXXIIC, respectively. In this configuration, applicator 32 is shaped so as to define:
- a distal coupling surface 600, which is configured to removably engage applicator 32 with a proximal end 602 of dental implant 30;
- a proximal coupling surface 604; and
- a longitudinal portion 606, which is shaped so as to define an external surface 608 that is rotationally asymmetric.

Distal and proximal coupling surfaces 600 and 604 share a common central longitudinal axis 610. Because of this common axis, rotation of proximal coupling surface 604 causes corresponding rotation of distal coupling surface 600.

As used in the present application, including in the claims, a three-dimensional surface is "rotationally symmetric" if the surface has n-fold (also called n-order) rotational symmetry with respect to an axis, wherein n is greater than (and not equal to) 1, such that rotation of the surface by an angle of 360°/n does not change the appearance of the surface. For example, all regular polygonal right cylinders and circular right cylinders are rotationally symmetric. A three-dimensional surface is "rotationally asymmetric" if it is not rotationally symmetric.

(By way of simplified example in two dimensions, a two-dimensional shape is rotationally symmetric if the shape has n-fold rotational symmetry with respect to a point, wherein n is greater than (and not equal to) 1, such that rotation of the shape by an angle of 360°/n does not change the appearance of the shape. For example, circles and all regular polygons (e.g., equilateral triangles, squares, and regular pentagons) are rotationally symmetric, while trapezoids are rotationally asymmetric.)

Reference is made to FIG. 33, which is a schematic cross-sectional illustration showing retaining element 170 removably coupled to applicator 32, in accordance with an application of the present invention. For some applications, a retaining element, such as retaining element 170, described hereinabove with reference to FIGS. 20A-F, is removably coupled to applicator 32. The retaining element is shaped such that rotationally-asymmetric surface 608 of applicator 32 constrains a rotational orientation of the retaining element with respect to the applicator, such that the retaining element can only be removably coupled to the applicator at a single rotational orientation with respect to the applicator. Such rotational constraint typically serves to rotationally align the distal end of delivery tube 50 with lateral opening 44 of implant 30.

Reference is again made to FIGS. 32A-C. Typically, distal coupling surface 600 extends from a distal end 620 of applicator 32 toward proximal coupling surface 604 (although distal coupling surface 600 typically does not reach proximal coupling surface 604). Alternatively or additionally, proximal coupling surface 604 extends from a proximal end 622 of applicator 32 toward distal coupling surface 600 (although proximal coupling surface 604 typically does not reach distal coupling surface 600).

Typically, distal coupling surface 600 is rotationally symmetric and not circular, to enable the surface to engage a coupling surface of the implant. For example, distal coupling surface 600 may be regularly polygonally shaped, such as a hexagonally or an octagonally shaped. Alternatively or additionally, proximal coupling surface 604 is rotationally symmetric and not circular, to enable the surface to engage a tool, such as a wrench. For example, proximal coupling surface 604 may be regularly polygonally shaped, such as a hexagonally or a squarely shaped.

For some applications, distal coupling surface 600 is longitudinally non-overlapping with rotationally-asymmetric external surface 608. Alternatively or additionally, for some applications proximal coupling surface 604 is longitudinally non-overlapping with rotationally-asymmetric external surface 608.

Typically, distal coupling surface 600 is male (as shown) or female (not shown). Alternatively or additionally, proximal coupling surface 604 is male (as shown) or female (not shown). Further alternatively or additionally, proximal coupling surface 604 is shaped so as to simultaneously define both male and female coupling elements (not shown).

For some applications, applicator 32 is shaped so as to define a channel 630 therethrough, which is open to both distal and proximal ends 620 and 622 of applicator 32, and which is coaxial with central longitudinal axis 610. The applicator may comprise connecting element 98, which is configured to be disposed at least partially in channel 630, and to removably couple the applicator to proximal implant end 602. For some applications, connecting element 98 comprises a shaft 632, at least a portion of which defines a screw thread 634. The screw thread engages a threaded coupling surface 636 of implant 30 (which may be more distally disposed than a coupling surface 638 of the implant which distal coupling surface 600 engages).

Alternatively (configuration not shown), rotationally-asymmetric external surface 608 extends from distal end 620 of applicator 32 toward proximal end 622 of applicator 32 (although surface 608 does not necessarily reach proximal end 622). In this case, distal coupling surface 600 is typically female, and longitudinally overlaps rotationally-asymmetric external surface 608. Alternatively or additionally (configuration not shown), rotationally-asymmetric external surface 608 extends from proximal end 622 of applicator 32 toward distal end 620 of applicator 32 (although surface 608 does not necessarily reach distal end 620). In this case, proximal coupling surface 604 is typically female, and longitudinally overlaps rotationally-asymmetric external surface 608. In an application of the present invention, a dental applicator is provided that has the configuration of dental applicator 32 described hereinabove with reference to FIGS. 32A-C and 33, except that external surface 608 of longitudinal portion 606 has 2-fold rotational symmetry. The retaining element thus can be removably coupled to the applicator at exactly two rotational orientations with respect to the applicator.

In some applications of the present invention, a dental surgical method is provided that comprises:
(a) implanting a first set of dental implants in a maxillary alveolar ridge anterior to the maxillary sinus, and assembling a first dental prosthesis on the first implants;
(b) performing a sinus lift, optionally using any of the sinus lift techniques described herein, and implanting a second set of one or more implants, such as dental implants 30, in the ridge posterior to the first set of implants, in the vicinity of the sinus lift; at this stage of the procedure, no dental prostheses are assembled on the second set of implants; and
(c) subsequently to steps (a) and (b) (typically at least four months thereafter, such as at least six months thereafter), assembling a second prosthesis on both the first and the second sets of implants, i.e., the first set of implants anterior to the sinus and the second set of implants implanted in conjunction with the sinus lift; the second prosthesis may be entirely separate from the first prosthesis, or may comprise a portion of the first prosthesis.

Step (a) may be performed before or after step (b).

As is well known in the art, an all-on-four dental implant procedure is generally used in cases in which all of the teeth are missing in a jaw (usually the upper jaw). The all-on-four dental implant procedure serves as an alternative to a sinus lift (many patients would prefer not to undergo a sinus lift). The entire rehabilitation is built on four implants, two at anterior site of the maxillary alveolar ridge and two angled a posterior site of the ridge. This technique has the advantage of a quick rehabilitation without sinus surgery, but the disadvantage of an inferior long-term solution compared with a more solid foundation based on six or eight implants including implants in the posterior region of the jawbone. Similar techniques may use more than four implants, but they are still limited to implants placed in the region of the jawbone which is anterior to the maxillary sinus.

In some applications of the present invention, the dental surgical method described two paragraphs above comprises performing an all-on-four dental implant procedure in combination with a sinus lift procedure described herein and/or in the applications incorporated by reference hereinbelow. At step (a) of the method, an all-on-four procedure is performed by implanting the first set of implants, two at anterior site of the maxillary alveolar ridge and two angled a posterior site of the ridge, and a first dental prosthesis is assembled on the first set of implants. At step (b) of the method, during the sinus lift procedure, a second set of one or more dental implants, such as dental implant 30, are implanted, but are not yet used for supporting a dental prosthesis. Typically, the all-on-four procedure and the sinus lift procedure are performed during a first, single surgical procedure. Alternatively, they may be performed in separate surgical procedures. The patient receives temporary rehabilitation using the all-on-four method. Typically at least four months (e.g., about six to nine months) after the first surgical procedure, a second surgical procedure is performed, in which the temporary all-on-four first prosthesis is fully or partially replaced with a second prosthesis that provides a permanent restoration assembled on the first set of implants, as well as on the additional second set of one or more implants implanted during the sinus lift procedure. As a result, the patient receives a stable, long-term solution.

The scope of the present invention includes embodiments described in the following patent applications, which are assigned to the assignee of the present application and are incorporated herein by reference. In an embodiment, techniques and apparatus described in one or more of the following applications are combined with techniques and apparatus described herein:

U.S. application Ser. No. 12/240,353, filed Sep. 29, 2008, which issued as U.S. Pat. No. 7,934,929;

U.S. application Ser. No. 12/485,199, filed Jun. 16, 2009, which issued as U.S. Pat. No. 8,029,284;

International Application PCT/IL2009/000931, filed Sep. 29, 2009, which published as PCT Publication WO 2010/035270;

International Application PCT/IL2010/000252, filed Mar. 24, 2010, which published as PCT Publication WO 2010/146573; and/or U.S. application Ser. No. 12/661,795, filed Mar. 24, 2010, which published as US Patent Application Publication 2010/0255446.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   a dental implant having a lateral external surface, the implant being shaped so as to define a lumen therethrough having a lateral opening through the lateral external surface;
   a delivery tube having a distal tube end;
   a retaining element, which is configured to assume (a) a first position in which the retaining element removably couples the distal tube end to the implant such that the delivery tube is in fluid communication with the lumen via the lateral opening, and (b) a second position in which the retaining element does not couple the distal tube end to the implant; and
   an applicator, which is removably coupled to a proximal implant end of the implant,
   wherein the retaining element is coupled to the delivery tube and shaped so as to be removably couplable to the proximal implant end via the applicator, such that the retaining element removably couples the distal tube end to the implant when the retaining element is removably coupled to the proximal implant end via the applicator and is in the first position.

2. The apparatus according to claim 1, further comprising a sealing element, which is configured to removably sealingly couple the delivery tube to the implant when the retaining element is in the first position.

3. The apparatus according to claim 2, wherein the sealing element comprises an element selected from the group consisting of: an o-ring and a gasket.

4. The apparatus according to claim 2, wherein the distal tube end is embedded in the sealing element.

5. The apparatus according to claim 1, wherein at least a portion of the retaining element is disposed at least 1.5 cm from the lateral opening when the retaining element is in the first position.

6. The apparatus according to claim 1, wherein the retaining element comprises a retaining element body, a portion of which is configured to be disposed alongside the implant, from the applicator to the lateral opening of the implant, when the retaining element is removably coupled to the proximal implant end via the applicator.

7. The apparatus according to claim 6, wherein the retaining element further comprises a shaft, which is configured such that rotation of the shaft brings the distal tube end into contact with the lateral opening of the implant, to sealingly couple the distal tube end to the lateral opening.

8. The apparatus according to claim 7, wherein the retaining element is configured such that the shaft and the distal tube end are positioned at circumferentially opposite sides of the implant, when the retaining element is coupled to the proximal implant end via the applicator, and at least when the retaining element is in the first position.

9. The apparatus according to claim 7, wherein the retaining element is configured such that the shaft and the distal tube end are positioned at a same circumferential side of the implant, when the retaining element is coupled to the proximal implant end via the applicator, and at least when the retaining element is in the first position.

10. The apparatus according to claim 7, wherein the shaft is oriented such that a longitudinal axis thereof forms an angle of 90 degrees with a longitudinal axis of the implant, when the retaining element is coupled to the proximal implant end via the applicator, and at least when the retaining element is in the first position.

11. The apparatus according to claim 7, wherein an external surface of a portion of the shaft is shaped so as to define a screw thread, which passes through a lumen of the retaining element body that is shaped so as to define a corresponding screw thread.

12. The apparatus according to claim 1, wherein the retaining element is shaped so as to be removably couplable to the applicator, such that the retaining element removably couples the distal tube end to the implant when the applicator is removably coupled to the proximal implant end, and the retaining element is removably coupled to the applicator in the first position.

13. The apparatus according to claim 12, wherein the applicator is shaped so as to define a longitudinal portion that is shaped so as to define an external surface that is rotationally asymmetric.

14. The apparatus according to claim 13, wherein the retaining element is shaped such that the rotationally-asymmetric surface of the applicator constrains a rotational orientation of the retaining element to a single rotational orientation with respect to the applicator, and rotationally aligns the distal tube end with the lateral opening of the implant.

15. Apparatus comprising:
a dental implant having a lateral external surface, the implant being shaped so as to define a lumen therethrough having a lateral opening through the lateral external surface; and
a delivery tube having a distal tube end, which distal tube end is removably coupled to the implant at a first interface, such that the delivery tube is in fluid communication with the lumen via the lateral opening,
wherein the delivery tube is removably coupled to the implant at a second interface remote from the first interface, so as to prevent movement of the distal tube end with respect to the implant.

16. The apparatus according to claim 15, wherein the delivery tube is directly removably coupled to the implant at the second interface.

17. The apparatus according to claim 15, wherein the delivery tube is indirectly removably coupled to the implant at the second interface.

18. The apparatus according to claim 17, further comprising an applicator, which (a) is removably coupled to a proximal implant end of the implant at the second interface, and (b) indirectly removably couples the delivery tube to the implant.

19. A method comprising:
providing (a) a dental implant having a lateral external surface, the implant being shaped so as to define a lumen therethrough having a lateral opening through the lateral external surface, (b) a delivery tube having a distal tube end, and (c) a retaining element;
causing the retaining element to assume a first position in which the retaining element removably couples the distal tube end to the implant such that the delivery tube is in fluid communication with the lumen via the lateral opening; and
causing the retaining element to assume a second position in which the retaining element does not couple the distal tube end to the implant,
wherein causing the retaining element to assume the first position comprises removably coupling the retaining element to a proximal implant end of the implant via an applicator removably coupled to the proximal implant end, and causing the retaining element to assume the first position, and
wherein removably coupling the retaining element to the proximal implant end via the applicator comprises removably coupling the retaining element to the applicator.

20. The method according to claim 19, wherein causing the retaining element to assume the second position comprises causing the retaining element to assume the second position after causing the retaining element to assume the first position.

21. The method according to claim 19, wherein causing the retaining element to assume the second position comprises causing the retaining element to assume the second position before causing the retaining element to assume the first position.

22. The method according to claim 19, further comprising providing a sealing element, which is configured to removably sealingly couple the delivery tube to the implant when the retaining element is in the first position.

23. The method according to claim 19, wherein at least a portion of the retaining element is disposed at least 1.5 cm from the lateral opening when the retaining element is in the first position.

24. The method according to claim 19, wherein the applicator is shaped so as to define a longitudinal portion that is shaped so as to define an external surface that is rotationally asymmetric.

25. A method comprising:
providing (a) a dental implant having a lateral external surface, the implant being shaped so as to define a lumen therethrough having (i) a lateral opening through the lateral external surface and (ii) at least one distal opening through a distal external surface of the implant, (b) a delivery tube having a distal tube end, and (c) a retaining element;
causing the retaining element to assume a first position in which the retaining element removably couples the distal tube end to the implant such that the delivery tube is in fluid communication with the lumen via the lateral opening;
forming a bore through a maxillary alveolar ridge;
inserting the implant into the bore at least until the distal opening comes into fluid communication with a surface of a Schneiderian membrane facing the ridge;
raising the membrane to form a cavity between the ridge and the membrane, by injecting a liquid through the lumen via the delivery tube when the retaining element is in the first position such that the distal tube end is removably coupled to the implant;
decoupling the distal tube end from the implant by transitioning the retaining element from the first position to a second position in which the retaining element does not couple the distal tube end to the implant; and
further rotating the implant until the lateral opening is positioned entirely within at least one location selected from the group consisting of: the bore in the ridge, and the cavity between the ridge and the membrane.

26. A method comprising:
providing (a) a dental implant having a lateral external surface, the implant being shaped so as to define a lumen therethrough having a lateral opening through the lateral external surface, (b) a delivery tube having a distal tube end, and (c) a retaining element;
causing the retaining element to assume a first position in which the retaining element removably couples the distal tube end to the implant such that the delivery tube is in fluid communication with the lumen via the lateral opening; and
causing the retaining element to assume a second position in which the retaining element does not couple the distal tube end to the implant,
wherein causing the retaining element to assume the first position comprises removably coupling the retaining element to a proximal implant end of the implant via an applicator removably coupled to the proximal implant end, and causing the retaining element to assume the first position, and
wherein the retaining element further comprises a shaft, and wherein causing the retaining element to assume the first position comprises rotating the shaft to bring the distal tube end into contact with the lateral opening of the implant, to sealingly couple the distal tube end to the lateral opening.

27. The method according to claim 26, wherein removably coupling the retaining element to proximal implant end via the applicator comprises positioning the shaft and the distal tube end at circumferentially opposite sides of the implant.

28. A method comprising:
providing (a) a dental implant having a lateral external surface, the implant being shaped so as to define a lumen therethrough having a lateral opening through the lateral external surface, and (b) a delivery tube having a distal tube end;

removably coupling the distal tube end to the implant at a first interface, such that the delivery tube is in fluid communication with the lumen via the lateral opening; and removably coupling the delivery tube to the implant at a second interface remote from the first interface, so as to prevent movement of the distal tube end with respect to the implant.

* * * * *